US010803156B2

(12) United States Patent
Tanaka et al.

(10) Patent No.: US 10,803,156 B2
(45) Date of Patent: Oct. 13, 2020

(54) BIOMETRICS SYSTEM, BIOLOGIC INFORMATION STORAGE, AND PORTABLE DEVICE

(71) Applicants: Masahide Tanaka, Osaka (JP); Tohru Matsui, Nara (JP)

(72) Inventors: Masahide Tanaka, Osaka (JP); Tohru Matsui, Nara (JP)

(73) Assignee: NL GIKEN INCORPORATED, Osaka (JP)

( * ) Notice: Subject to any disclaimer, the term of this patent is extended or adjusted under 35 U.S.C. 154(b) by 702 days.

(21) Appl. No.: 14/536,594

(22) Filed: Nov. 8, 2014

(65) Prior Publication Data

US 2015/0066534 A1    Mar. 5, 2015

Related U.S. Application Data

(63) Continuation of application No. 13/549,420, filed on Jul. 14, 2012, now Pat. No. 8,913,796, which is a
(Continued)

(30) Foreign Application Priority Data

Feb. 2, 2006 (JP) .................. 2006-026393
Feb. 2, 2006 (JP) .................. 2006-026401

(51) Int. Cl.
*G06F 21/32* (2013.01)
*G06K 9/00* (2006.01)
(Continued)

(52) U.S. Cl.
CPC .............. *G06F 21/32* (2013.01); *A61B 5/117* (2013.01); *G06F 19/3418* (2013.01);
(Continued)

(58) Field of Classification Search
CPC ......... G06F 19/322; G06F 19/323–327; G06F 21/32; G06F 19/3418; G06Q 50/22;
(Continued)

(56) References Cited

U.S. PATENT DOCUMENTS 7,849,184 B1 * 12/2010 Kahn .................. G06F 11/3055
709/224
2001/0051787 A1 * 12/2001 Haller ....................... G06F 8/65
604/66

(Continued)

FOREIGN PATENT DOCUMENTS

WO    WO-2003-0950 A2 * 11/2003 ............. A61N 1/372
WO    WO-2006108858 A1 * 10/2006 ............. G16H 40/40

*Primary Examiner* — Jason S Tiedeman

(57) ABSTRACT

In a biometrics system for a building entrance unlocking or a bank account authentication, reference information registered under administration by the system is transmitted to a room or mobile-phone for private storage, with the original reference information deleted from the system. Biologic information gotten upon authentication is transmitted through wireless system to the room or mobile-phone for comparison with the reference, the result being returned to the system. Or, the reference is tentatively sent back to the system for comparison with the gotten biologic information. The biologic information sent to mobile-phone also includes health control information for storage and display. Mobile-phone also can receive blood pressure information at a waiting lounge of medical institution though wireless local communication even if the main power shut down. The communication between the biometrics system and the mobile-phone is encrypted. The system includes sensor unit and protection unit, the abnormality thereof being separately checked.

16 Claims, 22 Drawing Sheets

US 10,803,156 B2
Page 2

Related U.S. Application Data continuation of application No. 11/627,962, filed on Jan. 27, 2007, now Pat. No. 8,224,034.

(51) Int. Cl.
| | |
|---|---|
| *G16H 10/60* | (2018.01) |
| *G07C 9/25* | (2020.01) |
| *G06F 19/00* | (2018.01) |
| *G06Q 20/40* | (2012.01) |
| *A61B 5/117* | (2016.01) |
| *A61B 5/021* | (2006.01) |
| *A61B 5/1455* | (2006.01) |
| *A61B 5/00* | (2006.01) |
| *G16H 50/20* | (2018.01) |

(52) U.S. Cl.
CPC ......... *G06K 9/00906* (2013.01); *G06Q 20/40* (2013.01); *G07C 9/257* (2020.01); *G16H 10/60* (2018.01); *A61B 5/002* (2013.01); *A61B 5/021* (2013.01); *A61B 5/1455* (2013.01); *A61B 2560/0242* (2013.01); *G06K 2009/00932* (2013.01); *G16H 50/20* (2018.01)

(58) Field of Classification Search
CPC ........ G06Q 50/24; G06Q 20/40; G07C 9/257; G16H 10/60; G16H 50/20; G06K 9/00906; G06K 2009/00932; A61B 5/117; A61B 5/002; A61B 5/1455; A61B 5/021; A61B 2560/00242
USPC ......................................................... 705/2, 3
See application file for complete search history.

(56) References Cited

U.S. PATENT DOCUMENTS

| | | | | |
|---|---|---|---|---|
| 2002/0032039 A1* | 3/2002 | Kimata | ................... | G01S 19/21 455/556.1 |
| 2002/0077557 A1* | 6/2002 | Cheng | ................... | A61B 5/021 600/490 |
| 2002/0087664 A1* | 7/2002 | Birkhoelzer | ........ | G06F 19/3418 709/219 |
| 2002/0097142 A1* | 7/2002 | Janiak | ................ | G06K 9/00006 340/5.53 |
| 2002/0169584 A1* | 11/2002 | Fu | .......................... | A61B 5/747 702/188 |
| 2002/0170565 A1* | 11/2002 | Walker | ................... | G06Q 50/24 702/19 |
| 2002/0188472 A1* | 12/2002 | Fujisaka | ............ | G06F 21/6245 705/2 |
| 2003/0115490 A1* | 6/2003 | Russo | ................... | H04L 9/3231 726/5 |
| 2003/0119527 A1* | 6/2003 | Labun | .................... | H04L 67/04 455/456.1 |
| 2004/0076177 A1* | 4/2004 | Koch | ................ | H04W 52/0235 370/465 |
| 2004/0093167 A1* | 5/2004 | Braig | ..................... | G16H 40/40 702/23 |
| 2004/0233930 A1* | 11/2004 | Colby, Jr. | ........... | H04L 63/0853 370/464 |
| 2005/0277872 A1* | 12/2005 | Colby, Jr. | ............ | A61B 5/7475 604/67 |
| 2005/0288584 A1* | 12/2005 | McMorrow | ............ | A61B 8/565 600/437 |
| 2006/0041450 A1* | 2/2006 | Dugan | ................... | G06Q 10/10 705/2 |
| 2006/0058626 A1* | 3/2006 | Weiss | ..................... | G16H 80/00 600/407 |
| 2006/0089174 A1* | 4/2006 | Twerdahl | .............. | G06F 1/1698 455/567 |
| 2006/0154642 A1* | 7/2006 | Scannell, Jr. | .......... | G16H 10/60 455/404.1 |
| 2006/0247505 A1* | 11/2006 | Siddiqui | .............. | A61B 5/0024 600/300 |
| 2006/0282395 A1* | 12/2006 | Leibowitz | ............ | G06Q 20/425 705/67 |
| 2007/0047770 A1* | 3/2007 | Swope | ............... | G06K 9/00926 382/115 |
| 2007/0253021 A1* | 11/2007 | Mehta | .................. | A61B 5/0002 358/1.15 |
| 2010/0286488 A1* | 11/2010 | Cohen | ................... | G16H 10/65 600/300 |
| 2012/0143070 A1* | 6/2012 | Yao | ........................ | G16H 10/60 600/490 |

* cited by examiner

BIOMETRICS SYSTEM, BIOLOGIC INFORMATION STORAGE, AND PORTABLE DEVICE

CROSS REFERENCE TO RELATED APPLICATION

This application is a Continuation application of U.S. application Ser. No. 13/549,420 filed Jul. 14, 2012, which is a continuation application of U.S. application Ser. No. 11/627,962 filed Jan. 27, 2007, herein incorporated by reference in its entirety.

BACKGROUND OF THE INVENTION

1. Field of the Invention

This invention relates to a biometrics system for authenticating a person on the basis of biologic information. This invention also relates to a biologic information storage and to a portable device such as a mobile-phone.

2. Description of the Related Art

In this field of the art, various biometrics systems have been proposed for blocking an imposter upon authentication, or for realizing an easy authentication. On the other hand, Japanese Laid-open Patent Application 2004-344375 proposes to make use of biologic information obtained for the purpose of authenticating a person to also look after health of the person.

Since biologic information is important private information, however, authentication with biologic information may cause problems of privacy violation.

SUMMARY OF THE INVENTION

The object of this invention is to provide a biometrics system in which security in authentication is enhanced with privacy protection carefully considered.

Another object of this invention is to provide a biologic information storage for storing biologic information for authentication or for health control.

Further object of this invention is to provide a portable device such as a mobile-phone useful for biometrics or health control.

To achieve one of the above objects, this invention provides a biometrics system for attaining an object, such as an entrance unlocking or a bank account authentication, by means of authenticating a person through a comparison between biologic information gotten by the person and registered reference biologic information of the person. The biometrics system comprising an administrator arranged to administrate the registration of the reference biologic information of the person and a transmitter, such as a wireless local communication apparatus, arranged to transmit the registered reference biologic information to an outside device under private control by the person to have the outside device store the registered reference biologic information.

According to the above feature of this invention, the reference biologic information is prevented from being forged since the registration of the reference biologic information is only possible under administration of the biometrics system. On the other hand, the reference biologic information once registered is transmitted to an outside device, such as a biologic information storage or a portable device, which is under private control by the person to keep privacy of the registered reference biologic information.

The biometrics system according to a detailed feature of this invention above further comprises a controller arranged to delete the registered reference biologic information from the biometrics system after the transmission of the registered reference biologic information to the outside device. Thus, the privacy protection is strengthened.

The biometrics system according to another detailed feature of this invention above further comprises a second transmitter arranged to transmit to the outside device a biologic information gotten from a person, a receiver arranged to receive a result of comparison between the transmitted biologic information and the registered reference biologic information from the outside device, and function part arranged to attain the object in accordance with the result of comparison received by the receiver. Thus, there is no necessity for the biometrics system to keep the reference biologic information, which is advantageous for privacy protection.

In the case that the biometrics system according to this invention above is applied to a lock control system for an entrance door commonly utilized by a plurality of persons, the outside device is under individual control of one of the persons utilizing the entrance.

In the case that the biometrics system according to this invention above is applied to a bank system for authenticating a customer of the bank, on the other hand, the outside device may be a portable device, such as a mobile-phone, carried by the customer.

The biometrics system according to a different type of detailed feature of this invention above further comprises a receiver arranged to temporarily receive the registered reference biologic information from the outside device every time when needed, a comparator arranged to compare a biologic information gotten from a person and the registered reference biologic information, and function part arranged to attain the object in accordance with the result of comparison by the comparator. In this case, the outside device has no need of being informed of biologic information gotten from a person upon authentication, nor has any comparison function by itself, but simply keeps the reference biologic information. The biometrics system, on the other hand, does not permanently keep the reference biologic information in consideration of privacy protection.

This invention also provides a biometrics system for attaining an object by means of authenticating a person through a comparison between biologic information gotten by the person and registered reference biologic information of the person, which comprises a biologic information sensor arranged to sense biologic information including biometrics information and health control information, and a transmitter, such as a wireless local communication apparatus, arranged to transmit the biologic information sensed by the sensor to an outside device to have the outside device store the biologic information as the health control information.

According to the above feature of this invention, the biologic information of a person is sent to the outside device every time without fail when the authentication of the person is made. In other words, the outside device stores the health control information in natural response to the authentication. Thus, the outside device can easily and regularly accumulate the health control information of the person even if the outside device by itself has no biologic information sensor, which is sometimes of high performance requiring high cost for a high reliability of authentication. For example, the outside device is under control of a medical institution for a sophisticated health care. Or, the outside device is a portable device under private control by the person, such as a mobile-phone.

According to the detail of the feature of this invention above, the level of sufficiency of the biologic information may differ between a case for authentication by the biometrics system and a case for storage by the outside device. For example, this makes it possible for the biometrics system to complete the authentication even if the level of the biologic information is insufficient for the purpose of the storage by the outside device.

According to the detail of the feature of this invention above, the transmitter is arranged to transmit the biologic information to the outside device when the biometrics system succeeds in authenticating the person on the basis of the biologic information sensed by the sensor. In more detail, the transmitter may be arranged to transmit the biologic information to the outside device under private control by the person authenticated through the biologic information.

This invention also provides a biologic information storage for storing a reference biologic information for use in a biometrics system of attaining an object by means of authenticating a person through a comparison between biologic information gotten from the person and the reference biologic information of the person. The biologic information storage comprises a receiver arranged to receive the reference biologic information from the biometrics system, a storage part arranged to store the received reference biologic information, and a communicator arranged to communicate with the biometrics system for utilizing the reference information upon authentication. The biologic information storage corresponds to the outside device explained above, the various details and advantages of which are not necessary to be repeated.

This invention also provides a portable device, such as a mobile-phone, for storing health control information of a person carrying the potable device comprising a receiver, such as a wireless local communication apparatus, arranged to receive the health control information from an outside biologic information sensor, a storage part arranged to store the received health control information, and a display arranged to display health control information on the basis of the storage part.

According to the above feature of this invention, the portable device can easily accumulate the health control information of a person carrying the portable device for display on it even if the portable device by itself has no biologic information sensor, which is sometimes of high performance requiring high cost. For example, a mobile-phone according to the invention above can receive and store blood pressure information from a high performance of automatic blood pressure monitor located at a waiting lounge of medical institution if such a blood pressure monitor has a suitable information transmitter, such as a wireless local communication apparatus.

According to the detail of the feature of this invention above, the wireless local communication apparatus is activated even if the mobile-phone communication apparatus is deactivated. Thus, the mobile-phone can receive the health control information from the outside biologic information sensor, such as the automatic blood pressure monitor, even if the main power switch of the mobile-phone is shut down in compliance with the instruction of medical institution.

This invention also provides a biometrics system for attaining an object by means of authenticating a person through a comparison between biologic information gotten by the person and registered reference biologic information of the person, which comprises an encryption system, an administrator arranged to administrate the registration of the reference biologic information of the person with the encryption system utilized, the encrypted reference biologic information being stored by an outside device, a biologic information sensor arranged to sense biologic information of the person to be authenticated, and a transmitter arranged to transmit to the outside device the biologic information sensed by the sensor with the encryption system utilized, whereby the encrypted biologic information gotten form the person and the encrypted reference biologic information are compared at the outside device.

According to the above feature of this invention, various advantages are attainable by means of the combination of the biometrics and the encryption system. Firstly, an imposter upon authentication is blocked by means of the biometrics system. Secondly, various signals exchanged between the biometrics system and the outside device through a wireless local communication apparatus or the like are prevented from being forged by means of the encryption system. Thirdly, a possible outflow of the reference biologic information through the biometrics system is prevented by means of the encryption system.

This invention also provides a biometrics system for attaining an object by means of authenticating a person through a comparison between biologic information gotten by the person and registered reference biologic information of the person, which comprises a biologic information sensor unit arranged to sense biologic information of the person, a protection unit separable from the biologic information sensor unit arranged to prevent the biologic information sensor unit from being damaged, and a controller arranged to separately check the biologic information sensor unit and protection unit, respectively, for detecting abnormal condition thereof.

According to the above feature of this invention, the biologic information sensor unit of a sensitive nature is prevented from being damaged by means of the separable protection unit, the abnormal condition of both the units being separately checked. Thus, the protection unit if vandalized or tainted can be promptly detected for replacement thereof, and the biologic information sensor unit if out of order by itself can be distinctly detected. Roller 53 checks whether or not sensor unit 51 is working correctly.

Other features and advantages according to this invention will be readily understood from the detailed description of the preferred embodiments in conjunction with the accompanying drawings.

DETAILED DESCRIPTION OF THE PREFERRED EMBODIMENTS

First Embodiment

Figure 1:
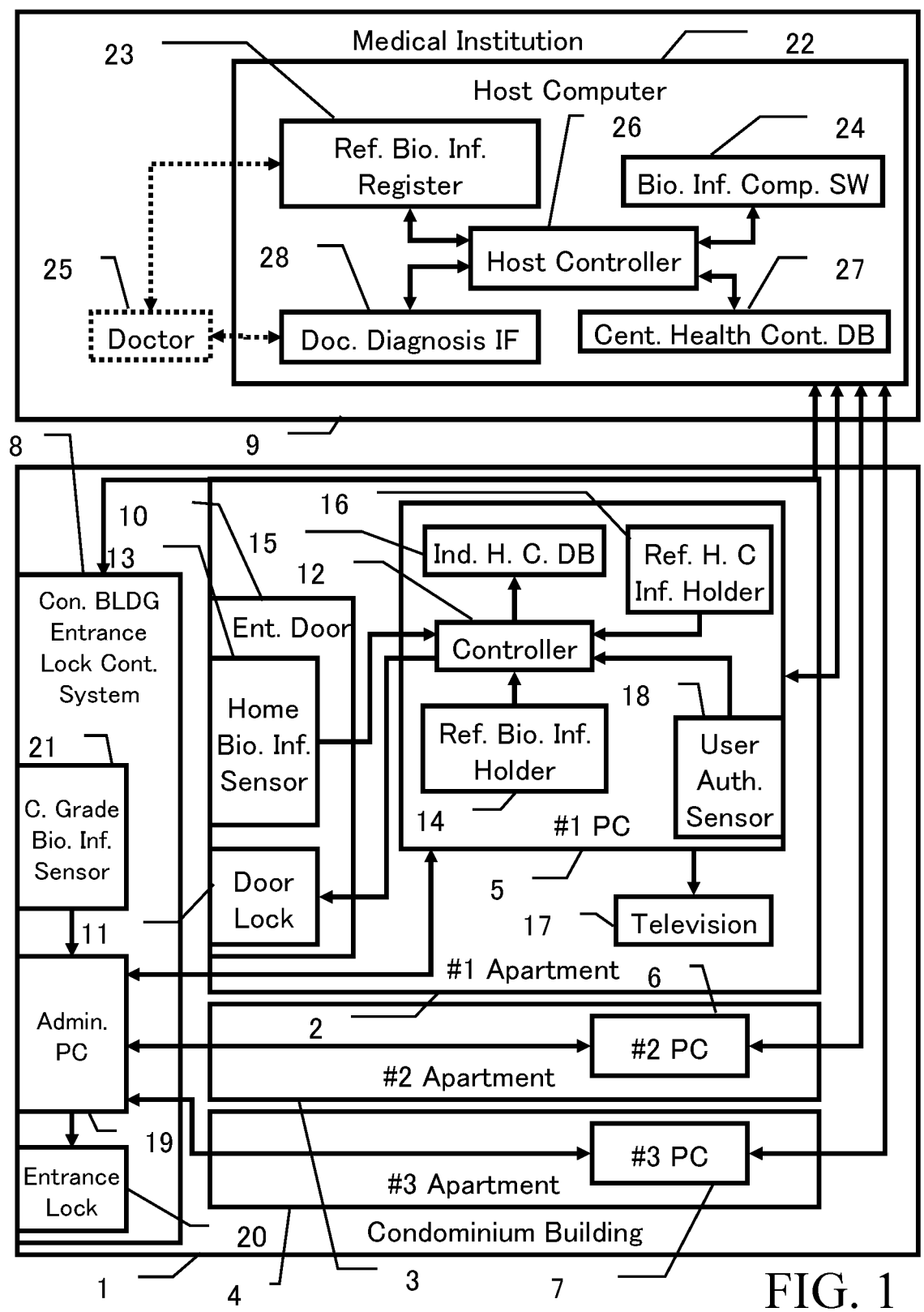
FIG. 1 is a block diagram of a biometrics and health controlling system according to a first embodiment of this invention.

FIG. 1 is a block diagram of a biometrics and health controlling system according to a first embodiment of this invention, which is embodied in a condominium building where a plurality of families domicile.

Condominium building 1 in FIG. 1 includes the first apartment 2 for the first family, the second apartment 3 for the second family and the third apartment 4 for the third family with rest apartments in fact included in condominium building 1 omitted for simplification of the figure. The first personal computer 5 controls the entire system in the first apartment 2, the detailed structure of which will be explained later. The second apartment 3 and the third apartment 4 each are of the same structure, which is not shown except for the second personal computer 6 and the third personal computer 7 for controlling the entire systems of the apartments, respectively. Detailed explanation of these apartments is also omitted for avoiding duplication.

According to the system of the first embodiment, each of apartments 2, 3 and 4 is in cooperation with condominium building entrance lock control system 8 and with medical institution 9, the details of which will be explained later.

A personal computer such as the first personal computer 5 is hereinafter explained as a controller in the apartment. In place of such a general-purpose personal computer, however, an exclusive use computer for the system may be provided for the apartment in practicing this invention. Further, adoption of any other controlling means is possible if it has the similar function.

Entrance door 10 of the first apartment 2 is provided with door lock 11 that automatically locks entrance door 10 upon every closure thereof. The first personal computer 5 controls whether or not to unlock entrance door 10 from the outside. For this purpose, controller 12 of the first personal computer 5 receives biologic information of a person, who is going to unlock entrance door 10, from home biologic information sensor 13 to compare the received information with a reference biologic information previously registered in reference biologic information holder 14. In response to the comparison, the first personal computer 5 sends unlock signal to door lock 11 if the person is authenticated as one who is entitled to enter the first apartment 5.

In more detail, home biologic information sensor 13 includes a blood vessel sensor for optically detecting information of blood vessel inside a human finger inserted into a predetermined position. Controller 12 receives blood information from the blood vessel sensor for extracting a pattern of blood vessel to determine whether it is identical with one of reference blood vessel patterns of previously registered family members in reference biologic information holder 14. And, the first personal computer 5 sends unlock signal to door lock 11 if the extracted blood pattern is identical with the one of the family members entitled to enter the apartment 4.

The information of the finger blood vessel sensed by home biologic information sensor 13 includes not only blood vessel pattern information, but also plethysmogram information due to artery pulsation in the human finger. Controller 12 gets from plethysmogram information the blood component information such as oxygen saturation or information of blood vessel youth, for example. Since such information as blood component and blood vessel youth is useful for individual health control, controller 12 sends it to individual health control database 15 for storage therein with respect to every parson authenticated.

Controller 12 compares the blood component information or blood vessel youth information with reference information individually stored in reference health information holder 16. Reference health information holder 16 holds not only instantaneous value of the reference information but also change in it over time. Thus, controller 12 not only compares instantaneous value of the information sensed by home biologic information sensor 13 with the instantaneous value of the reference information held by reference health information holder 16. But also, controller 12 compares the change in information sensed by home biologic information sensor 13 and stored in individual health control database 15 with the reference change information held in health information holder 16. Thus, the health control is possible also in view of the speed of the change in information sensed by home biologic information sensor 13 over time. The results of comparison between the instantaneous values of information and of the comparison between the changes in information are displayed on the monitor of television set 17. In case of such a display on the monitor of television set 17, it is advantageous to make such an indication as "ABNORMALITY" automatically follow the turning on of the television set 17 in dependence of the result of the comparison showing the abnormality.

In displaying the results of comparison, a person even in a family may expect his or her privacy to be respected. For such privacy, in place of the television set 17, a mobile-phone kept by each person in the family may be used to receive the results of the comparison. Thus, each person is capable of confirming personal health by watching the display of own mobile-phone on every entry into the apartment. An application of this invention to a mobile-phone will be explained later in more detail with respect to the second embodiment.

As in the above, home biologic information sensor 13 according to the invention has dual functions of authenticating a person for unlocking the door and of getting information of health control of the same person. Therefore, first personal computer 5 normally sends the unlock signal to door lock 11 when succeeding in both authenticating a person and getting the health control information of the person.

First personal computer 5 also sends the unlock signal to door lock 11 when succeeding in authenticating a person even if failing in getting sufficient health control information of the person. This is because the entry control, which is the primary object, is attained when the person authentication has been successfully completed for the purpose of unlocking the door. However, the person under authentication for unlocking the door expects that the health control information is gotten at the same time. Therefore, in the case of failing in getting health control information, a caution is made to inform the person of the failure and its reason. At hearing or watching such a caution, the person may again insert his or her finger into home biologic information sensor 13 if the person prefers to try again to get health control information. Or, the person may promptly enter the first apartment 2 with the reason of the failure in mind for improving the manner of inserting his or her finger for the next time.

As home biologic information sensor 13, a funduscopic sensor for examining the eye-fundus image is applicable in place of the blood vessel sensor for optically detecting information of blood vessel. The eye-fundus image, which also includes both retina pattern for authentication and health control information, can serves as the sensor according to this invention as in the case of blood vessel image. A voice sensor for examining the vocal print, which also capable of getting both authentication and health control information, is still another example of home biologic information sensor 13 of this invention. In the case of checking the voice, it is possible to add a breath component sensor for breath alcohol testing in combination with the voice sensor, which can check the correlation between drinking and the health.

Any type of sensor other than the types mentioned above is possible to be used in this invention as home biologic information sensor 13 provided that such a type is capable of both authenticating a person and getting health controlling information of the person. For example, not only the above mentioned noncontact type sensors but also a contact type sensor for the skin is applicable. Further, not only sensors detecting light or sound, but also an electric sensing system for passing a weak electric current through living body to probe a response signal. In place of selecting a suitable single type of sensor, a plurality of different types of sensors can be combined for improving degree of accuracy as well as increasing a variety of health control information.

Further, not only the case of combining sensors each capable of both the authentication and the health controlling information getting, but also a case is possible in which one of such dual function sensors in combined with a single function sensor capable of only authentication or health controlling information getting. For example, an image sensor for processing the image to interpret body temperature may be combined with one of the dual function sensors. Or a finger pattern sensor for authentication may be combined with one of the dual function sensors.

Home biologic information sensor 13 is satisfactory if it has the dual function as a whole. In other word, home biologic information sensor 13 does not necessarily require a sensor with the dual function, but a combination of a sensor with only authentication function and another sensor with only health controlling information getting function is satisfactory. Further, the point of this invention is to automatically get health controlling information upon authentication. So, not only biometrics system, but also a conventional authenticating system such as password system or IC card system can be adopted in this invention with suitable measures taken for naturally getting health controlling information upon authentication by such a conventional system.

The first personal computer 5 further includes user authentication sensor 18 for authenticating a user who is entitled to access the first personal computer 5. User authentication sensor 18 includes the biometrics system capable of getting finger blood vessel information as has been explained in the case of home biologic information sensor 13. User authentication sensor 18 further includes a sensor typical of a personal computer such as a sensor arranged at the mouse of the first personal computer 5 for getting blood vessel pattern of a palm grasping the mouse. Such a palm blood vessel sensor at the mouse can perform the biometrics check not only at the initial access to the first personal computer 5, but also the sensor can repeat it during operation of the first personal computer 5 by the user. In other words, it is possible to continuously monitor health control information of the user throughout the entire period of using the first personal computer 5. Thus, this invention in also applicable to a case of authenticating the user who is entitled to access a personal computer.

Procession of the signal from user authentication sensor 18 and comparison of the sensor signal with the reference signal registered in reference biologic information holder 14 for authentication are similar to those explained with respect to home biologic information sensor 13. Further, comparison of the sensor signal with the reference signal registered in reference health information holder 16 for health control and storage of the sensor signal into in individual health control database 15 are also similar to those explained with respect to home biologic information sensor 13. Further explanation on user authentication sensor 18 is accordingly omitted for avoiding duplication, except for the following comment. Namely, it is typical to the case of user authentication sensor 18 that controller 12 allows a user to access to the first personal computer 5 when the user is authenticated as a result of the comparison of the signal from user authentication sensor 18 with the reference signal registered in reference biologic information holder 14.

In addition to the above described authentication for unlocking door lock 11 of entrance door 10 and for accessing the first personal computer 5, the first personal computer 5 has a function of communicating with administration computer 19, which is a personal computer located in condominium building entrance lock control system 8 of condominium building 1 to control the same in the first embodiment.

Condominium building entrance lock control system 8 includes entrance lock 20, which is automatically locked every after the entrance is closed. The unlocking of the entrance from the outside is made possible under control of administration computer 19. Condominium building entrance lock control system 8 includes commercial grade biologic information sensor 21 for authenticating a person who wants to enter the entrance of condominium building 1. Commercial grade biologic information sensor 21 sends the sensed information of the person to administration computer 19, which in turn sends the received information to every personal computer of the apartment which joins condominium building entrance lock control system 8. In the case of FIG. 1, the information sensed by commercial grade biologic information sensor 21 is received by administration computer 19, and is in turn sent to the first personal computer 5 of the first apartment 2, to the second personal computer 6 of the second apartment 3 and to the third personal computer 7 of the third apartment. Further, if there are other personal computers of other apartments which each join condominium building entrance lock control system 8, administration computer 19 also send the received information to such personal computers. Commercial grade biologic information sensor 21 not only has the same function as of home biologic information sensor 13, but also has other high grade additional sensing functions.

Under the situation above, the first personal computer 5 of the first apartment 2 compares the information sensed by commercial grade biologic information sensor 21 with the reference information registered in reference biologic information holder 14. As a result of such a comparison, if the first personal computer 5 authenticates that the person at the entrance is entitled to enter the condominium building 1, the first computer 5 inform administration computer 19 of the result. In response to such an authentication by the first personal computer 5, administration computer 19 sends an unlock signal to entrance lock 20. On the other hand, if the information from administration computer 19 fails to coincide with the reference at the first personal computer 5, it informs administration computer 19 of such a result of failure. In this case, administration computer 19 is not caused to send any unlock signal to entrance lock 20 by at least the first personal computer 5.

The similar cooperation is made between administration computer 19 and other every personal computer of apartment that joins condominium building entrance lock control system 8, such as the second personal computer 6 of the second apartment 3 and the third personal computer 7 of the third apartment or the like. Administration computer 19 sends an unlock signal to entrance lock 20 if informed of a successful authentication by at least one personal computer. On the other hand, if all the personal computers inform administration computer 19 of the failure in coincidence of the sensed information with the reference, administration computer 19 does not send any unlock signal to entrance lock 20 at all. Instead, administration computer 19 causes an admission refusal indication at the entrance.

Even in a case of no response from some of apartments, administration computer 19 does not send any unlock signal to entrance lock 20 if all of the rest of the apartments inform administration computer 19 of the failure in coincidence of the sensed information with the reference. In this case, administration computer 19 also causes an admission refusal indication at the entrance. If a person really entitled to enter condominium building 1 requires the authentication and faces to such an admission refusal indication, the person can know that something is wrong with the system relating to the apartment he or she is going to reach. Then, he or she may enter condominium building 1 by unlocking entrance lock 20 with an auxiliary conventional authentication system, such as password system or IC card system for the time being. The person is also informed of the necessity of system recovery by the admission refusal indication.

The admission refusal indication includes no information of the reason. In other words, no one other than the person entitled to enter condominium building 1 knows whether all the personal computers inform administration computer 19 of the failure in coincidence of the sensed information with the reference or something is wrong with the system relating to the apartment he or she is going to reach. Further, even administration computer 19 cannot identify individual apartment which sends its response, but can only determine whether or not one of the apartments informs administration computer 19 of the coincidence of the sensed information with the reference. Thus, privacy relating to the reference information of each apartment is kept.

As is apparent from the above, administration computer 19 of condominium building entrance lock control system 8 itself has no function of storing private reference information of person in each apartment or comparing the sensed information with the private reference information, but has the function of only receiving the result of the comparison reported from each apartment. By this consideration, the reference information relating to privacy such as the blood vessel pattern or the eye-fundus pattern is kept within the apartment. Further, administration computer 19 having no function of comparison of the information nor knowing the origin of the comparison result cannot identify the person whose information is sensed by commercial grade biologic information sensor 21. Thus, privacy of the person who wants to enter condominium building is kept.

Commercial grade biologic information sensor 21 as well as home biologic information sensor 13 can get not only the information of authentication but also the information of health control. Therefore, commercial grade biologic information sensor 21 can performs the same health control function as in home biologic information sensor 13 explained above. The manner of processing the signal from commercial grade biologic information sensor 21, the comparison of the signal from commercial grade biologic information sensor 21 with reference information registered in reference health information holder 16, and the storage of the health control information in individual health control database 15 are similar to the corresponding functions explained in relation to home biologic information sensor 13. So, further explanation is omitted.

As has been mentioned above, commercial grade biologic information sensor 21 is of common functions to those in home biologic information sensor 13 with higher functions added. Reference biologic information holder 14, reference health information holder 16 and individual health control database 15 are prepared for such higher functions of commercial grade biologic information sensor 21.

The functions of commercial grade biologic information sensor 21 in common with home biologic information sensor 13 are useful for double checking the same health control information. For example, commercial grade biologic information sensor 21 at the entrance of condominium building 1 initially gets health control information of a person who is going to the first apartment 2, and home biologic information sensor 13 at entrance door 10 gets the same health control information of the same person again. Thus, the reliability of the gotten health control information is improved.

Further, the correlation between the same health control information gotten at the entrance of condominium building 1 and at entrance door 10. For example, if the health control information is gotten at the entrance of condominium building 1 with the person in normal condition and the same health control information is gotten at entrance door 10 with the same person reaching there by stairs, the correlation of the health control information between the normal condition and a condition under exercise stress can be checked. The degree of exercise stress can be taken in through checking pulsation.

On the other hand, if a person walking uphill to reach the entrance of condominium building 1, the health control information of the person suffering the exercise stress is gotten by commercial grade biologic information sensor 21. And, if the person recovering to the normal condition by using an elevator up to his or her apartment, home biologic information sensor 13 can get the same health control information for diagnosing the resilience.

Thus, the combination of the health control information gotten at the entrance of condominium building 1 and at entrance door 10 with lifestyle of inhabitant of condominium building 1 naturally taken into consideration makes it possible to gather fruitful health control information data.

Health condition is apt to be influenced by climate conditions such as season, temperature, humidity, and wind velocity. Therefore, home biologic information sensor 13 and commercial grade biologic information sensor 21 each have functions of recording date and time as well as sensors for such climate conditions to get further fruitful health information data. Especially, commercial grade biologic information sensor 21, which is located at the entrance of condominium building in an outdoor, is suitable to get such climate conditions. Further, temperature and humidity sensed by commercial grade biologic information sensor 21 outside condominium building 1 differ from those sensed by home biologic information sensor 13 within condominium building 1. This makes it possible to compare the same health control information item gotten under different temperature and humidity.

As has been explained, the cooperation between the first apartment 2 and condominium building entrance lock control system 8 has to be similarly done between the second apartment 3 and condominium building entrance lock control system 8 and between the third apartment 4 and condominium building entrance lock control system 8 or the like. So, the system in each apartment is administrated in accordance with the common standard within the condominium building. And, the system in each apartment is checked upon moving in of a new inhabitant. Further, if the version of condominium building entrance lock control system 8 is upgraded, the systems of all th apartment in condominium building 1 are correspondingly upgraded into the new version.

If an inhabitant moves out condominium building 1, the contents of reference biologic information holder 14, individual health control database 15 and reference health information holder 16 are desired to be carried over into a new residence, though unlocking information peculiar to the old residence should be abandoned. Therefore, at least the health control system using the contents of reference biologic information holder 14, individual health control database 15 and reference health information holder 16 are administrated on a universal standard.

The explanation is advanced to the cooperation between medical institution 9 and the apartment in condominium building 1. The first personal computer 5 of the first apartment 2, for example, is in communication with host computer 22 of medical institution 9 for exchanging information. For the purpose of keeping security, the information is exchanged in cipher and the authentication of the patient in medical institution 9 is carefully done by means of the biometrics system utilizing user authentication sensor 18 of the first personal computer 5.

Reference health information in reference health information holder 16 of the first personal computer 5 is registered at reference biologic information register 23 of host computer 22 when the inhabitant of condominium building 1 visits medical institution 9. In other words, the inhabitant visiting medical institution 9 as a patient consults with an automatic diagnostic system for self-testing his or her health control information in accordance with the instruction given by biologic information comparing software 24 to automatically register the result as the reference health information. The diagnosis may be different from each other even if the value of the health control information itself is the same. So, doctor 25 further gives a face-to-face diagnosis to modify the automatically gotten reference health control information if necessary. In this case, the doctor-modified reference health control information is marked to be distinguished from the automatically gotten reference health control information for taking it into consideration upon comparison with the sensed information.

Thus registered reference health control information of the patient is sent to the first personal computer 5 under administration by host controller 26 to be stored into reference health information holder 16. Further a pert of biologic information comparing software 24 necessary for the first personal computer 5 to handling the reference health control information is sent to the first personal computer 5 to be installed into controller 12.

Information gotten by home biologic information sensor 13, commercial grade biologic information sensor 21 and user authentication sensor 18 as they are, as well as those stored in individual health control database 15, are sent from the first personal computer 5 to host computer 22 in real time to be stored into central health control database 27.

Also, the result of comparison between the sensed information and the reference in reference health information holder 16 is sent from the first personal computer 5 to host computer 22 as supplemental information. Though the comparison between the sensed information and the reference is possible at host computer 22 under control of biologic information comparing software 24, it is helpful for host computer 22 to be informed of the result of comparison done by the first personal computer 5. A comparison of high level health control information is, of course, conducted by host computer 22 exclusively on the basis of the sensed information sent from the first personal computer 5 under control of biologic information comparing software 24. Such comparison result is also stored into central health control database 27.

The sensed health control information or the result of the comparison of it with the reference with respect to every patient stored in central health control database 27 is outputted on a regular schedule at doctor diagnosis interface 28 available to doctor 25. Doctor 25 inputs his or her diagnosis at doctor diagnosis interface 28 for storage into central health control database 27

The comparison result automatically made by biologic information comparing software 24 or diagnosis made by doctor 25 is sent on a regular schedule to the first personal computer 5, which can be viewed on a monitor of the first personal computer 5 of television set 17.

If the result by biologic information comparing software 24 or diagnosis by doctor 25 indicates an emergency, an alert is generated in a prompt manner from host computer 22 for informing the first personal computer 5 of it.

The above mentioned cooperation between medical institution 9 and the first apartment 2 is also made between medical institution 9 and each of other apartments such as the second apartment 3 or third apartment 4 in condominium building 1. For keeping such a total system, all the apartments in condominium building 1 is administrated in accordance with a common standard not only applicable to condominium building 1, but also to an entire system including medical institution 9.

Central health control database 27 of medical institution 9 stores health control information of variety of patients, which makes it possible to statistically process such health control information. This means that medical institution 9 can provide a specific patient with his or her position in view of the statistics, such as average or distribution. Further, medical institution 9 can decide in an evenhanded fashion whether health control information of a specific patient is within or out of a normal range of the average or distribution. Medical institution 9 makes a service of delivering such statistics information to the first personal computer 5 or the like. Of course, medical institution 9 highly keeps privacy of individual patients in handling the health control information in the statistics procession.

Biologic information comparing software 24 of medical institution 9 deeply relates to the information getting function of home biologic information sensor 13, commercial grade biologic information sensor 21 and user authentication sensor 18. So, if any of such sensors is replaced by new one with a changed or an improved function at condominium building 1, a corresponding maintenance of biologic information comparing software 24 should be done at medical institution 9. For this purpose, host computer 22 of medical institution 9 keeps contact with the first personal computer 5, the second personal computer 6 and the third personal computer or the like in each apartment as well as administration computer 19 of condominium building entrance lock control system 8 to mutually do necessary software maintenance.

On the other hand, medical institution 9 may propose an improved sensor for use in home biologic information sensor 13, or commercial grade biologic information sensor 21 or user authentication sensor 18 in accordance with a new service system that medical institution 9 is going to propose for its business. In this case, medical institution 9 provides such an improved sensor as well as driver software for such a sensor. Or, medical institution 9 provides an improved sensor and driver software thereof without extra charge every time when the service system is improved on a general maintenance agreement.

Because of movement or some other reason, a patient may change medical institution 9 into new one closer to the new residence or with other convenience. In this case, the patient may want his or her health control information stored in central health control database 27 to be taken over by the new medical institution. Therefore, health control information stored in central health control database 27 is handled in accordance with a common standard so that the health control information will be continuously valid even if the medical institution is changed.

Figure 2:
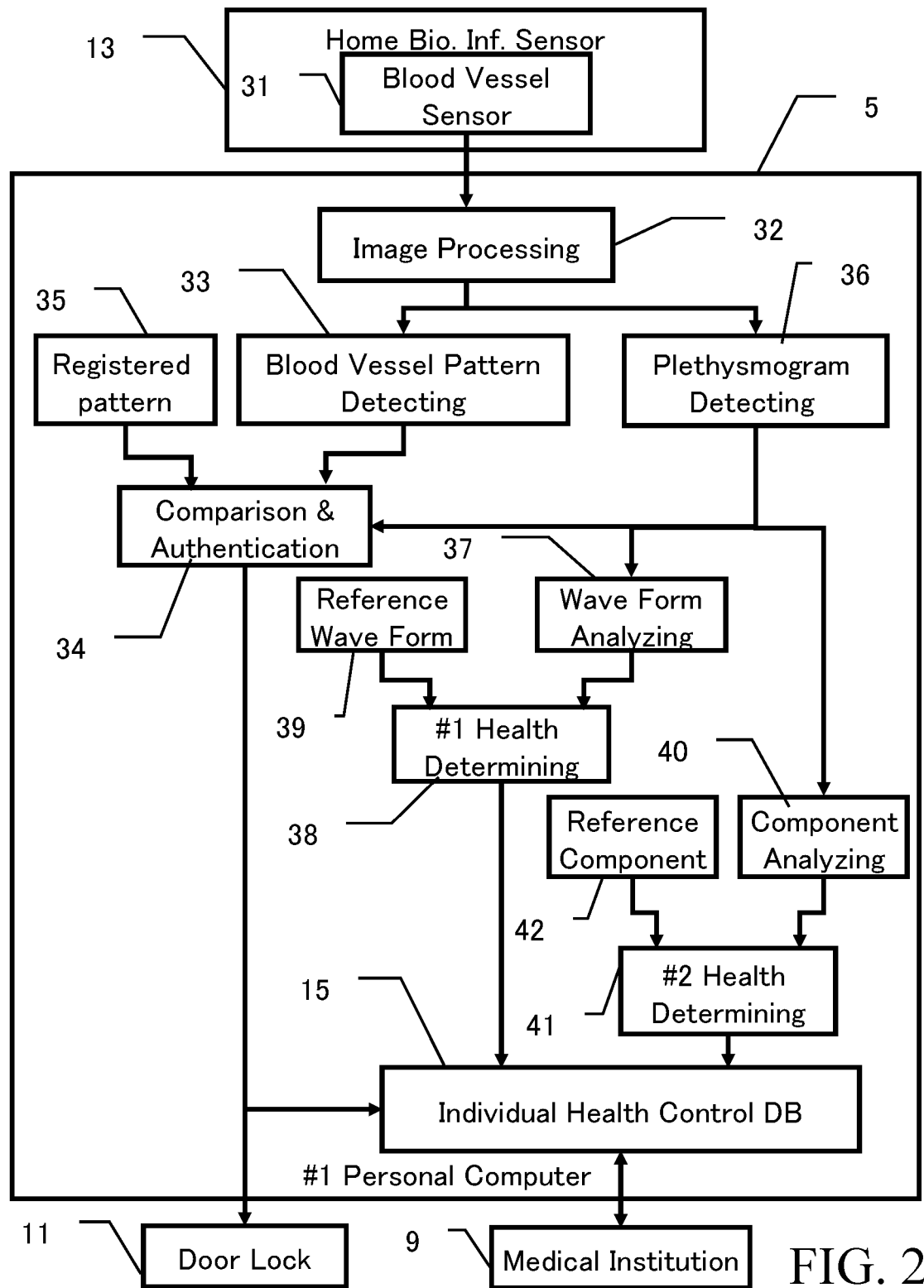
FIG. 2 is a block diagram of a blood vessel sensor system for the first embodiment.

FIG. 2 is a block diagram of a blood vessel sensor system for the first embodiment. The blood vessel sensor system such as in FIG. 2 is used as home biologic information sensor 13, commercial grade biologic information sensor 21 and user authentication sensor 18 for getting information for biometrics and health control. In FIG. 2, however, the blood vessel sensor system is specifically shown as home biologic information sensor 13 for example. The same numeral is used for identifying the same part throughout FIG. 1 and FIG. 2.

In FIG. 2, blood vessel sensor 31 is arranged in home biologic information sensor 13 into which a finger of a person requiring biometrics authentication is inserted. Blood vessel sensor 31 includes a plurality of light sources of different wavelength band having different light absorption characteristic by the blood and blood vessel and light receiving element for receiving the source light influenced by the blood and blood vessel. The output of blood vessel sensor 31 is sent to the first personal computer 5 and processed by image processing part 32 in controller 12. The functions of controller 12 are actually carried out by software. In FIG. 2, however, a function is shown as a hardware block such as "image processing part 31" for the purpose of explanation.

Of course, the functions are carried out actually by hardware blocks or a combination of hardware blocks and software.

Blood vessel pattern detecting part 33 detects blood vessel pattern inherent to individual from an image processed by image processing part 32. Comparison and authentication part 34 in controller 12 compares the detected blood vessel pattern with registered pattern 35 stored in reference biologic information holder 14 to decide whether the detected blood vessel pattern coincide with the registered blood vessel pattern. Thus, the authentication of the parson is made and controller 12 sends the unlock signal to door lock 11 if the identity is verified through the comparison.

The identification information form comparison and authentication part 34 is also sent to individual health control database 15 for administrating the gotten health control information under the name of individual.

Plethysmogram detecting part 36 in controller 12 detects plethysmogram of arteria on the basis of the image processed by image processing part 32. The detected plethysmogram is analyzed by wave form analyzing part 37 in controller 12. The first health determining part 38 compares the analyzed waveform with reference wave form 39 stored in reference biologic information holder 14 to diagnose the youth of blood vessel, which is in tern sent to individual health control database 15 for storage along with identification information from comparison and authentication part 34. The diagnosis on blood vessel youth by the first health determining part 38 is indicated on television set 17 as has been mentioned above.

Plethysmogram detected by plethysmogram detecting part 36 is also analyzed by component analyzing part 40 in controller 12 to determine arterial blood component such as a ratio of oxygenated hemoglobin to reduced hemoglobin which is a measure of oxygen saturation. The second health determining part 41 compares the analyzed component of arterial blood with reference component 42 stored in reference biologic information holder 14 to diagnose the arterial blood components, which is in tern sent to individual health control database 15 for storage along with identification information from comparison and authentication part 34. The diagnosis on arterial blood components by the second health determining part 41 is also indicated on television set 17.

The diagnosis result of the first health determining part 38 and the second health determining part 41, which have been once stored in individual health control database 15, are sent from controller 12 to medical institution 9. As has been explained, the diagnosis result gotten in real time by the first health determining part 38 and the second health determining part 41 are also sent to medical institution.

Plethysmogram detecting part 36 also informs comparison and authentication part 34 of the detected plethysmogram. Comparison and authentication part 34 will not make identification of a person for controller 12 to send the unlock signal to door lock 11 even if the blood vessel pattern detected by blood vessel pattern detecting part 33 coincides with the registered blood vessel pattern 35 stored in reference biologic information holder 14 unless the plethysmogram is actually transmitted from plethysmogram detecting part 36. This is to prevent entrance door 10 from being unlocked by a fake finger provided with a copied blood vessel pattern having no vital reaction.

Figure 3:
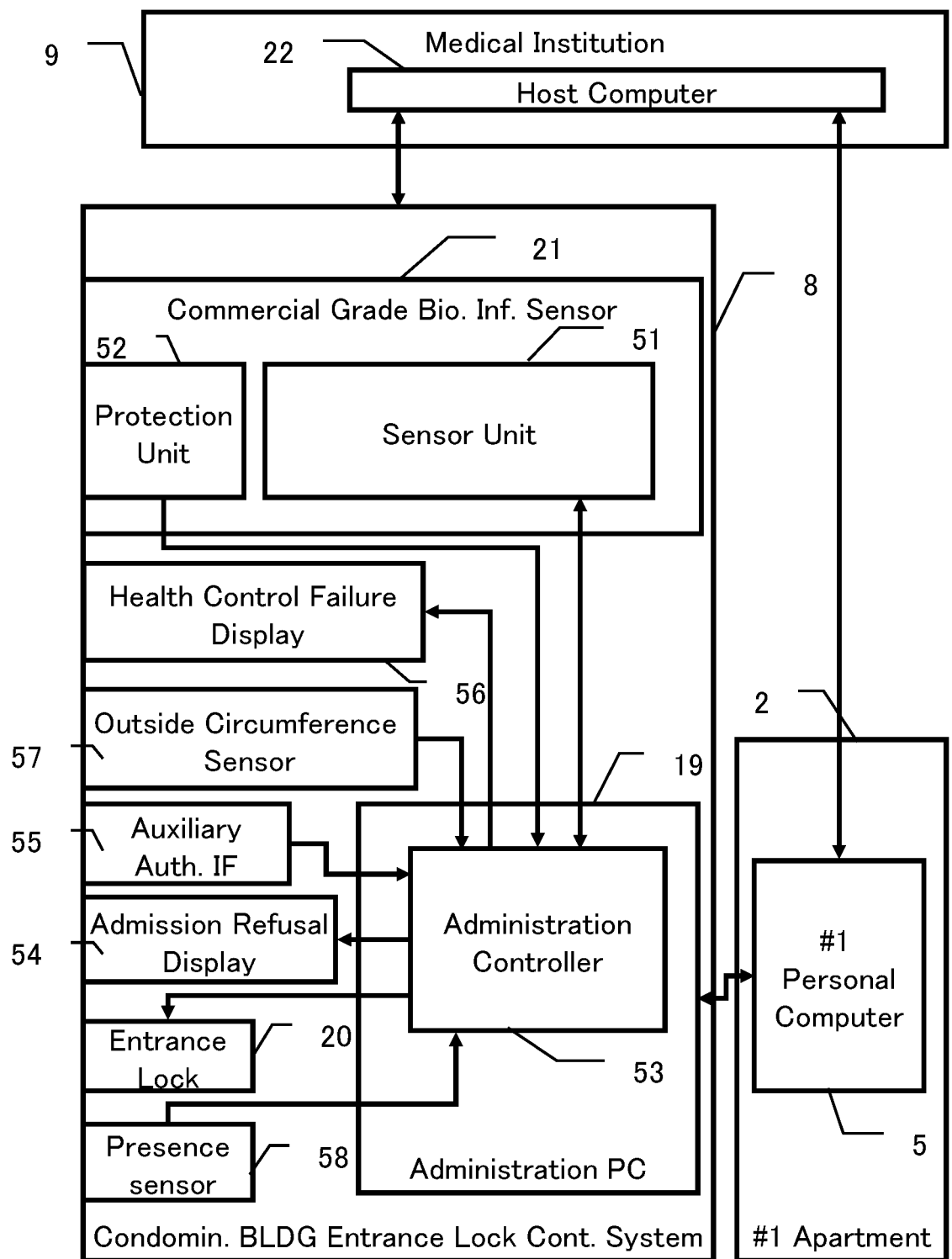
FIG. 3 is a block diagram representing the detailed structure of condominium building entrance lock control system for the first embodiment.

FIG. 3 is a block diagram representing the detailed structure of condominium building entrance lock control system 8. The same numeral is used for identifying the same part throughout FIG. 1 and FIG. 3 with explanation of the same numeral omitted unless additional comment is necessary.

Commercial grade biologic information sensor 21 includes replaceable units for allowing their exchange upon damaged. In other words, sensor unit 51 can be replaced by new one of the same or improved function with its outer shape and electric connector standardized for fitting into the casing of commercial grade biologic information sensor 21 even if inner function of sensor unit 51 is improved. Protection unit 52 such as a transparent cover to which the inserted finger or outside dust may contact is also replaceable by new one when tainted. Sensor unit 51 and protection unit 52 are replaceable independently from each other for making it possible to exchange only one of them in different occasion and by different reason.

Administration controller 53 of administration computer 19 is connected with sensor unit 51 for controlling its function and receiving the sensed signal from it. Further, administration controller 53 checks whether or not sensor unit 51 is working correctly.

Administration controller 53 of administration computer 19 is connected with protection unit 52 for checking whether or not vandalized or tainted. Thus, protection unit 52 which is exposed to outside environment is carefully monitored for prompt replacement thereof to keep proper function of commercial grade biologic information sensor 21.

The detection of damage or taint on protection unit 52 is alternatively possible by analyzing the output of sensor unit 53 without connecting administration controller 53 directly to protection unit 52. In other words, damage or taint on protection unit 52 can be indirectly known by detecting deterioration or the like of the output of sensor unit 51.

Further, administration controller 53 of administration computer 19 initially checks fluctuation in the function of sensor unit 51 or protection unit 52 when these are newly exchanged. In other words, administration controller 53 calibrates the performance of sensor unit 51 or protection unit 52 by testing whether sensor unit 51 outputs an expected level of signal under a given condition.

Admission refusal display 54 shows admission refusal indication if all the personal computers inform administration computer 19 of the failure in coincidence of compared information or none of the personal computers informs administration computer 19 of the coincidence. Auxiliary authentication interface 55 includes password input and IC card insertion slot for authenticating a person who cannot be identified through commercial grade biologic information sensor 21 but is really entitled to enter condominium building 1.

Health control failure display 56 shows that commercial grade biologic information sensor 21 cannot get sufficient health control information but has succeeded in authentication. By this display, a person who expects to check his or her health is informed of the failure in getting health control information. It is left to the person's judgment whether entering condominium building 1 without respect to the display or trying again to check health in more careful manner.

As is apparent from the above, health control failure display 56 serves as an indicator showing whether or not the authentication information is also a sufficient biologic information for the purpose of health control. The indication can be made by sound or voice instead of visual display.

The health control information gotten by condominium building entrance lock control system 8 does not relate to the entrance lock control itself, but absolutely to individual inhabitant in the apartment. Therefore, the necessity of indication at health control failure display 56 is to be judged exclusively by the first personal computer 5 in the first apartment 2 or the like, mere result being transmitted to condominium building entrance lock control system 8 for indication at health control failure display 56.

However, condominium building entrance lock control system 8 can judge whether or not the gotten biologic information is sufficient also for the purpose of health control if magnitude level of the output of commercial grade biologic information sensor 21 is measured. Thus, administration computer 19 may control whether or not to make indication at health control failure display 56. It may possible to finally control the indication of health control failure display 56 on both the judgments of administration computer 19 and the first personal computer 5.

Outside circumference sensor 57 is for sensing climate condition such as temperature, humidity and wind velocity. Administration controller 53 combines the climate condition information with the biologic information to send them to the first personal computer 5 as well as date and time of getting those information.

Presence sensor 58 detects an approach of a person within a predetermined area for automatically triggering commercial grade biologic information sensor 21 to start its function.

The structure of commercial grade biologic information sensor 21 including sensor unit 51 and protection unit of replaceable nature in FIG. 3 is also applicable to home biologic information sensor 13. Further, admission refusal display 54, auxiliary authentication interface 55, health control failure display 56, outside circumference sensor 57 and presence sensor 58 in FIG. 3 can also be arranged around entrance door 10 of the first apartment 2 or the like.

Figure 4:
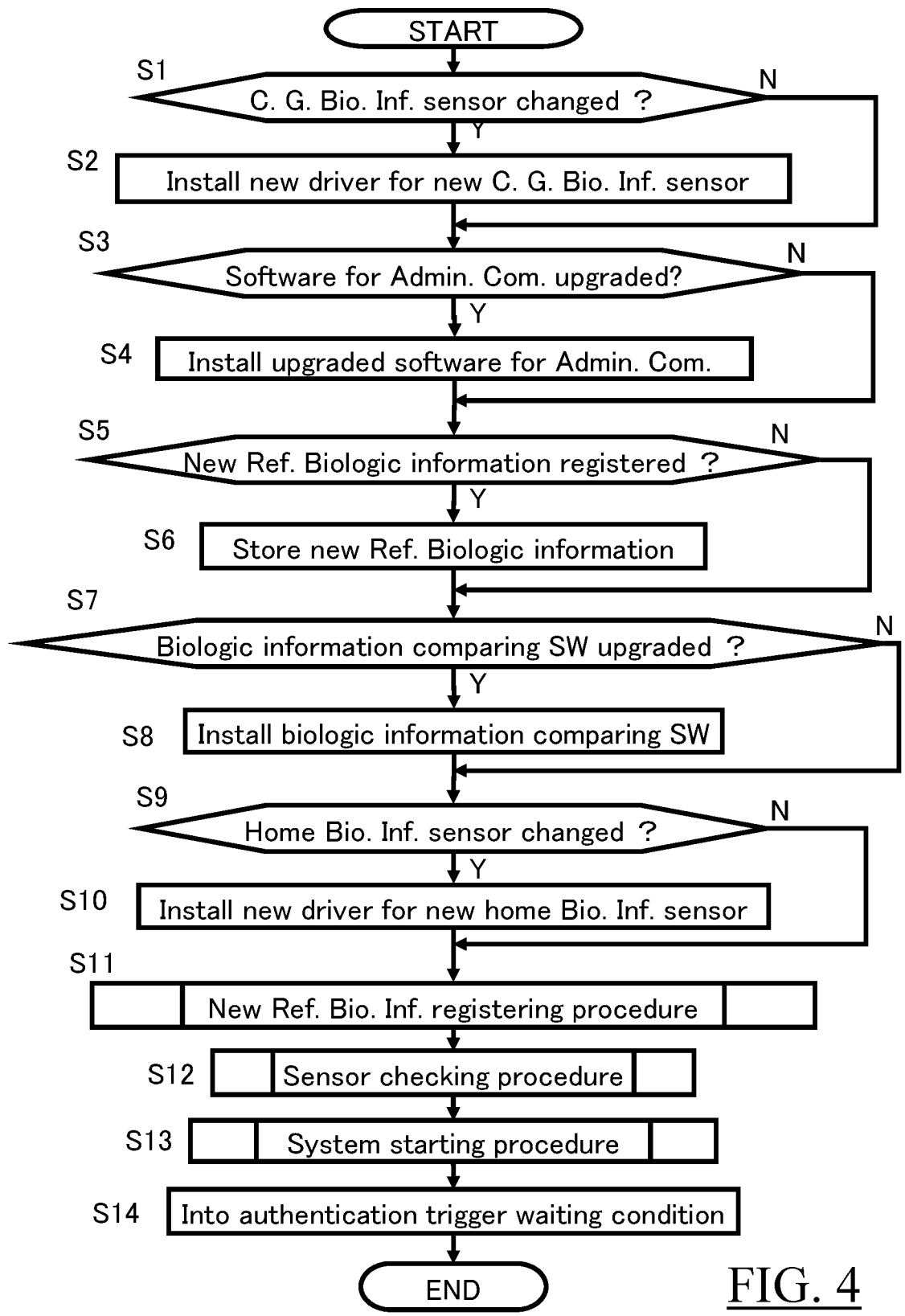
FIG. 4 is a flow chart of the basic function of the personal computer located in a condominium apartment.

FIG. 4 is a flow chart of the basic function of controller 12 of the first personal computer 5 located in the first apartment 2. The basic function is suitably repeated in accordance with the operation system of the first personal computer 5.

When the flow starts, it is checked whether or not commercial grade biologic information sensor 21 is replaced by a new one in step S1. If the replacement has been done, new driver software for the new commercial grade biologic information sensor 21 is automatically downloaded from administration computer 19 and installed into the first personal computer in step S2 so as to handle information form the new type of commercial grade biologic information sensor 21, and the flow advances to step S3. On the other hand, the flow directly advances form step S1 to step S3 if there is no replacement done.

In step S3, it is checked whether or not the software in administration computer 19 has been upgraded. If the software has been upgraded, the new software is automatically downloaded from administration computer 19 and installed into the first personal computer 5 in step S4, and the flow advances to step S5. On the other hand, the flow directly advances form step S3 to step S5 if there is no software upgraded.

In step S5, it is checked whether or not new reference information has been registered at reference biologic information register 23 of medical institute 9. If new reference has been registered, the new reference is automatically downloaded from medical institution 9 and stored into reference health information holder 16 in step S6, and the flow advances to step S7. On the other hand, the flow directly advances form step S5 to step S7 if there is no new reference registered.

In step S7, it is checked whether or not biologic information comparing software 24 in medical institution 9 has been upgraded. If the software has been upgraded, the new software relating to the upgrade is automatically downloaded from host computer 22 in medical institution 9 and installed into the first personal computer in step S8, and the flow advances to step S9. On the other hand, the flow directly advances form step S7 to step S9 if there is no software upgraded.

In step S7, the software in the first personal computer 5 is compared with current biologic information comparing software 24 to decide whether or not the biologic information comparing software 24 is upgraded. In other words, the decision of "upgraded" does not relate to when the upgrade of biologic information comparing software 24 was actually done, but relates to what software is in the first personal computer 5 when the comparison in step S7 is done. So, if the first apartment 2 has just joined the home health control system with no software relating the system existing in the first personal computer 5 yet, step S7 decides that "upgrade has been done" to automatically install the current biologic information comparing software 24 into the first personal computer 5 in step S8 regardless of the actual upgrade time at medical institution 9.

In step S9, it is checked whether or not home biologic information sensor 13 is replaced to a new one. If the replacement has been done, necessary procedure is taken in step S10 to install new driver software for the new sensor, and the flow advances to step S11. On the other hand, the flow directly advances form step S9 to step S11 if there is no replacement done.

In step S11, a procedure of registering new reference information into reference biologic information holder 14 of the first personal computer 5 is done. This procedure is necessitated upon moving of a new family into condominium building 1, or addition of a new member to a family, or replacement into an upgraded home biologic information sensor 13 or commercial grade biologic information sensor 21 requiring a new reference biologic information. The procedure of registering new reference information for home biologic information sensor 13 differs from that for commercial grade biologic information sensor 21. These procedures in detail will be explained later.

Next, the performance of the sensors is checked in step S12. This check is necessary not only for initially confirming the performance of the newly replaced sensor relating to step S1 or step S9, but also for periodically inspecting the existing sensors to promptly find out their damage or deterioration. This procedure in detail will be explained later.

Step S12 is followed by step S13 in which a procedure of starting the system, the detail of which will be explained later. And then flow advances from step 13 to step 14 to make the first personal computer 5 into a condition of waiting the authentication trigger. Under such a authentication trigger waiting condition, the first personal computer 5 can automatically start the authentication when a person comes in front of entrance door 10 is detected. The first personal computer 5 can also start the authentication when it is informed by administration computer 19 that presence sensor 58 detects a person in front of the entrance of condominium building 1.

When the authentication is automatically triggered under the waiting condition, the first personal computer 5 distinguishes whether the trigger is caused by the authentication request by someone at home biologic information sensor 13 or by the information from administration computer 19, to thereby enter into one of the two different flows corresponding to the two cases, respectively. The two different flows are each explained later in detail. If the first personal computer 5 is in use for another purpose, an indication of the fact that the authentication is triggered is superimposed on the monitor of the first personal computer 5.

Figure 5:
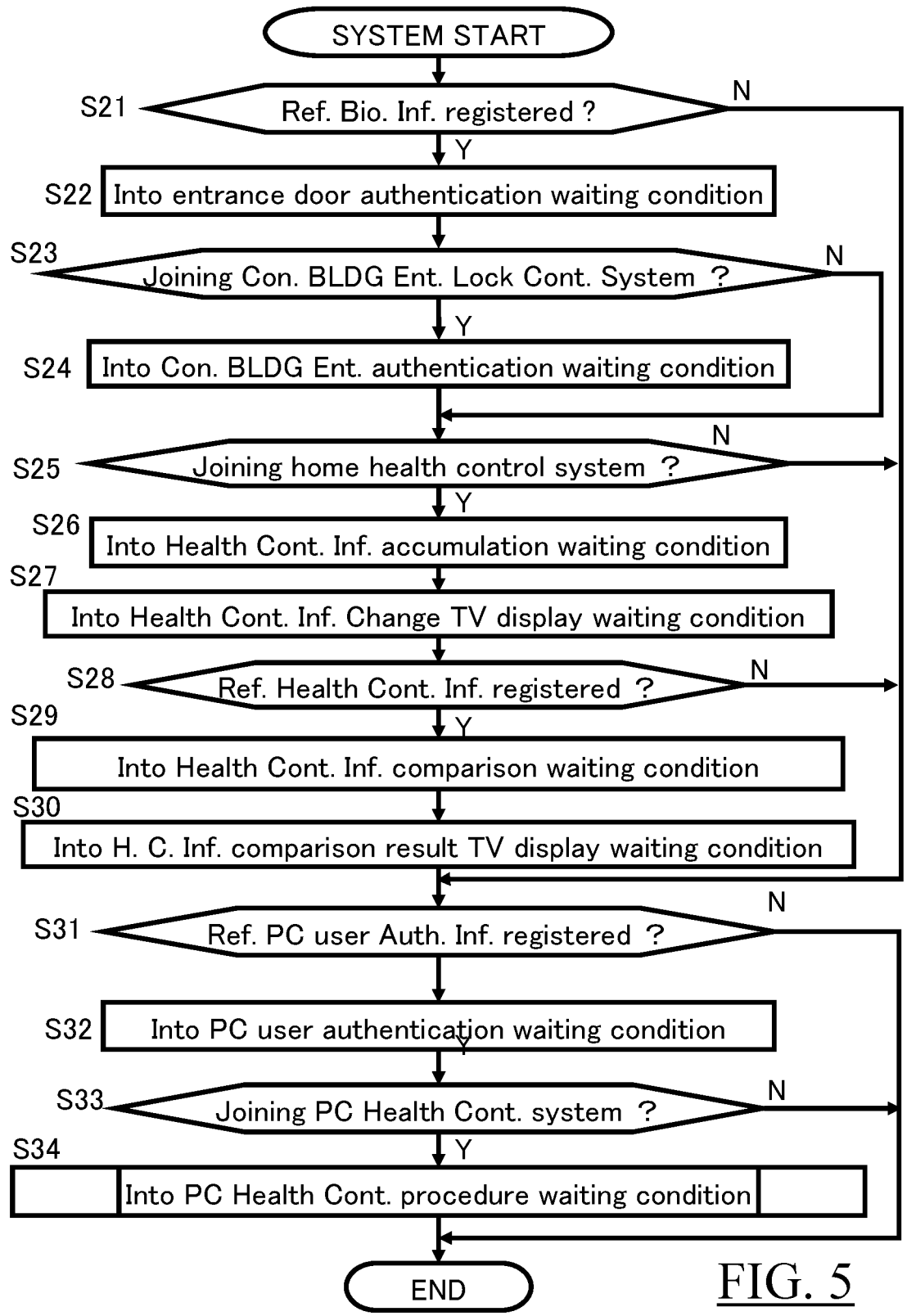
FIG. 5 is a flow chart showing the detail of step 12 in FIG. 4.

FIG. 5 is a flow chart showing the detail of step 12 in FIG. 4 that relates to the procedure of starting the system by the controller 12 of the first personal computer 5.

When the system start procedure is initiated, it is checked in step S21 whether any reference information is registered in reference biologic information holder 14. If there is some reference is registered, the flow advances to step S22 to make the system into a condition of waiting an authentication request at entrance door 10 with respect to each person relating to the registered reference.

Next, it is checked in step S23 whether or not the first apartment 2 has joined condominium building entrance lock control system 8. If the first apartment 2 has joined the system, the flow advances to step S24 to make the system into a condition of waiting an authentication request thorough condominium building entrance lock control system 8 with respect to each person relating to the registered reference, and the flow advances to step S25. If the first apartment 2 is determined in step S23 not to join the system, the flow advances directly to step S25. In this case, the unlocking on the basis of biometrics is limited to entrance door of the first apartment 2. In other words, the inhabitant of the first apartment 2 is not entitled to go through the entrance of condominium building 1 on the biometrics.

In step S25, it is checked whether or not the first apartment 2 has joined the home health control system administrated by medical institution 9. If the first apartment 2 has joined the system, the flow advances to step S26 in which the first personal computer 5 comes to standby state of accumulating health control information into individual health control database 15 with respect to every person corresponding to reference information registered in reference biologic information holder 14.

Next, in step S27, the first personal computer 5 also comes to standby state of displaying on television set 17 the moment-to-moment change in the output of the biologic information sensors stored in individual health control database 15. Such a display is possible without the reference health control information.

Next step S28 checks whether or not the reference health control information registered by reference biologic information register 23 of medical institution 9 has been stored in reference health information holder 16. If the health control information has been stored in reference health information holder 16, the flow advances to step S29 in which the first personal computer 5 comes to standby state of comparing health control information coming from the sensors or stored in individual health control database 15 with the reference information in reference health information holder 16 with respect to every person corresponding to reference information registered in reference biologic information holder 14.

Next, in step S30, the first personal computer 5 also comes to standby state of displaying on television set 17 the result of the comparison, and the flow goes to step S31.

In step S21, if there is no reference information registered in reference biologic information holder 14, the flow directly goes to step S31 since the function of authentication for unlocking and health control cannot be expected at all.

Further, in step S25, if the first apartment has not joined the home health control system administrated by medical institution 9, the flow directly goes to step S31 since the function of health control cannot be expected.

In step S28, if the reference health control information registered by reference biologic information register 23 of medical institution 9 has not been stored in reference health information holder 16, the flow directly goes to step S31 since the function of steps 29 and 30 cannot be expected.

From step S31, the authentication of the user of the first personal computer 5 starts. In step S31, it is checked whether or not the reference information for authenticating the personal computer user is registered in reference biologic information holder 14. If the reference information is registered, the flow advances to step S32 in which the first personal computer 5 comes to standby state of waiting authentication request to access the first personal computer 5 with respect to every person corresponding to reference information registered in reference biologic information holder 14, and the flow advances to step S33. On the other hand, if there is no reference registered in reference biologic information holder 14, the procedure of starting the system is instantly terminated to go to step S14 of FIG. 4 since no more step is necessary.

Following step S32, it is checked in step S33 whether or not the user authentication function of the first personal computer 5 has joined the home health control system administrated by medical institution 9. If the use authentication function of the first personal computer 5 has joined the home health control system, the flow advances to step S34 in which the first personal computer 5 comes to standby state of storing health control information into individual health control database 15 and comparing the same with the reference information stored in reference biologic information holder 14 with respect to every person corresponding to reference information registered in reference biologic information holder 14, and the procedure of starting the system is terminated. On the other hand, if the user authentication function of the first personal computer 5 has not joined the home health control system, the procedure of starting the system is instantly terminated.

In FIG. 5, the preparation of the standby state of both storing health control information and comparing the same with the reference is shown as if such a function is carried out by single step of step S34. In detail, however, step S34 includes a plurality of sub-steps similar to step 26 to step 30. In other words, in the initial stage of step S34, the first personal computer 5 comes to a standby state of storing health control information into individual health control database 15 and displaying the moment-to-moment change in the health control information, which is similar to the function carried in steps S26 and step S27. And in the succeeding stage of step S34, after confirming that the reference health control information has been stored in reference health information holder 16, the first personal computer 5 comes to standby state of comparing health control information with the reference information in reference health information holder 16 and displaying the result, which is similar to the function carried out in steps S28 and step S30.

Figure 6:
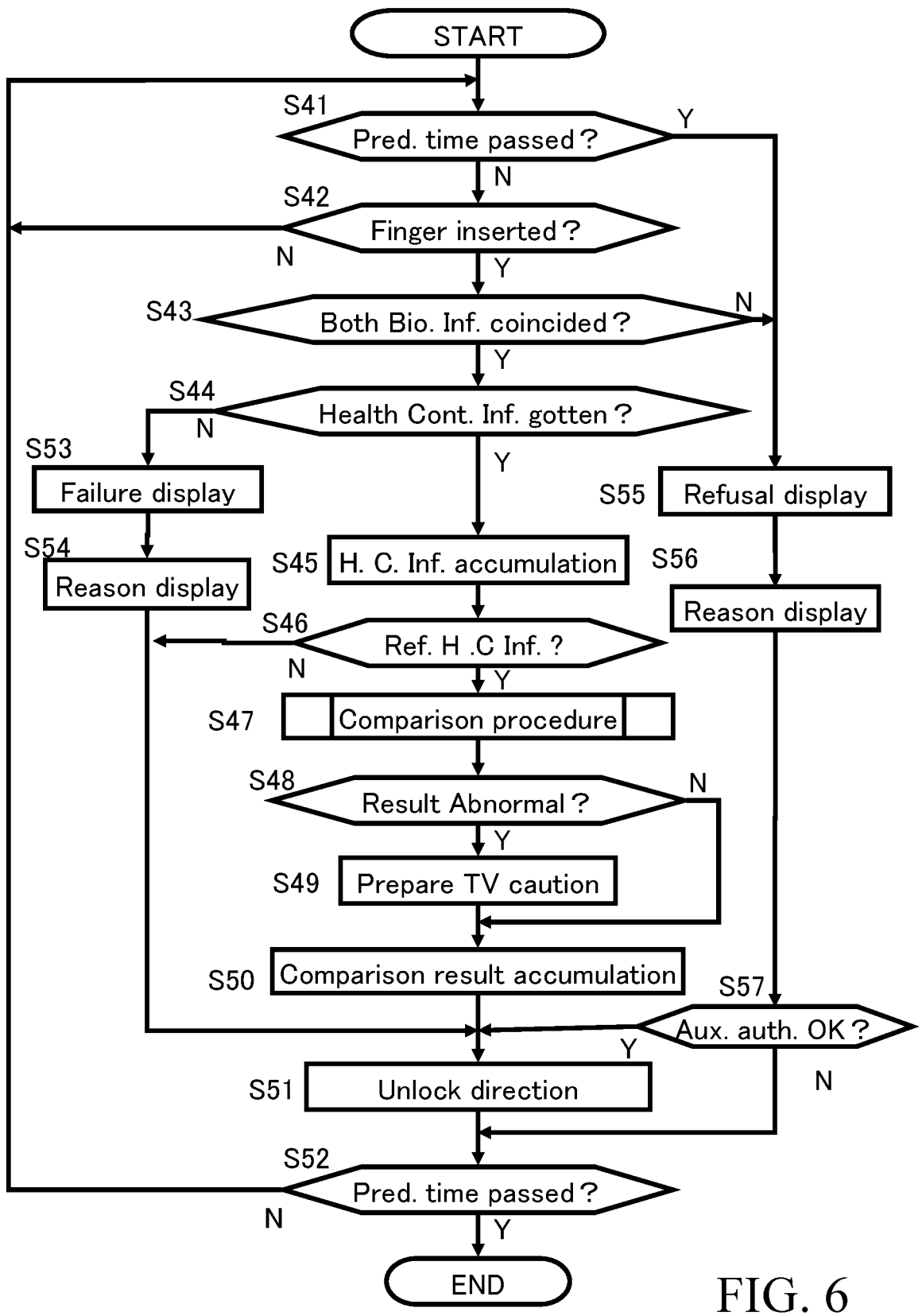
FIG. 6 is a flow chart of the personal computer located in the condominium apartment with the authentication system triggered at the entrance door of the condominium apartment for the first embodiment.

FIG. 6 is a flow chart of the function carried out by controller 12 of the first personal computer 5 located in the first apartment 2 with the authentication system triggered by a person coming to stand in front of entrance door 10.

If the system is triggered, it is checked in step S41 whether or not a predetermined time has passed after the person comes to stand in front of entrance door 10. If the time has not passed yet, the flow advances to step S42 in which it is checked whether or not a finger is inserted into home biologic information sensor 13. If no finger is inserted, the flow goes back to step S41, and steps S41 and S42 are repeated waiting for the insertion of a finger for the predetermined time.

If the insertion of a finger is detected in step S42, the flow goes to step S43 in which the sensed biologic information from the finger is compared with the reference biologic information stored in reference biologic information holder 14 to determine whether or not the both coincide with each other. If the sensed information coincides with the reference information, the flow advances to step S44 in which it is checked whether home biologic information sensor 13 succeeds in getting sufficient information for health control. A case of failure in step S44 means that the biologic information gotten by home biologic information sensor 13 is sufficient for the purpose of authentication of unlock, but is insufficient for the purpose of health control. Thus, the biologic information gotten by home biologic information sensor 13 has the first level of accuracy required by authentication and the second level of accuracy required by health control, the second accuracy level being generally higher. Further, it takes more time to take the second accuracy level of biologic information. So, if the time of inserting the finger is too short, it may be judged in step S44 that home biologic information sensor 13 fails in getting sufficient information for health control.

If it is judged that in step S44 that home biologic information sensor 13 succeeds in getting sufficient information for health control, the flow advances to step S45 in which the sensed information is stored into individual health control database 15. The information stored in individual health control database 15 is also sent to host computer 22 in real time for the storage in central health control database 27. This means that the information in individual health control database 15 is backed up by central health control database 27, which make it easy for moving out of condominium building 1 without losing individual health control database.

Next, in step S46, it is checked whether or not a reference exists in reference health information holder 16. If there is any reference information, the flow advances to step S47 in which the sensed information is compared with the reference in reference health information holder 16. And, the flow goes to step S48 to judge whether the result of comparison show any abnormality of health control information. If some abnormality detected, the flow advances to step S49 to prepare for display on television set 17 so that an indication of the abnormality caution is to be automatically made when its power switch is turned on, and the flow goes to step S50. If there is no abnormality judged, the flow directly goes to step S50. Upon the indication of abnormality, a display with identification of a person relating to such an abnormality is possible on the basis of the result of function in step S43.

With respect to the display on television set 17, it is possible to indicate in step S49 some new biologic information inviting attention of the person originating the biologic information even if such new information does not mean any abnormality. In this case, step S48 is modified to be capable of further detecting the existence of such new biologic information.

Further, in step S49 may be modified to automatically turn on television set 17 to instantly make the indication of abnormality if the abnormality is of high emergency.

For respecting the privacy, it is possible to previously set the first personal computer 5 not to prepare the indication of abnormality on television set 17 in step S49 for a specific person who does not want the indication to be made automatically under a possibility of presence of another person even in the same family.

In step S50, the comparison result is gotten in step S47 is stored in individual health control database 15. The information stored in individual health control database 15 in step S50 is also sent to host computer 22 in real time for the storage in central health control database 27. The abnormality judged in step S48 is also sent to host computer 22 in real time for the storage in central health control database 27.

By way of the above steps, the flow comes to step S51 to inform door lock 11 of the unlock direction. In response to the direction, door lock 11 unlocks entrance door 10. After unlocking door lock 11, step S52 checks again whether or not the predetermined time has passed after the person comes in front of entrance door 10. The meaning of step S52 is explained later.

If it is detected in step S46 that there is no reference information in reference health information holder 16, the flow directly goes to step S51 to instantly inform door lock 11 of the unlock direction since there is no necessity of carrying out steps S47 to S50.

On the other hand, if it is determined that home biologic information sensor 13 fails in getting sufficient information for health control information, the fact of failure is displayed in step S53, the reason of failure being also displayed in step S54 prior to getting to step S51. Thus, even if the health control information is failed to be gotten, the unlocking of door lock 11 itself is made.

A person who is going to enter entrance door 10 and perceives the display of the failure and its reason may try to insert his or her finger again into home biologic information sensor 13. Step S52 is provided for such a case. In other words, if the predetermined time has not passed yet after the person comes in front of entrance door 10, the flow returns from step S52 to step S41, which makes it possible for the person to again insert his or her finger. On the other hand, if it is determined in step S52 that the predetermined time has passed, the flow of FIG. 6 go to the end. If the person still wants to try again getting the health control information after the predetermined time has passed, the person can try it by means of once coming off the entrance door 10 and again approaching it so as to trigger the flow of FIG. 6.

If the person is in hurry to enter entrance door 10, he or she can enter into the first apartment 5 with noting the display of the failure in getting health control information in step 53 and step 54. In this case, however, the person learns by heart the reason of failure displayed, and will insert the finger with care not to repeat the same failure next time.

In step S41, if the predetermined time has passed after the person comes to stand in front of entrance door 10 without inserting a finger, the flow advances to step S55, in which admission refusal indication is displayed. Further, the indication of the reason of refusal is displayed in step S56, the reason being the non-insertion of a finger in this case.

Next, in step S57, auxiliary conventional authentication system such as password system or IC card system is made available to check whether or not such an auxiliary conventional authentication is successful. It the auxiliary conventional authentication is successful, the flow advances to step S51 to unlock the door lock 11.

It should be noted that the case of unlocking by way of step S57 is recorded so as to be distinguishable from the case of unlocking by way of step S50 or step S54. This is because that the authentication by means of biometrics system is the base of the system according to this invention, the auxiliary conventional authentication system being mere a backup with lower security. So, the distinguishable record of unlocking by means of the auxiliary conventional system serves as a warning that the system is unable to function normally.

If the auxiliary conventional authentication is not made or unsuccessful, the flow finally goes to the end by way of step 52, entrance door 11 being not unlocked.

If the sensed information does not coincide with the reference information or is insufficient to be compared with the reference information in step S43, the flow advances to step S55 to display the admission refusal indication. Further, the indication of the reason of refusal is displayed in step S56, the reason being the discrepancy or insufficiency of the sensed information in this case.

Next, in step S57, the auxiliary conventional authentication system such as password system or IC card system is made available to unlock the door lock in step S51 if the auxiliary conventional authentication is successful in step S57. If the auxiliary conventional authentication is not made or unsuccessful, the flow finally goes to the end by way of step 52.

If the predetermined time has not passed yet in step S52 coming by way of step S57, the flow retunes to step S42 by way of step S41. So, it is possible to go to step S44 by way of step S43 to finally get to step S51 for unlocking entrance door 10 if the person more carefully inserts the finger again with the indication made in step S56 taken into consideration.

It should be noted that step 43 is located before step S44 not to allow getting to the health control flow unless the authentication for unlocking purpose is successful. The first reason is that a person who cannot be authenticated has no meaning of health control at all.

The second reason, which is more important, is that the health control information is prevented from being gotten from a person who inserts the finger improperly even if the person is entitled to enter the entrance door 10. In other words, the success in authentication is a proof of the proper insertion of the finger at least of the authentication level. By this arrangement, wrong health control information gotten with the finger improperly inserted is prevented from being gotten.

In other words, reliability of the health control information is kept by excluding health control information of a person who cannot be authenticated even if biologic information gotten by such a person is of a sufficient level for health control.

Figure 7:
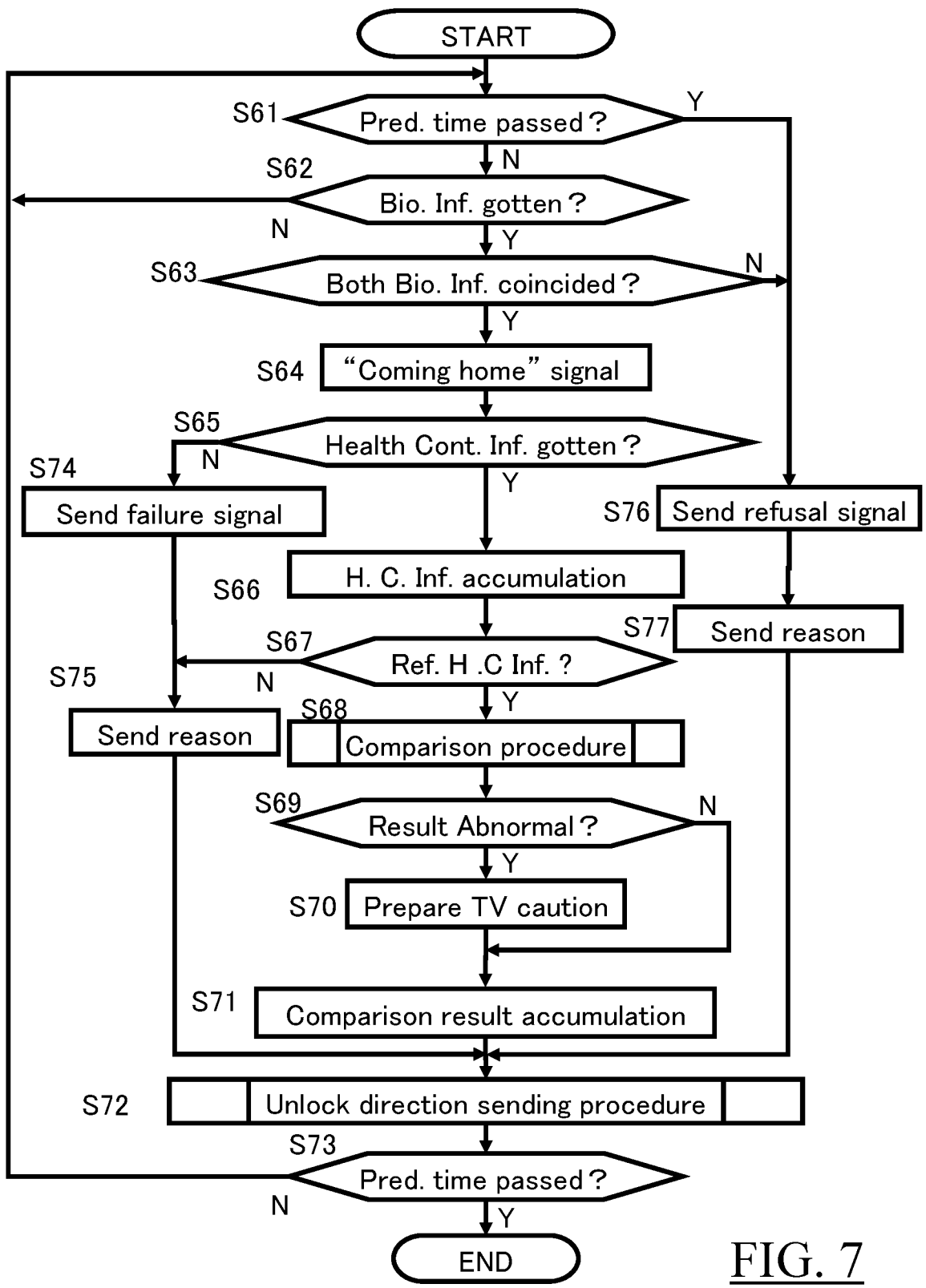
FIG. 7 is a flow chart of the personal computer located in the condominium apartment with the authentication system triggered at the entrance of the condominium building for the first embodiment.

FIG. 7 is a flow chart of the function carried out by controller 12 of the first personal computer 5 located in the first apartment 2 with the authentication system triggered by administration computer 19 that inform the first personal computer 5 of a person coming to stand in front of the entrance of condominium building 1. Since the function of FIG. 7 is similar to that of FIG. 6, the explanation is omitted with the difference only commented.

In place of the first personal computer 5 which checks the insertion of a finger in S42 in FIG. 6, administration computer 19 makes the check of finger insertion. Accordingly, in step 62 in FIG. 7, it is checked whether or not administration computer 19 informs the first personal computer 5 of the finger biologic information gotten by commercial grade biologic information sensor 21 located at condominium building entrance lock control system 8.

Step 64 is typically added in FIG. 7 in which "coming home" signal is generated when the received finger biologic information coincides with the reference biologic information in step S63. By means of such a "coming home" signal, a wife in the first apartment 2 for example can know in advance the coming home of her husband at the stage that he has just gotten to the entrance of the condominium building 1. Or, in the case that the coming home person lives alone, the "coming home" signal can be used to automatically turn on the illumination and air conditioner of the first apartment 2.

FIG. 6 includes steps S53 to S56 relating to various indication display. In the case of FIG. 7, however, the corresponding indication is displayed by administration computer 19 which controls admission refusal display 54 and health control failure display 56. Therefore, in corresponding steps S74 to S77 of FIG. 7, the first personal computer sends command signal to have administration computer 19 carry out the indication display.

In FIG. 6, step 56 is followed by step S57 for the auxiliary conventional authentication carried out by the first personal computer 5. In the case of FIG. 7, on the contrary, the corresponding auxiliary conventional authentication in condominium building entrance lock control system 8 is carried out only by administration computer 19. Therefore, step S77 instantly leads to step S73.

Further, FIG. 6 includes steps S51 relating to the unlocking of the entrance door 10. In the case of FIG. 7, however, the corresponding unlocking of the entrance of condominium building 1 is carried out by administration computer 19. Therefore, in corresponding step S72 of FIG. 7, the first personal computer sends an unlock command signal to have administration computer 19 carry out the unlock function.

The unlock command signal sent in step S72 is a very important signal not relating to a local apartment only, but relating to entire condominium building 1. So, the command signal is carefully sent in step S72 in accordance with an administration command from administration computer 19 received along with the finger biologic information in step S62. In other words, the unlock command signal is encrypted in accordance with the administration command. Further, the timing to send the unlock command is limited within a very short period directed by administration command from administration computer 19. The detail of the manner of sending the unlock command will be explained later.

Functions of the steps in FIG. 7 other than the above are similar to the corresponding functions in steps in FIG. 6 and the explanation therefore is omitted.

Figure 8:
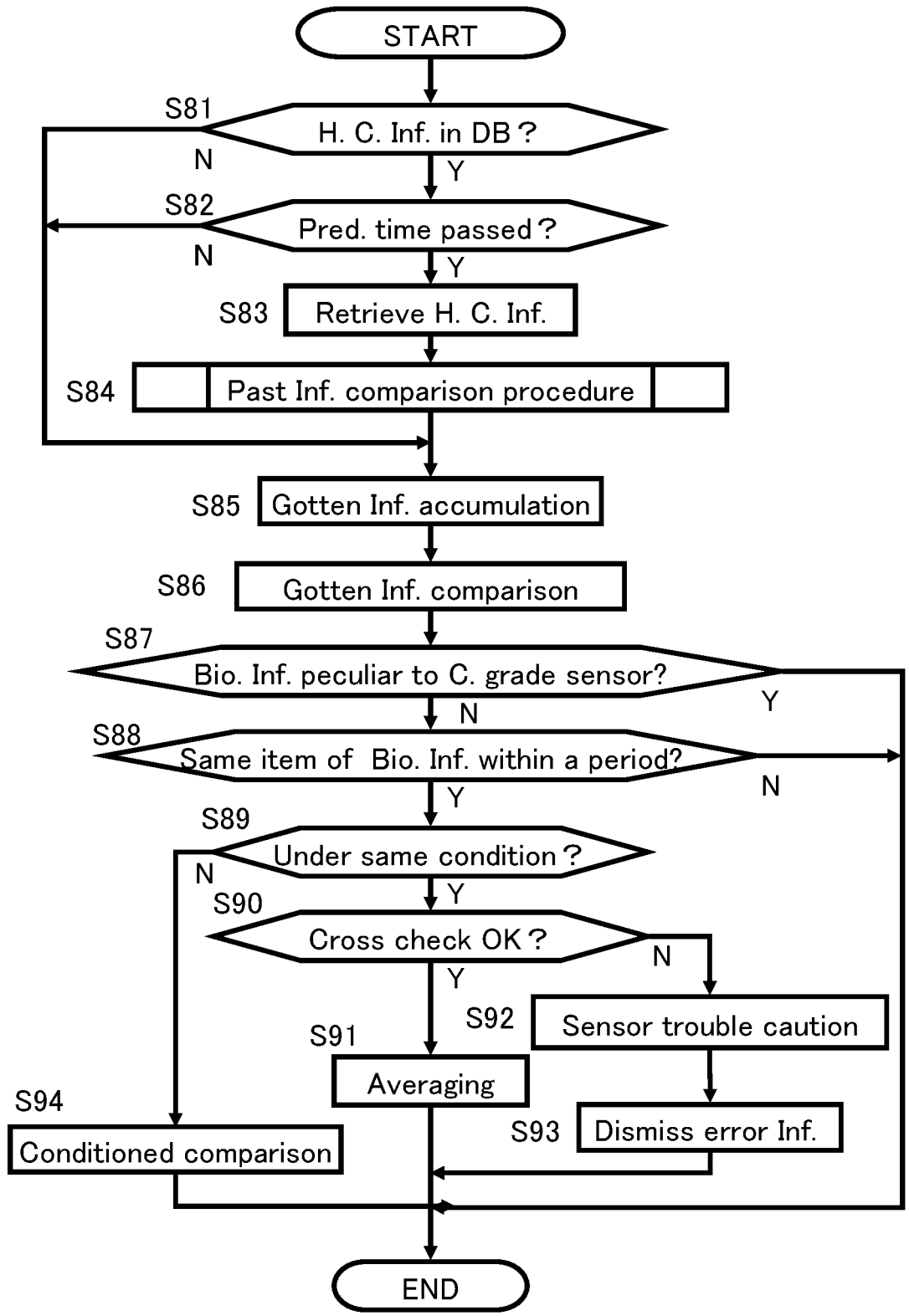
FIG. 8 is a flow chart showing the details of step 47 in FIG. 6 and step 68 in FIG. 7 for the first embodiment.

FIG. 8 is a flow chart showing the details of step 47 in FIG. 6 and step 68 in FIG. 7 relating to the comparison function carried out by controller 12 of the first personal computer 5.

If the comparison flow starts, it is checked in step S81 whether or not individual health control database 15 includes any information stored in the past. If there is some information storage, the flow advances to step S82 in which it is checked in step S82 whether or not a predetermined time has passed since the information was stored. This is because a too new past information stored within the predetermined time is meaningless to be analyzed.

If there is some information stored in individual health control database 15 with the predetermined time having passed since its storage date, the flow advances to step 83 in which the past information is read out from individual health control database 15. The read out past information is processed in step S84 for comparison. According to the past information comparison process in step S84, not only the past information read out from individual health control database 15, but also current information newly gotten by home biologic information sensor 13 or commercial grade biologic information sensor 21 is processed. The process in step S84 includes analysis of the moment-to-moment change and season change or the like, the details being explained later. The process in step S84 is followed by step S85.

In step S81, on the other hand, if individual health control database 15 includes no information stored in the past, the flow directly advances to step S85. Also in step S82, if all the past information storage are too new not exceeding the predetermined time, the flow directly advances to step S85. This is because steps S83 and S84 are not necessary in both the cases.

In step S85, the current information newly gotten by home biologic information sensor 13 or commercial grade biologic information sensor 21 is accumulated in individual health control database 15. Step S85 is followed by step S86 in which the current information is simply compared with the reference information in reference health information holder 16 to go to step S87. In steps beginning form step S87, it is checked whether or not further high grade comparison process is possible to carry out such a high grade comparison process if possible.

In step S87, it is checked whether or not the newly gotten biologic information relates to an item typical of commercial grade biologic information sensor 21. A negative answer to the question in step S87 means that the newly gotten biologic information relates to an item common to both home biologic information sensor 13 and commercial grade biologic information sensor 21. In this case, accordingly, the flow advances to step S88 to check whether or not any same item of biologic information is gotten by both home biologic information sensor 13 and commercial grade biologic information sensor 21 within a predetermined short period.

If such the same item of biologic information exists, it is normally assumed that a coming home inhabitant of the first apartment 2 for example makes the first authentication with commercial grade biologic information sensor 21 at the entrance of condominium building 1 and successively makes the second authentication with home biologic information sensor 13 at entrance door 10 of the first apartment 2.

If same item of biologic information gotten by both home biologic information sensor 13 and commercial grade biologic information sensor 21 within a predetermined short period exists, the flow advances to step S89 to check whether or not the condition of getting the same item of biologic information is the same. If the information getting condition is the same, the flow advances to step S90 to conduct a cross check between both the information from home biologic information sensor 13 and commercial grade biologic information sensor 21. It is assumed that the two biologic information of the same item gotten within the short period under the same condition are nearly equal to each other. So, if the two differ from each other over a limit, one of the sensors may possibly be out of order. Thus, if the two biologic information of the same item gotten within the short period under the same condition are nearly equal to each other in step S90, which means that both the biologic information are reliable, the flow advances to step S91 to average the two biologic information for improving the accuracy of information. And then, flow goes to the end.

On the other hand, if the two biologic information of the same item gotten within the short period under the same condition differ from each other over a limit in step S90, the flow advances to step S92 to identify one of the sensors which is out of order in accordance with a comparison between the newly gotten biologic information and the past biologic information stored in individual health control data base 15, a caution being made that the identified sensor is in trouble or out of order. Further, the information gotten from the identified sensor is dismissed as being unreliable in step S93.

Thus, if the condition, under which the same item of biologic information is gotten, is the same in step S89 with respect to home biologic information sensor 13 and for commercial grade biologic information sensor 21, the same item of biologic information is analyzed twice for improving the reliability of the biologic information.

On the contrary, if the information getting condition is not the same in step S89 with respect to home biologic information sensor 13 and for commercial grade biologic information sensor 21, a comparison analysis depending on the change in the information getting condition is possible. The difference in information getting condition means the difference in exercise stress on the same person between the cases of authentication by commercial grade biologic information sensor 21 and by home biologic information sensor 13. Further, the change in circumstance such as temperature between the outside where commercial grade biologic information sensor 21 is located and the inside where home biologic information sensor 13 is located is another example of the change in information getting condition. These difference in information getting condition may influence on health control information, which make it possible to analyze the health control information depending on the information getting condition.

If such a difference in information getting condition is detected in step S89, the flow advances to step S94 in which the comparison between the gotten information and the reference information is made with the correlation to the information getting condition taken into consideration. Examples of the information getting condition to be considered in analyzing the correlation are the pulsation which reflects the exercise stress and temperature, humidity and wind velocity, or the like.

In step S87, if it is checked that the newly gotten biologic information relates to an item typical of commercial grade biologic information sensor 21, home biologic information sensor 13 never senses the same item of biologic information. Therefore, the flow is instantly ended with the current information having been simply compared with the reference information in reference health information holder 16 in step 86.

Further in step 88, if any same item of biologic information is not gotten by both home biologic information sensor 13 and commercial grade biologic information sensor 21 within the predetermined short period, the flow is instantly ended since the steps beginning from step S89 are not meaningful any more in such a case.

It should be noted that the flow chart in FIG. 8 makes it possible for step 88 to advance to step S89 in such a case caused by some special reason that the same item of biologic information is successively gotten within the predetermined short period by only one of home biologic information sensor 13 and commercial grade biologic information sensor 21.

Figure 9:
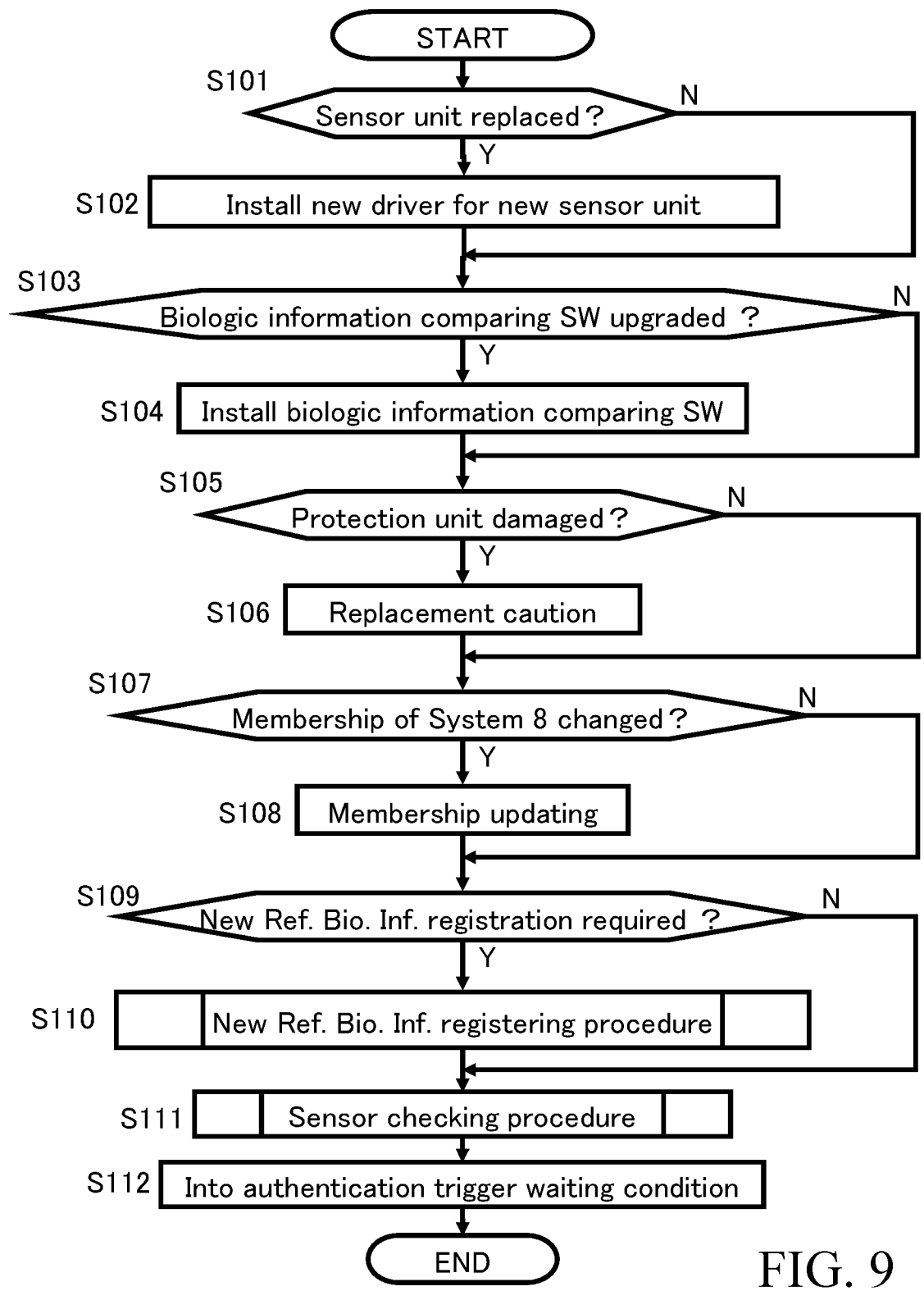
FIG. 9 is a basic flow chart of the personal computer located in the administration center of the condominium building for the first embodiment.

FIG. 9 is a flow chart showing the basic function of administration controller 53 of administration computer 19 located at condominium building entrance lock control system 8. The basic function is suitably repeated in accordance with the operation system of administration computer 19.

When the flow starts, it is checked whether or not sensor unit 51 of commercial grade biologic information sensor 21 is replaced to a new one in step S101. If the replacement has been done, new software for the new sensor unit 51 is installed into administration computer 19 in step S102. If the new sensor unit 51 is provided by medical institution 9, administration controller 53 automatically downloads the new software from host computer to automatically install the downloaded software. The flow goes to step S103 after the install of the new software. On the other hand, if sensor unit 51 is not replaced, the flow goes from step S101 to step 103 directly.

In step S103, it is checked whether or not biologic information comparing software 24 in medical institution 9 has been upgraded. If the software has been upgraded, the new software is automatically downloaded from host computer 22 to be installed into the administration computer 19 in step S104, and the flow advances to step S105. On the other hand, the flow directly advances form step S103 to step S105 if there is no biologic information comparing software 24 upgraded.

In step S103, medical institution 9 can also inform administration computer 19 of other services that medical institution 9 can provide as well as the upgraded biologic information comparing software 24. In other words, step S103 which has to be carried out without fail for the purpose of maintenance of health control system is an important opportunity for medical institution 9 to advertise other business. In step S103, for example, medical institution 9 can inform its individual client of a reminder of next consultation day or announcement of routine health checkups or season pollen information through administration computer 19.

If medical institution 9 sends in step S103 the above mentioned information having no direct relation to the health control system, administration computer 19 stores such information in step 104 to transmit it to the first personal computer 5 or the like so that the information will be displayed on television set 17 when turned on.

The function in steps S103 and S104 explained above can be carried out by the first personal computer in Steps S7 and S8 so as to directly receive from medical institution 9 the information having no direct relation to the health control system.

In step S105 it is checked whether or not protection unit 52 which is exposed to outside environment is vandalized or tainted. If it is determined that sensor unit 51 is out of order because of vandalized or tainted protection unit 52, the flow goes to step S106 to make a caution to replace protection unit 52 and advances to step S107. On the other hand, if protection unit 52 is not vandalized or tainted checked, the flow directly goes from step S105 to S107.

In step S107, it is checked whether or not any change in the membership of condominium building entrance lock control system 8 has been caused. The change means that an apartment gets in or out of condominium building entrance lock control system 8. If there is some change in the membership, the flow advances to step S108 to put the change into condominium building entrance lock control system 8 for updating the same.

By means of these steps, an inhabitant newly move into condominium building 1 is becomes to be entitled to enter the entrance of condominium building 1. In other words, administration computer 19 can administrate all the apartments currently joining condominium building entrance lock control system 8 for receiving the necessary unlock command signal from one of the apartments without fail. After the process carried out in step S108, the flow advances to step S109. If there is no change in the membership, on the other hand, the flow directly goes from step S10 to step S109.

In step S109, it is checked whether or not new reference information is required to be registered at condominium building entrance lock control system 8. If new reference registration is required, the flow advances to step S110 to make necessary step to register the new reference, and further advances to step S111. The details of step S110 will be explained later. On the other hand, the flow directly advances form step S109 to step S111 if there is no new reference registration required.

In step S111, the performance of the sensor is checked. This check is basically similar to the check conducted in step S12 in FIG. 4. Administration computer 19 is, however, in charge of checking commercial grade biologic information sensor 21 with respect to its initial function upon replacement and a damage or deterioration caused thereafter. The details of step S111 will be explained later.

And then flow advances from step 111 to step 112 to make the administration computer 19 into a condition of waiting the authentication trigger. Under such a authentication trigger waiting condition, administration computer 19 can automatically start the authentication when presence sensor 58 detects a person comes in front of the entrance of condominium building 1.

Figure 10:
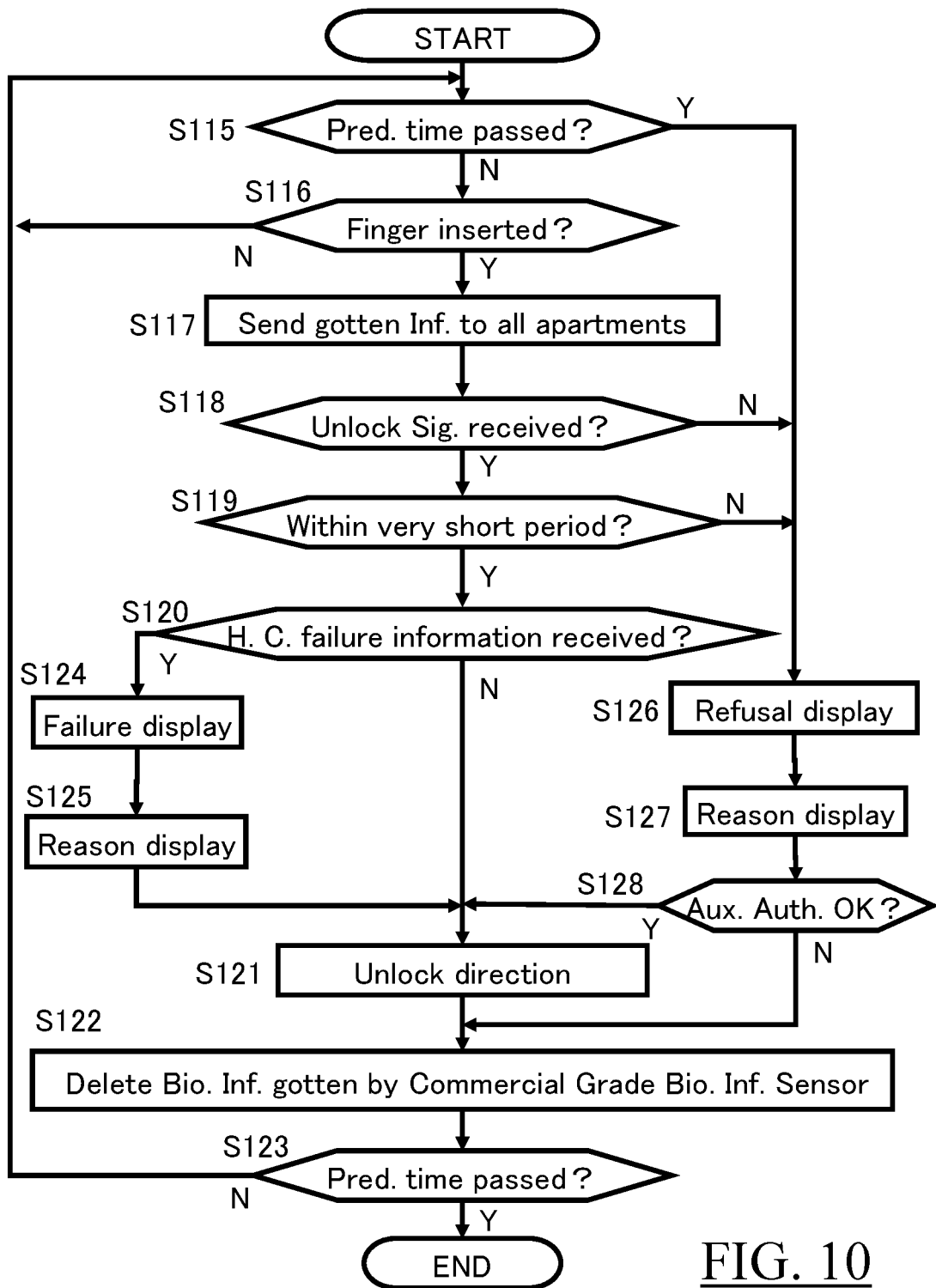
FIG. 10 is a flow chart of the personal computer located in the administration center of the condominium building with the authentication system triggered at the entrance of the condominium building for the first embodiment.

FIG. 10 is a flow chart of the function carried out by administration controller 53 of administration computer 19 with the authentication system triggered by a person coming to stand in front of the entrance of condominium building 1.

If the system is triggered, it is checked in step S115 whether or not a predetermined time has passed after the person comes to stand in front of the entrance of condominium building 1. If the time has not passed yet, the flow advances to step S116 in which it is checked whether or not a finger is inserted into commercial grade biologic information sensor 21. If no finger is inserted, the flow goes back to step S115, and steps S115 and S116 are repeated waiting for the insertion of a finger for the predetermined time.

If the insertion of a finger is detected in step S116, the flow goes to step S117 in which the sensed biologic information from the finger is sent to all the apartments joining condominium building entrance lock control system 8. And, in step S118 it is checked whether or not an unlock command signal is received from any of the apartments which detects that the sent biologic information coincides with a reference biologic information for authentication. The unlock command signal is encrypted for preventing it from being forged or for avoiding confusion with an error command. Further, the timing for an apartment to send the unlock command is limited within a short period directed by an administration command from administration computer 19. The encryption key and the administration command are changed every time on random number generator and sent to all the apartments along with the sensed biologic information in step 117. If it is determined in step 118 that an unlock command signal is received from one of the apartments, the flow advances to step S119.

In step S119, it is checked whether the receipt of the unlock command signal in step 118 was within the very short time period determined by the administration command signal sent in step S117. The unlock command signal is very important since it causes the unlocking of the entrance of condominium building 1. So, not only it is checked whether the unlock command signal is received in step S118, but also it is checked whether such unlock command signal was received within the very short time period in step S119. Thus, condominium building entrance lock control system 8 prevents the entrance door from being unlocked by a forged or error command signal. As has been explained, the very short time period is unique for each of the apartments and is changed on random number generator every time it is sent in step 117. So, only a personal computer in the apartment that has been informed of the very short time period can send the unlock command signal to administration computer 19. An unlock command signal received off the very short time period is, accordingly, deemed as a forged or error command signal.

If it is checked that the receipt of the unlock command signal was within the very short time period in step 119, the flow advances to step S120.

In step S120, it is checked whether or not administration computer 19 is informed of a failure of getting health control information by any of the apartments. The receipt of such a failure information in step S120 means that an apartment judged that the sensed information sent in step S117 is sufficient for the purpose of unlock authentication, but insufficient for the purpose of health control.

If no failure information is received from any apartment in step 120, the flow advances to step S121 to direct entrance lock 20 to unlock the entrance door. Entrance lock 20 unlocks the entrance door in response to the direction.

In receiving information in steps S118 to S120, administration computer 19 is blocked from identifying a specific apartment that sends the unlock command signal and failure information for the purpose of privacy protection.

After the direction to entrance lock 20, the flow advances to step S122 to delete the biologic information which has been gotten in step S111. This is to secure privacy protection. And, the flow advances to step 123 to check again whether or not a predetermined time has passed after the person comes to stand in front of the entrance of condominium building 1. If the time has passed, the flow terminates the unlock process.

On the other hand, if it is checked that administration computer 19 is informed of a failure of getting health control information by any of the apartments, the flow advances to step S124 to display the fact of failure, the reason of failure being also displayed in step S125 prior to getting to step S121. Thus, also in condominium building entrance lock control system 8, the direction is made toward entrance lock 20 to unlock the entrance door even if it is failed to get health control information.

If it is checked in step S115 that the predetermined time has passed after the person comes to stand in front of the entrance of condominium building 1, the flow advances to step 126 to display admission refusal indication. Further, the indication of the reason of refusal is displayed in step S127, the reason being the non-insertion of a finger in this case.

Next, in step S128, auxiliary conventional authentication system such as password system or IC card system is made available to check whether or not such an auxiliary conventional authentication is successful. It the auxiliary conventional authentication is successful, the flow advances to step S121 to direct entrance lock 20 to open the entrance of condominium building 1. In analogy with the case of step S57 in FIG. 6, the case of unlocking by way of step S128 is recorded so as to be distinguishable from the case of unlocking by way of step S120 or step S125. It should be noted, however, that the higher security is required in the case of step S128 since the entrance of condominium building 1 is the public passage. Therefore, ID of the person who tried to go through the entrance of condominium building 1 by means of the auxiliary conventional authentication in step S128 is also recorded.

If the auxiliary conventional authentication is not made or unsuccessful, the flow finally goes to the end by way of steps S122 and S123, entrance lock 20 being not unlocked. In this case, step S122 has basically no function since there is no biologic information gotten. However, step S128 is followed by step S122 for the reason below.

If no unlock command signal is received from any of the apartments or admission refusal command is received from all of the apartments in step S118 with biologic information having gotten in step S116, the flow advances to step S126 to display admission refusal indication. Further, the indication of the reason of refusal is displayed in step S127.

If it is determined that the received unlock command signal is not within the very short period in step S119, the flow advances to step S126 to display admission refusal indication and in turn to step S127 to display the reason of refusal.

If administration computer 19 cannot know by itself the reason of refusal, the reason information sent in step S77 in FIG. 7 is utilized. However, administration computer 19 is blocked from identifying a specific apartment that sends the reason of refusal for the purpose of privacy protection.

Next, in step S128, auxiliary conventional authentication system such as password system or IC card system is made available to check whether or not such an auxiliary conventional authentication is successful. It the auxiliary conventional authentication is successful, the flow advances to step S121 to direct entrance lock 20 to open the entrance of condominium building 1. If the auxiliary conventional authentication is not made or unsuccessful, the flow goes to steps S122 to delete the biologic information. Thus, even in a case of failure of authentication, the biologic information is deleted for the purpose of privacy protection.

Next, the flow goes to step S123. If the time has not passed yet, the flow returns to step S116 by way of step S115, which makes it possible for the person to again insert his or her finger to have the flow go to step S117. This time, the person may more carefully insert the finger with the reason indication in step S127 taken into mind.

Figure 11:
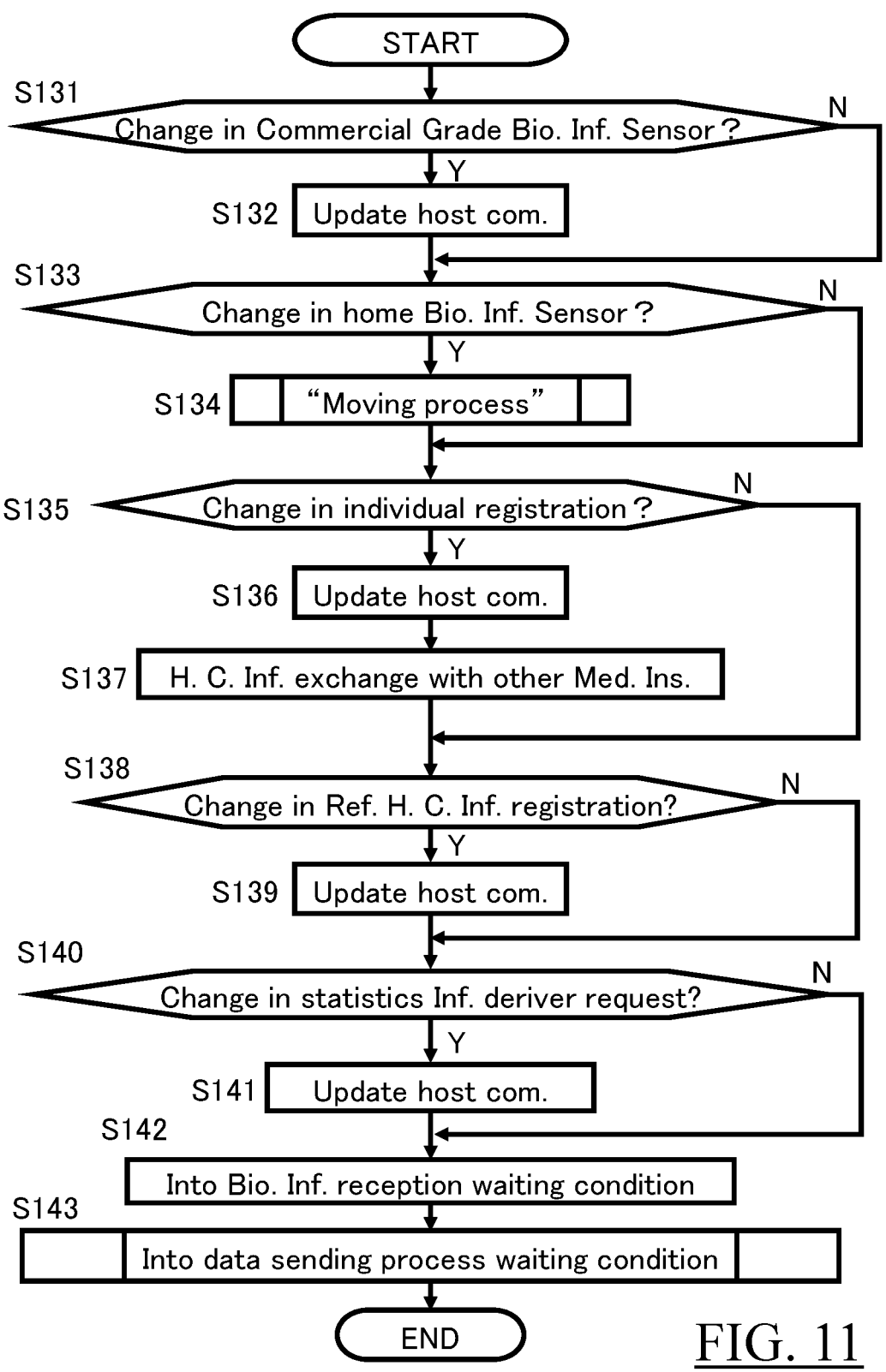
FIG. 11 is a flow chart of the basic function of the personal computer located in the medical institution for the first embodiment.

FIG. 11 is a flow chart showing the basic function of host controller 26 of host computer 22 located at medical institution 9. The basic function is suitably repeated in accordance with the operation system of host computer 22. When the flow starts, it is checked in step 131 whether or not there is any change in commercial grade biologic information sensor 21, such as a new registration, deletion of registration, or upgrading of sensor 21. The upgrading of sensor 21 includes an addition of some new function to sensor 21 with the registration thereof unchanged. If there is any change in sensor 21, the flow advances to step S132 to updated host computer 22 for reflecting the change in data or software, and the flow goes to step S133. Thus, host computer 22 can correspond to any change in commercial grade biologic information sensor 21 of any client. On the other hand, the flow directly goes to step 133 if there is no change in commercial grade biologic information sensor 21.

In step S133, it is checked whether or not there is any change in home biologic information sensor 13, such as a new registration, deletion of registration or upgrading of sensor 13. The upgrading of sensor 13 includes an addition of some new function to sensor 13 with the registration thereof unchanged. If there is any change in sensor 13, the flow advances to step S134 to carry out "moving process", and the flow goes to step S135.

In the case of home biologic information sensor 13, new registration, deletion of registration or updating of the sensor relates not only to a simple upgrading of it, but also to moving of a family into or out of the condominium building in many case, which necessitates the "moving process" including arrangement or disposal of data in personal computer in the apartment. The detail of "moving process" will be explained later. On the other hand, if there is no change in home biologic information sensor 13, the flow directly goes to step 135

In step S135, it is checked whether or not there is any change in registration of patient, such as addition, deletion or alteration. If there is any change in the patient registration, the flow advances to step S136 to change data of host computer 22 to reflect the addition, deletion or alteration of the patient.

The addition, deletion or alteration of patient is caused in many cases by a patient who changes medical institution 9 into new one closer to the new residence or with other convenience. So, in step 137, necessary action is taken to pass or take over health control information between former and new medical institutions.

In other words, if a patient comes from another medical institution to medical institution 9 to cause a newly registration, the reference health control information and health control database with respect to the patient stored in a host computer of the former medical institution are taken over by reference biologic information register 23 and central health control database 27 of medical institution 9. On the contrary, if a patient leaves medical institution 9, the reference health control information and health control database with respect to the patient stored in reference biologic information register 23 and central health control database 27 are sent to a designated new medical institution with the originals are deleted from reference biologic information register 23.

However, if the addition, deletion or alteration of patient is not caused by a patient who changes medical institution, but caused by a birth or death of a patient or change in the family name of a patient upon marriage, the action in step S137 is omitted.

After the action in step S137, the flow advances to step 138. If there is no addition, deletion or alteration of patient, the flow directly goes to step S138.

In step S138, it is checked whether or not there is any change in reference information registered in reference biologic information register 23, such as addition, deletion or updating of the reference information. If there is any change in the registered reference information, the flow advances to step S139 to modify the registration in reference biologic information register 23 of host computer 22 to reflect the change in the reference information, and the flow goes to step S140. On the other hand, the flow directly goes to step 140 if there is no change in the reference information.

In step S140, it is checked whether or not there is any change in the registered request of a registered patient to deliver the statistics information of the patient on the basis of to the central health control database 27, such as addition, deletion or updating of the registered deliver request. If there is any change in the registered deliver request, the flow advances to step S141 to modify the registration of the registered request in host computer 22 to reflect the change in the registered request, and the flow goes to step S142. On the other hand, the flow directly goes to step 142 if there is no change in the registered request.

In step S142, host computer 22 comes into a condition of waiting the reception of biologic information to be sent from home biologic information sensor 13 or commercial grade biologic information sensor 21 under the patient agreement. Further in step S143, host computer 22 comes into a condition of waiting to start a process of sending various data such as the registered reference health information, the result of diagnosis, or the statistics information of the patient to his or her personal computer in an apartment. And then, the flow terminates the basic function.

Figure 12:
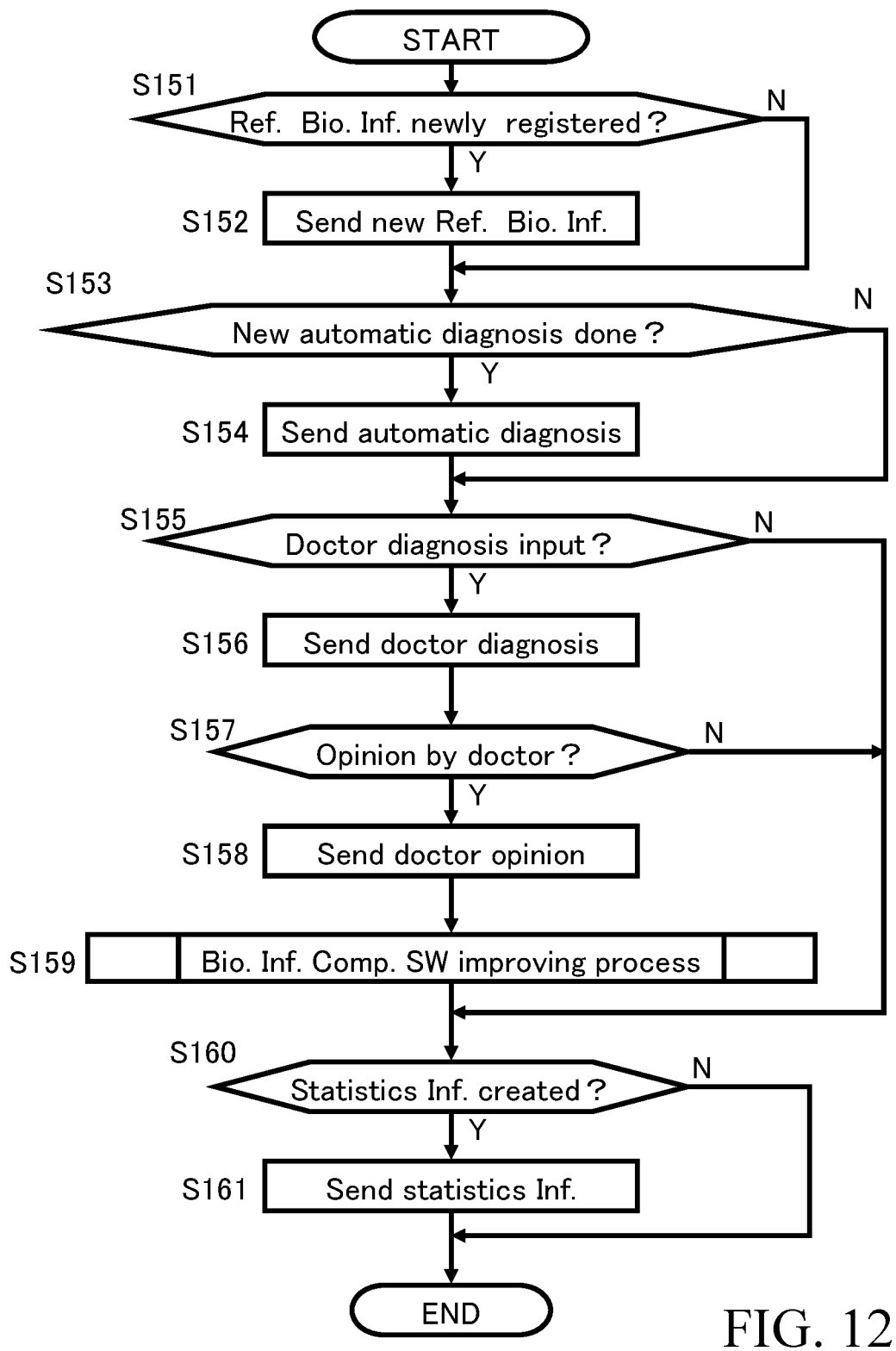
FIG. 12 is a flow chart regarding the data transmission process of the personal computer in the medical institution for the first embodiment.

FIG. 12 is a flow chart showing the basic function of host controller 26 of host computer 22 relating to the process of sending various data. The flow of the sending process in FIG. 12 is stated by various trigger with host controller 22 having come into the condition of waiting in step S143.

When the sending process is started, it is checked in step S151 whether or not the trigger is given by new reference health information of a patient is registered at reference biologic information register 23. If the new registration of reference health information has given the trigger, the flow advances to step S152 to send the newly registered reference health information to the personal computer of an apartment where the patient lives, and the flow advances to step S153. For example, if reference health information of a member of the family living in the first apartment is newly registered, host computer 22 sends the newly registered reference health information to the first personal computer 5, which in turn stores the received reference health information into reference health information holder 16. On the other hand, if the trigger is not caused by any new registration of reference health information, the flow directly advances to step S153.

In steps S153, it is checked whether or not the trigger is given by new automatic diagnosis of a patient made by biologic information comparing software 24 on the basis of central health control database 27. If the new automatic diagnosis has given the trigger, the flow advances to step S154 to send the new automatic diagnosis to the personal computer of an apartment where the patient lives, and the flow advances to step S155. On the other hand, if the trigger is not caused by any new automatic diagnosis, the flow directly advances to step S155.

In steps S155, it is checked whether or not the trigger is given by new diagnosis data of a patient entered by doctor 25 on the basis of central health control database 27. If the new diagnosis data entry has given the trigger, the flow advances to step S156 to send the new diagnosis of doctor 25 to the personal computer of an apartment where the patient lives.

Next, in steps S135, it is checked whether or not a diagnosis by doctor 25 includes an opinion inconsistent with the automatic diagnosis. If the diagnosis by doctor 25 includes some inconsistent opinion, the flow advances to step S158 to send a warning to the personal computer along with the inconsistent opinion by doctor 25 for the patient to note the inconsistency. Thus, the patient can put higher priority on the diagnosis and opinion by doctor 25 than the automatic diagnosis.

Further in steps S159, a process of improving biologic information comparing software 24 so as to remove the inconsistency in diagnosis on the basis of the reason of inconsistency is started, and the flow advances to step S160.

On the other hand, in step S155, if the trigger is not caused by any new diagnosis by doctor 25, the flow directly advances to step S160. There is no inconsistency of diagnosis in step 157, the flow also directly advances to step S160.

In steps S160, it is checked whether or not the trigger is given by new statistics information created on the basis of to the central health control database 27 for a patient who has requested the deliver of it. If the new creation of statistics information has given the trigger, the flow advances to step S161 to send the new statistics information along with the position of the patient in statistics information to the personal computer of an apartment where the patient lives, and the flow of the sending process is terminated. On the other hand, if the trigger is not caused by any new statistics information, the flow is instantly terminated.

Figure 13:
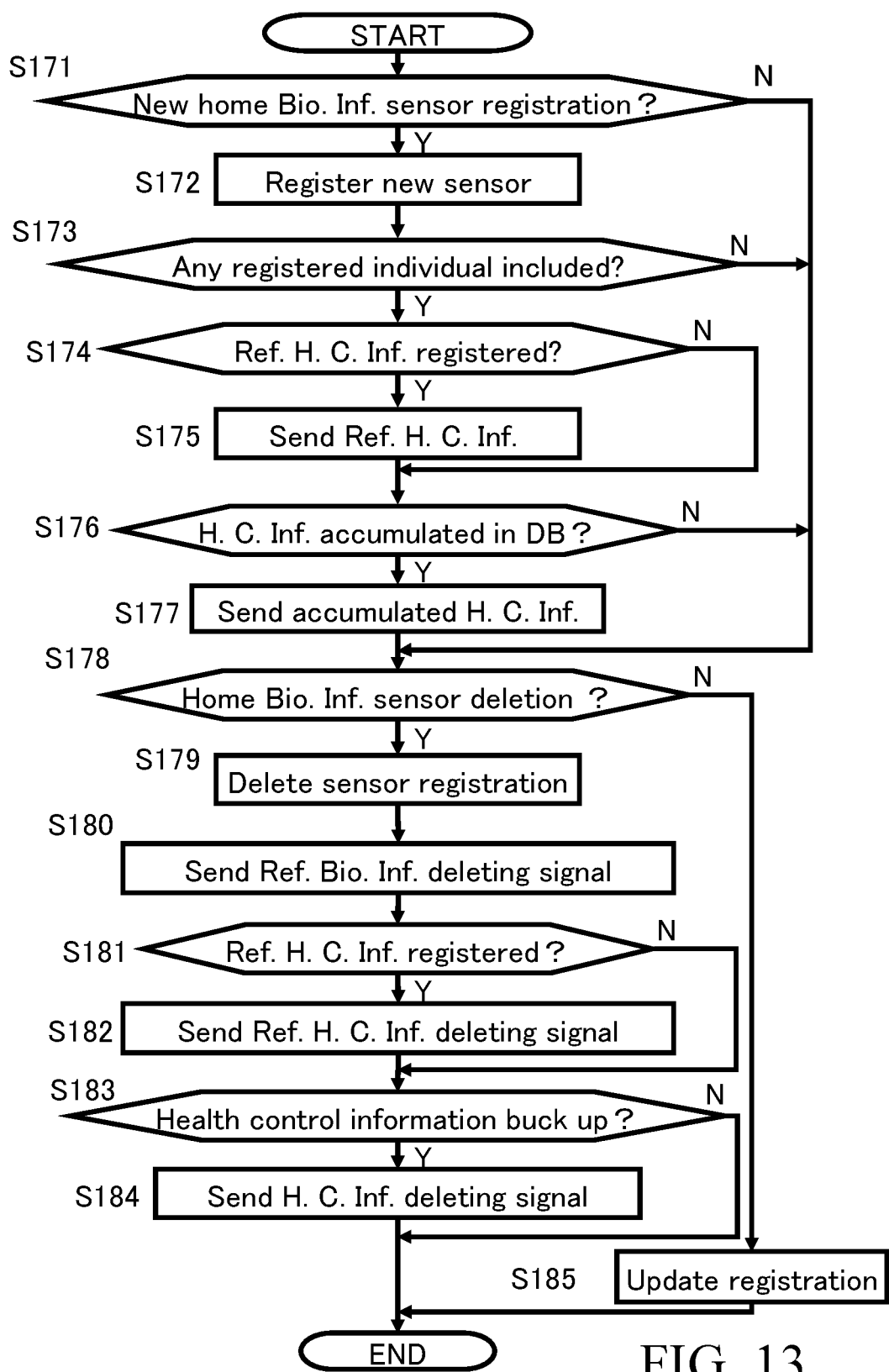
FIG. 13 is a flow chart showing the details of step 134 in FIG. 11 for the first embodiment.

FIG. 13 is a flow chart showing the details of "moving process" in step 134 of FIG. 11.

When "moving process" is started, it is checked in step S171 whether or not the change is a new registration of home biologic information sensor 13. If the change is a new registration, the flow advances to step S172 to register the new home biologic information sensor 13 into host computer 22 of medical institution 9. Thus, the new home biologic information sensor 13 comes under control of host computer 22. In other words, the health control information gotten by home biologic information sensor 13 is to be processed by host computer 22.

In steps S173, it is checked whether or not medical institution 9 has already registered a patient name identifying anyone of the newly registered family moving into the apartment where the newly registered home biologic information sensor 13 is located. This case is caused for example by a patient who has already registered his or her identification into medical institution 9 from the former address now moves into the first apartment 2 of condominium building 1 and requires the registration of home biologic information sensor 13 through the first personal computer 5.

If it is checked in step S173 that medical institution 9 has a registration identifying one the family, the flow advances to step S174 to check whether or not reference biologic information register 23 of host computer 22 possibly registers reference biologic information of the identified patient. And, if such reference biologic information is registered, the flow advances to step S175 to send the reference biologic information to the first personal computer 5, which stores the received reference biologic information into reference health information holder 16. After sending the reference information, the flow goes to step S176. If no reference biologic information is registered, however, the flow goes from step S174 directly to step S176.

In steps S176, it is checked whether or not host computer 22 has possibly stored the health control information of the identified patient in central health control database 27. And, if such health control information is stored, the flow advances to step S177 to send the health control information to the first personal computer 5, which stores the received health control information into individual health control database 15. Thus received past health control information is useful for the first personal computer 5 to locally check by itself the moment-to-moment change in the health control information of the identified patient. After sending the health control information, the flow goes to step S178. If no health control information is stored, however, the flow goes from step S176 directly to step S178.

If the change is not a new registration of home biologic information sensor 13 in steps S171, the flow directly goes to step S178. Also the flow directly goes from step S173 to step S178 if medical institution 9 has no registration identifying anyone of the family moving into the apartment where the newly registered home biologic information sensor 13 is located.

I it is checked in step S178 whether or not the change is a deletion of a registered home biologic information sensor 13. The necessity of such deletion will be caused for example by moving of the family out of the first apartment 2. If the change is the deletion of a registered home biologic information sensor 13, the flow advances to step S179 to delete the registration of home biologic information sensor 13 from host computer 22 of medical institution 9. Thus, the deleted home biologic information sensor 13 comes out of control of host computer 22.

Next, in steps S180, host computer 9 sends a reference biologic information deleting signal to the first personal computer 5, which deletes in response thereto all reference biologic information of the moving family from reference biologic information holder 14. Although medical institution 9 is not to do with the deletion of reference biologic information from reference biologic information holder 14 relating to authentication within condominium building 1 at all, medical institution 9 undertakes such a privacy protection service in "moving process" since the reference biologic information is deeply private information relating the same home biologic information sensor 13 which covers both admission authentication and health control.

Next in steps S181, it is checked whether or not reference biologic information register 23 of medical institution 9 registers reference biologic information of anyone of the moving family. And, if such reference biologic information is registered, host computer 22 itself keeps the registration within medical institution 9. In step S182, however, host computer 22 sends a reference biologic information deleting signal to the first personal computer 5, which deletes in response thereto all reference biologic information of the moving family from reference health information holder 16. After sending the reference biologic information deleting signal, the flow goes to step S183. If no reference biologic information is registered, however, the flow goes from step S181 directly to step S183.

In steps S183, it is checked whether or not host computer 9 backs up the health control information of all individuals of the moving family within central health control database 27. If the health control information is backed up, host computer 22 itself keeps the back up within medical institution 9 at central health control database 27. In step S184, however, host computer 22 sends a health control information deleting signal to the first personal computer 5, which deletes in response thereto all health control information of the moving family from individual health control database 15. After sending the health control information deleting signal, the flow goes to the end of "moving process". If there is no back up of health control information of the moving family in central health control database 27, however, the flow goes from step S183 directly to the end of "moving process".

If the change is not a deletion of a registered home biologic information sensor 13 in step S178, the flow advances to step S185 to update the registration of home biologic information sensor 13 since the change is mere an update of the same home biologic information sensor 13 without any new registration nor a deletion thereof in this case.

The first embodiment above has been explained as a case of a condominium building including a plurality of apartments where a plurality of families live in, respectively. However, the system such as in the first embodiment is not only applicable to the condominium, but also to a building containing a plurality of independent companies using a common entrance, or to a company located at a business place having a common entrance where a plurality of independent departments work, or the like.

Second Embodiment

Figure 14:
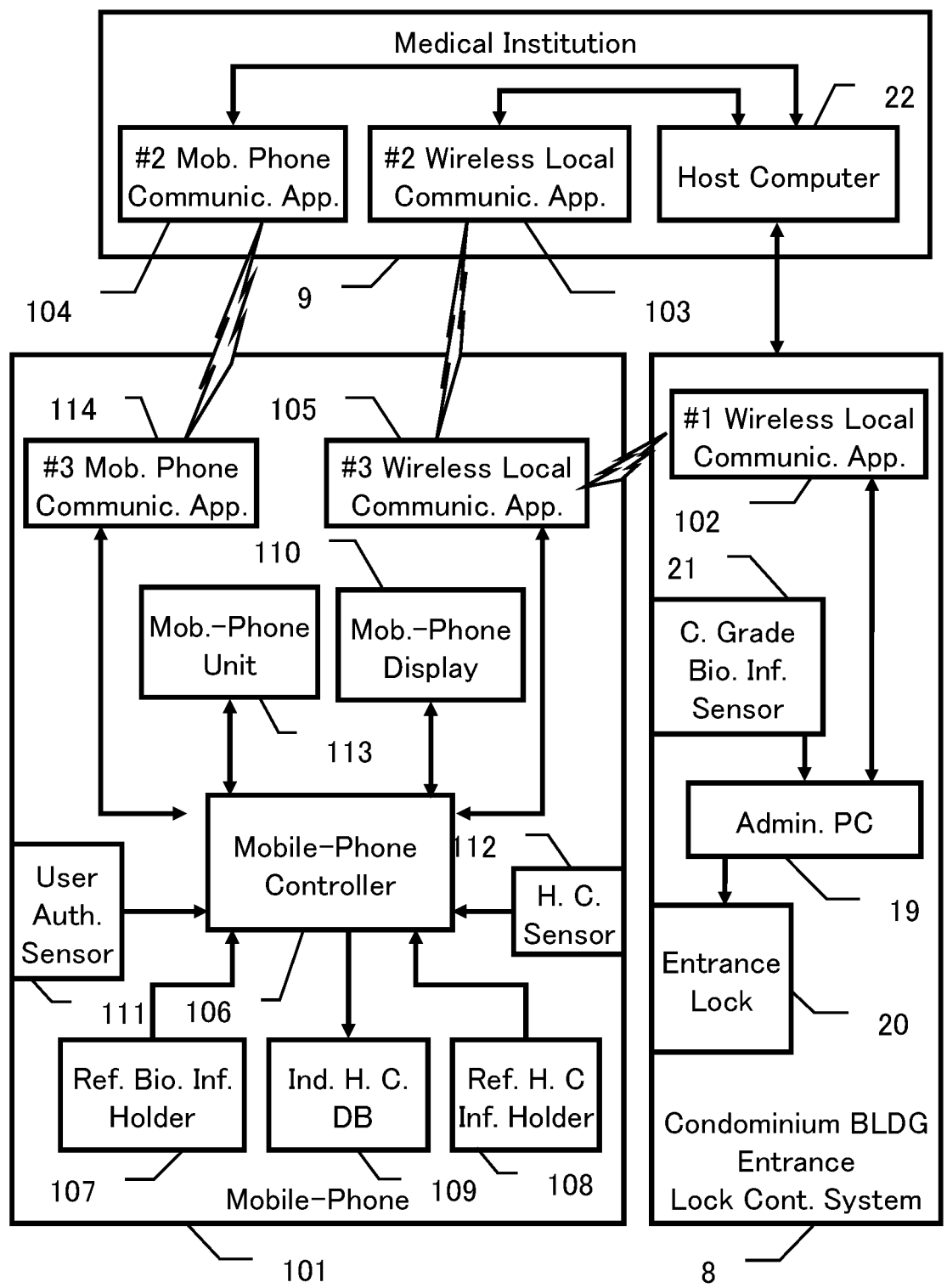
FIG. 14 is a block diagram of a biometrics and health controlling system according to a second embodiment of this invention.

FIG. 14 is a block diagram of a biometrics and health controlling system according to a second embodiment of this invention. The second embodiment does not differ from the first embodiment in that the system is embodied in a condominium building where a plurality of families domicile. In other words, the second embodiment also relates to a system for unlocking authentication both for the common entrance of the condominium building 1 and for the individual entrance door for the first apartment 2 or the like. But, the second embodiment is characterized by mobile-phone 101 incorporated in the system. Elements in condominium building entrance lock control system 8 and medical institution 9 which are common to both the embodiments are given with the same numeral with their explanation is basically omitted in FIG. 14.

The second embodiment also includes the individual entrance door lock control system for the first apartment 2 or the like. However, since the system for the first apartment 2 or the like is identical with condominium building entrance lock control system 8, the individual entrance door lock control system is not shown in FIG. 14 with its explanation omitted for avoiding duplication.

Condominium building entrance lock control system 8 of the second embodiment includes the first wireless local communication apparatus 102, such as Bluetooth (trademark) or wireless LAN or wireless USB.

Administration computer 19 of the second embodiment is in communication with the first personal computer 5 in the first apartment 2 or the like of condominium building 1 as in the first embodiment. Administration computer 19 of the second embodiment is further in communication with mobile-phone 101 through the first wireless local communication apparatus 102 for controlling entrance lock 20 and for processing health control information. The other elements of condominium building entrance lock control system 8 in the second embodiment are the same as those in the first embodiment. If necessary, however, condominium building entrance lock control system 8 may further include a first mobile-phone communication apparatus not shown.

Medical institution 9 of the second embodiment includes the second wireless local communication apparatus 103 and the second mobile-phone communication apparatus 104. The second wireless local communication apparatus 103 is governed by same wireless local communication system that governs the first wireless local communication apparatus 102. The second mobile-phone communication apparatus 104 is administrated by a mobile-phone carrier. The second mobile-phone communication apparatus 104 may be replaced by a broadband inter net connector.

Host computer 22 in medical institution 9 of the second embodiment is in communication with administration computer 19 of condominium building entrance lock control system 8 and the first personal computer 5 in the first apartment 2 or the like of condominium building 1 as in the first embodiment. Host computer 22 of the second embodiment is further in communication with mobile-phone 101 through the second wireless local communication apparatus 103 or the second mobile-phone communication apparatus 104. The other elements of medical institution 9 in the second embodiment are the same as those in the first embodiment.

In the second embodiment, a person who wants to unlock the entrance lock 20 is to approach the entrance of condominium 1 with mobile-phone 101. The authentication system can be triggered by presence sensor 58 sensing the approach of the person as in the first embodiment. Further in the second embodiment, the authentication can also be triggered by the first wireless local communication apparatus 102 sensing that mobile-phone 101 comes into the communication area of the wireless local communication system. The trigger will be actually caused by whichever comes first.

When commercial grade biologic information sensor 21 successfully get biologic information from an inserted finger, administration computer 19 sends the biologic information to mobile-phone 101 by way of the first wireless local communication apparatus 102. For receiving the biologic information, mobile-phone 101 includes the third wireless local communication apparatus 105 governed by same wireless local communication system that governs the first wireless local communication apparatus 102.

The third wireless local communication apparatus 105 send to mobile-phone controller 106 the biologic information gotten by commercial grade biologic information sensor 21. Mobile-phone controller 106 compares the received biologic information with reference biologic information previously stored in reference biologic information holder 107. If the result of the comparison identifies that the person is entitled to enter condominium building 1, mobile-phone controller 106 informs the administration computer 19 of the result by way of the third wireless local communication apparatus 105 and the first wireless local communication apparatus 102.

In response to the informed result, administration computer 19 sends an unlock signal to entrance lock 20. If the received biologic information does not coincides with the reference biologic information on the other hand, mobile-phone controller 106 informs the administration computer 19 of the negative result not to have administration computer 19 send any unlock signal to entrance lock 20.

As is apparent from the above, administration computer 19 of condominium building entrance lock control system 8 in the second embodiment has no function of storing the reference biologic information or comparing it with the sensed biologic information, but has a function of being informed of the mere result of comparison from mobile-phone 101, which is similar to the case in the first embodiment. Thus, the reference biologic information such as the pattern of blood vessel or eye-fundus, which is of high privacy, will not leak out of mobile-phone 101. Further, the feature similar to the first embodiment that administration computer 19 has no function of comparison by itself nor is informed of whose mobile-phone sends the comparison result is a good proof of protecting privacy.

Similarly to the case in first embodiment, commercial grade biologic information sensor 21 in the second embodiment is capable of getting biologic information not only for authentication but also for health control. So, health control through commercial grade biologic information sensor 21 is possible also in the second embodiment.

In other words, the biologic information gotten by commercial grade biologic information sensor 21 and sent to mobile-phone controller 106 by way of the first wireless local communication apparatus 102 and the third wireless local communication apparatus 105 includes health control information such as blood component and blood vessel youth. Mobile-phone controller 106, accordingly, compares these health control information with the reference health control information of the keeper of mobile-phone 101, which information is registered in reference health information holder 108.

As in the first embodiment, reference health information holder 108 holds not only instantaneous value of the reference information but also change in it over time. Thus, mobile-phone controller 101 not only compares instantaneous value of the information sent from commercial grade biologic information sensor 21 with the instantaneous value of the reference information held by reference health information holder 108. But also, mobile-phone controller 101 compares the change in information sent from commercial grade biologic information sensor 21 and stored in individual health control database 109 with the reference change information held in health information holder 108. Thus, the health control is possible also in view of the speed of the change in information sensed by commercial grade biologic information sensor 21 over time. The results of comparison between the instantaneous values of information and of the comparison between the changes in information are displayed on mobile-phone display 110. In case of abnormality as a result of the comparison, it is advantageous to make a beep tone accompany the display of abnormality for the keeper of mobile-phone 101 to note the mobile-phone display 110.

Mobile-phone 101 further includes user authentication sensor 111 of the same function as in user authentication sensor 18 of the first embodiment. Thus, upon user authentication in using conventional mobile-phone function, it is possible to get biologic information both for authentication and for health control.

Mobile-phone 101 also includes health control sensor 112 for sensing biologic information during the keeper is talking on the phone. Information gotten by health control sensor 112 is also useful for health control as well as the information from commercial grade biologic information sensor 21 and user authentication sensor 111. Example of health control sensor 112 is a breath component sensor located close to the microphone or an ear thermometer combined with the speaker or earphone. Health control sensor 112 need not have a function of getting biometrics information, but a function of getting only health control information is sufficient.

Mobile-phone 101 is further capable of receiving health control information sent from an outside health control sensor to the third wireless local communication apparatus 105 for use the information as well as health control sensor 112. The outside health control sensor is advantageously combined with one of various accessories that the keeper of mobile-phone wears, such as a wristwatch, a belt, a pair of glasses, and shoes.

The third wireless local communication apparatus 105 is also capable of receiving health information from an outside health control sensor that does not accompany mobile-phone 101, but temporally comes close to mobile-phone, such as a health control sensor incorporated into a chair with massager.

The third wireless local communication apparatus 105 is still further capable of receiving health information from not only the above mentioned outside health control sensor incorporated into a product having other primary function, but also from an exclusive use health control sensor such as an automatic blood pressure monitor located at a waiting lounge of medical institution 9 if such a blood pressure monitor has the second wireless local communication apparatus 103 to send the monitored blood pressure. The health control information received by the third wireless local communication apparatus 105 from the additional or exclusive health control sensors as well as commercial grade biologic information sensor 21 is stored into individual health control database 109. The health control information from user authentication sensor 111 and health control sensor 112 within mobile-phone 101 is also stored into individual health control database 109.

The health control information received through the third wireless local communication apparatus 105 and gotten by user authentication sensor 111 and health control sensor 112 is utilized without any comparison with the reference biologic information as well as the utilization though the comparison explained above. In other words, it is possible to display on mobile-phone display 110 a graph plotting the moment-to-moment change in the biologic information accumulated in individual health control database 109, such graph including no result of any comparison. Further, the received or gotten health control information as it is without any comparison can be displayed in real time on mobile-phone display 110.

Such a graph plotting the moment-to-moment change in the biologic information or a real time biologic information as it is can be displayed on the monitor of television set 17 of the first embodiment in FIG. 1.

Mobile-phone 101 of the second embodiment in FIG. 14 of course includes conventional mobile-phone unit 113 and the third mobile-phone communication apparatus 114. Explanation of the conventional function of these conventional elements is basically omitted.

Mobile-phone 101 includes a main power switch, which is not shown in FIG. 14, for deactivate conventional function including mobile-phone unit 113 and the third mobile-phone communication apparatus 114. The third wireless local communication apparatus is, however, not deactivated even if the main power switch is shut down. So, the third wireless local communication apparatus 105 is capable of receiving health information from the automatic blood pressure monitor located at a waiting lounge of medical institution 9 even if the main power switch is shut down in compliance with the instruction of medical institution 9.

The third mobile-phone communication apparatus 114 of mobile-phone 101 is administrated by a mobile-phone carrier which can cover communication with the second mobile-phone communication apparatus 104. Therefore, mobile-phone 101 can communicate with medical institution 9 far away through internet on mobile-phone or broadband network to exchange health control information. For example, the contents of individual health control database 109 can be sent to medical institution 9 in real time for back up. Or, the reference biologic information, health control information and diagnosis or the like of the keeper of mobile-phone 101 can be delivered from medical institution 9 to mobile-phone 101. Thus, mobile-phone 101 has almost the same functions as those of the first personal computer 5 or the like in the first embodiment, the privacy protection being strictly kept within each keeper of mobile-phone in comparison with the case of the first computer 5 or the like which may be commonly owned by a plurality of persons in a family.

The information exchange between mobile-phone 101 and medical institution 9 can be made not only through the second mobile-phone communication apparatus 104 and the third mobile-phone communication apparatus 114, but also through the second wireless local communication apparatus 103 and the third wireless local communication apparatus 105. The latter information exchange is possible when the keeper visits medical institution 9 as a patient who wants to make the registration of its reference biologic information.

The flow of functions carried out by mobile-phone controller 106 in FIG. 14 is basically identical with the flow in FIG. 7. In place of step S70 in FIG. 7, however, mobile-phone controller 106 prepares for display on mobile-phone display 110 so that an indication of the abnormality is to be automatically made when its power switch is turned on.

The flow of functions carried out by administration computer 19 of condominium building entrance lock control system 8 in FIG. 14 is basically identical with the flow in FIG. 10. In place of step S117 in FIG. 10, however, administration computer 19 sends the sensed biologic information only to the third wireless local communication apparatus 105 of mobile-phone 101.

The system including mobile-phone as in the second embodiment in FIG. 14 is applicable not only to the unlock authentication system for a condominium building or a building containing a plurality of independent companies, but also to a biometrics system for authenticating a person who is to access money or information, such as a deposit withdrawal handling system of a bank.

For understanding how to apply the second embodiment in FIG. 14 to a deposit withdrawal handling system of a bank, "deposit withdrawal handling machine 8" is substituted for "condominium building entrance lock control system 8", "identical person sensor 21 for deposit account" for "commercial grade biologic information sensor 21", and "deposit withdrawal admission part 20" for "entrance lock 20" in FIG. 14, respectively.

In FIG. 14 with the above substitutions made, if a person who wants to withdraw money form his or her deposit account is to approach "deposit withdrawal handling machine 8", the authentication system is triggered to start communication between the first wireless local communication apparatus 102 and the third wireless local communication apparatus 105. When the person inserts his or her finger into "identical person sensor 21 for deposit account", the sensed biologic information is sent to mobile-phone 101 for comparison with the reference biologic information. If the result of the comparison identifies that the person is entitled to withdraw money from the own deposit account, mobile-phone controller 106 informs the administration computer 19 of the result for transmission of an admission signal to "deposit withdrawal admission part 20", which makes it possible for the person to withdraw money. Thus, bank itself does not keep the reference biologic information nor makes the comparison of the biologic information, the privacy of the reference biologic information is kept within mobile-phone 101.

The biologic information gotten by "identical person sensor 21 for deposit account" and sent to mobile-phone 101 include not only the authentication information but also health control information, mobile-phone 101 can utilize it in such a manner of displaying it or accumulate it or comparing it with reference health control information in mobile-phone 101. Thus, the bank can provide an additional service of getting useful health control information to the original service of high security of biometrics for deposit withdrawal.

Now the detail of the procedure of registering new reference biologic information is to be explained.

Figure 15:
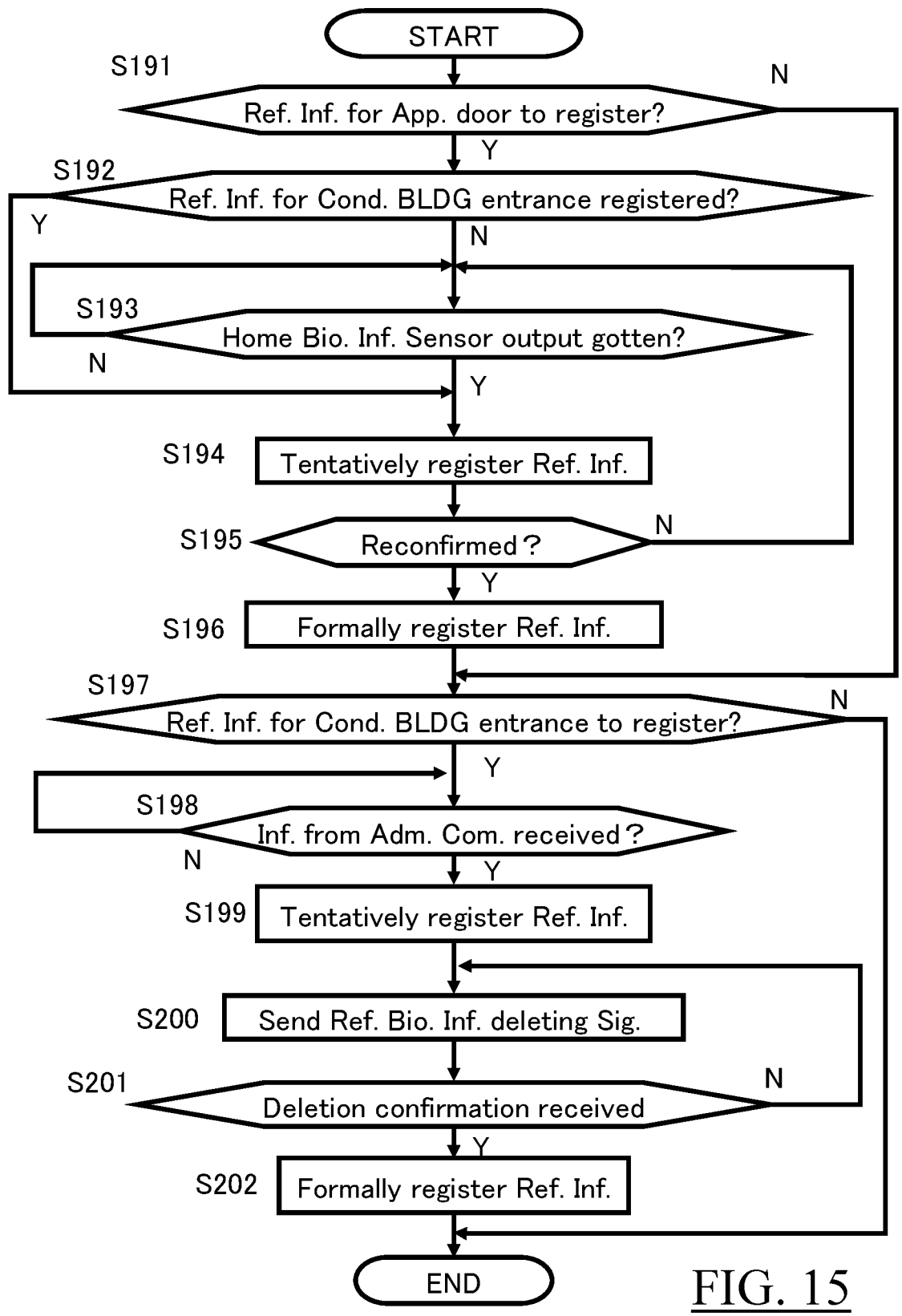
FIG. 15 is a flow chart showing the details of step 11 in FIG. 4 for the first embodiment.

With respect to the case of the first embodiment, FIG. 15 represents the detail of the procedure of registering new reference information into reference biologic information holder 14 of the first personal computer 5. If the flow starts, it is checked in step S191 whether or not a registration of new reference information for unlocking entrance door 10 of the first apartment 2 is requested. If the new registration is requested, the flow advances to step S192 to check whether or not some reference information for unlocking entrance lock 20 of condominium building 1 is registered in reference biologic information holder 14.

If any reference information for entrance lock 20 is not been registered, the flow advances to step S193 to wait biologic information to be gotten by home biologic information sensor 13. The biologic information is to be gotten by inserting a finger of an identified person into home biologic information sensor 13. If the biologic information is gotten, the flow advances to step S194 to tentatively register the gotten biologic information.

On the other hand, if it is detected in step S192 that some reference information for entrance lock 20 is registered in reference biologic information holder 14, the flow directly advances to step S194 to tentatively register the biologic information which is a copy of the registered reference information for entrance lock 20 in reference biologic information holder 14 since such a registered reference information for entrance lock 20 for condominium building 1 may possibly be used also as the reference information for entrance door 10 of the first apartment 2.

Next, in step S195, it is checked whether or not biologic information newly gotten by home biologic information sensor 13 with the finger of the identified person inserted for confirmation is identical with the tentatively registered reference biologic information. If the identification is successful in step S195, the flow advances to step S196 to formally register into biologic information holder 14 the tentative registration of the reference biologic information. On the other hand, if the identification is failed in step S195, the flow returns to step S193 to wait new biologic information gotten by home biologic information sensor 13 with the finger of the identified person inserted again. Thus, the loop of the tentative registration from step S193 to step S195 is repeated unless the identification is successful in step S195. In the case that the flow comes from step S192 directly to step S194 with step S193 initially skipped, the flow also enters the loop if the identification is failed in step S195.

After the formal registration of the reference information for entrance door 10 of the first apartment 2, the flow advances to step S197. If it is determined in step S191 that any new registration of reference information for unlocking entrance door 10 of the first apartment 2 is not requested, which means that the formal reference information has been already registered in reference biologic information holder 14, the flow directly advances from step S191 to step S197.

In step 197, it is checked whether or not a registration of new reference information for unlocking entrance lock 20 of condominium building 1 is requested. If the new registration is requested, the flow advances to step S198 to wait biologic information to be sent from administration computer 19. The reference biologic information is to be gotten by inserting a finger of an identified person into commercial grade biologic information sensor 21 at condominium building entrance lock control system 8. The reference biologic information to be sent from administration computer 19 has already been certified by condominium building entrance lock control system 8. If the biologic information is sent from administration computer 19, the flow advances to step S199 to tentatively register the reference biologic information received from administration computer 19.

Next in step S200, a deletion signal is sent to administration computer 19 to delete from administration computer 19 itself the reference biologic information gotten by commercial grade biologic information sensor 21. And then, the first personal computer 5 waits deletion confirmation to be returned by administration computer 19 in step S201. If the confirmation is received in step S201, the flow advances to step S202 to formally register into biologic information holder 14 the tentative registration of the reference biologic information for unlocking entrance lock 20 of condominium building 1, and the registration flow is terminated. On the other hand, if the confirmation is failed to be received in step S201, the flow retunes to step S200 to send the deletion signal again to administration computer 19.

Thus, the deletion the original reference biologic information from administration computer 19 is parallel to the formal registration of the transmitted biologic information at the first computer 5. This means that the creation of reference biologic information for entrance lock 20 of the condominium building 1 is exclusively possible under the control of condominium building entrance lock control system 8 for preventing the reference biologic information form being forged at the first apartment 2 or the like, and that the keeping of the reference biologic information, on the other hand, is exclusively possible under the control of the first apartment 2 for preventing the reference biologic information from leaking through condominium building entrance lock control system 8 infringing the privacy. Further, it should be noted, that the original reference biologic information is kept in condominium building entrance lock control system 8 if the formal registration of the received reference biologic information into reference biologic information holder 14 is failed.

For the purpose of securing the prevention of the reference biologic information form being forged outside condominium building entrance lock control system 8, the biologic information gotten by commercial grade biologic information sensor 21 is encrypted when sent to the first personal computer 5 or the like. So, the comparison made outside condominium building entrance lock control system 8 cannot match real biologic information originated by condominium building entrance lock control system 8 with any forged biologic information.

In step S197 it is determined that no new registration of the reference biologic information for condominium building entrance lock control system 8 is requested, the flow is instantly terminated.

In the flow in FIG. 15, the necessity of new registration for authentication is checked firstly for entrance door 10 of the first apartment 2, and secondary for entrance lock 20 of condominium building 1. The order of check may be reversed. In other words, steps S197 to S202 may precede step 191 in FIG. 15.

With respect to the function flow for controller 12 to newly register the reference biologic information for user authentication sensor 18 in FIG. 1 is similar to the flow of step S191 to step S196. However, the steps should be understood with "user authentication" substituted for "entrance door" in step S191, and "user authentication sensor" for "home biologic information sensor" in step S193, respectively.

With respect to the function flow for mobile-phone controller 106 of the second embodiment in FIG. 14 to newly register the reference biologic information into reference biologic information holder 107 is similar to the entire flow in FIG. 15 with the above substitution in steps S191 and S193 made.

Figure 16:
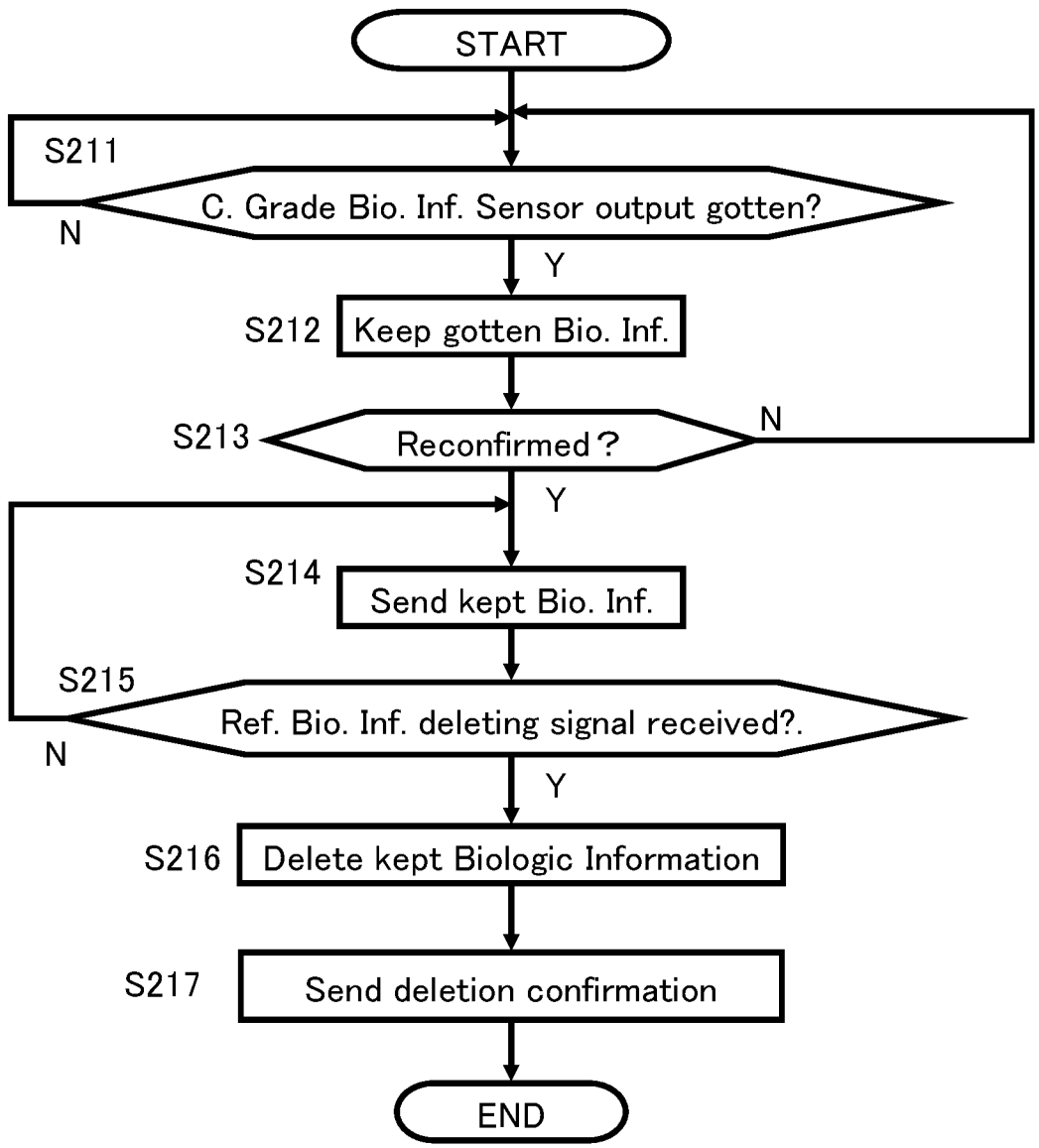
FIG. 16 is a flow chart showing the details of step 110 in FIG. 9 for the first embodiment.

FIG. 16 represents the detail of the procedure of registering new reference information carried out in step S110 in FIG. 9 showing a flow chart showing the basic function of administration controller 53 of administration computer 19 located at condominium building entrance lock control system 8. If the flow starts, administration controller 53 in step S211 waits biologic information to be gotten by commercial grade biologic information sensor 21. The biologic information is to be gotten if an identified person inserts a finger into commercial grade biologic information sensor 21 for the purpose of registering the reference biologic information. If the biologic information is gotten, the flow advances to step S212 to tentatively keep the gotten biologic information.

Next, in step S213, it is checked whether or not biologic information newly gotten by commercial grade biologic information sensor 21 with the finger of the identified person inserted for confirmation is identical with the tentatively kept reference biologic information. If the identification is successful in step S213, the flow advances to step S214 to send the tentatively kept reference biologic information to the first personal computer 5 as the certified reference biologic information. On the other hand, if the identification is failed in step S213, the flow returns to step S211 to wait new biologic information gotten by commercial grade biologic information sensor 21 with the finger of the identified person inserted again. Thus, the loop of getting certified reference biologic information from step S211 to step S213 is repeated unless the identification is successful in step S213.

After sending the certified reference biologic information in step S214, administration computer 19 waits the deletion signal from of the first personal computer 5 to delete the reference biologic information kept in administration computer 9. The deletion signal from the first personal computer 5 means an acknowledgement of receipt of the certified reference biologic information.

If the deletion signal is received in step S215, the flow advances to step S216 to delete the kept reference biologic information. And then the flow advances to step S217 to send the deletion confirmation to the first personal computer 5, and the flow goes to the end. On the other hand, if the deletion signal is failed to be received in step S215, the flow retunes to step S214 to send the certified reference biologic information to the first personal computer 5.

Thus, in the case of unlock authentication of common entrance of condominium building 1, the creation of reference biologic information is made under the control of condominium building entrance lock control system 8 for preventing the reference biologic information form being forged, while the keeping of the reference biologic information is not made by condominium building entrance lock control system 8, but by the first apartment 2 for preventing infringement of the privacy.

In the case of unlock authentication of individual apartment, on the contrary, the registration process is simpler since the reference biologic information gotten by home biologic information sensor 13 scarcely leaks out of the first apartment 2.

With respect to the function flow for administration computer 19 of the second embodiment in FIG. 14 to newly get the reference biologic information at commercial grade biologic information sensor 21 and sent it to reference biologic information holder 107 of mobile-phone 101 is similar to the flow in FIG. 16. However, the above explanation should be understood with "mobile-phone 101" substituted for "the first personal computer 5.

In the above embodiments explained with respect to FIGS. 15 and 16, the registration of the reference biologic information for condominium building entrance lock control system 8 is made on the basis of the information gotten by commercial grade biologic information sensor 21. However, it is theoretically possible to make the registration of the reference biologic information for condominium building entrance lock control system 8 on the basis of the information gotten by home biologic information sensor 13 or user authentication sensor 111 if the function thereof is similar to that of commercial grade biologic information sensor 21 in terms of getting the reference biologic information for condominium building entrance lock control system 8.

In this case, however, it is necessary for administration computer 19 to make the first personal computer 5 under its strict control including exchange of decryption key or the like for preventing forged reference biologic information outside condominium building entrance lock control system 8.

Third Embodiment

Figure 17:
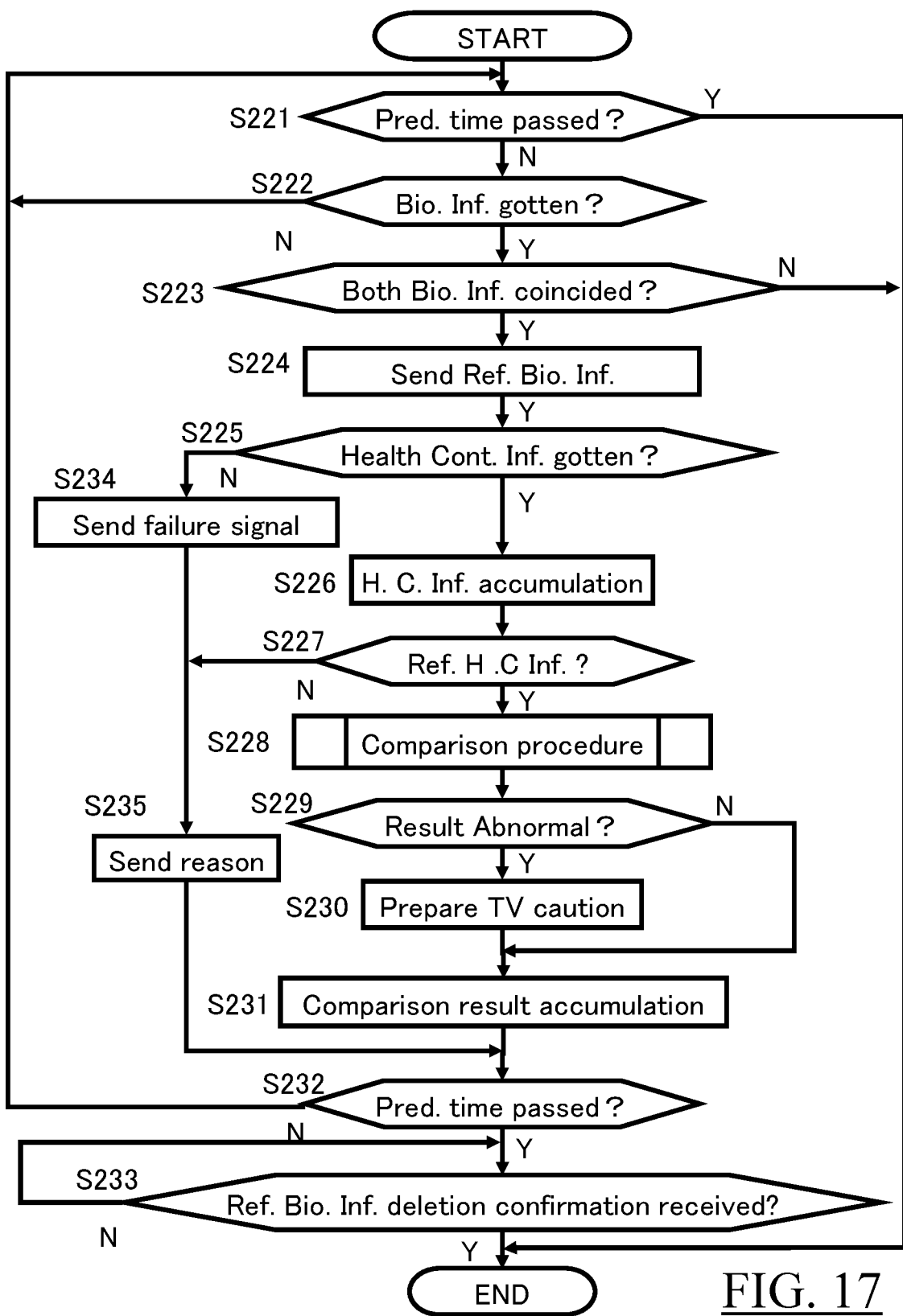
FIG. 17 is a flow chart of the personal computer located in the condominium apartment with the authentication system triggered at the entrance of the condominium building for the third embodiment.

FIG. 17 is a flow chart relating to a biometrics and health controlling system according to a third embodiment of this invention. The block diagram of the biometrics and health controlling system according to the third embodiment is similar to that of the first embodiment. So, the explanation of the third embodiment is to be made also with FIG. 1 used. In the third embodiment, however, the functions of the first personal computer 5 and of administration computer 19 differ from those in the first embodiment. In other words, the comparison of the biologic information for authentication in condominium building entrance lock control system 8 is made by the first personal computer 5 and the result of comparison is sent to administration computer 19 in the first embodiment. In the third embodiment, on the contrary, the comparison of the biologic information for authentication is made by administration computer 19 which receives the reference biologic information from the first personal computer 5. The details are to be explained with respect to the flow charts in FIGS. 17 and 18.

Controller 12 of the first personal computer 5 in the third embodiment functions in accordance with the flow in FIG. 17 in place of the flow in FIG. 7 in cooperation with condominium building entrance lock control system 8.

The authentication flow in FIG. 17 is triggered if the first personal computer 5 is informed by administration computer 19 of a person coming to stand in front of the entrance of condominium building 1. If the authentication is triggered, it is checked in step S221 whether or not a predetermined time has passed after authentication starts. If the time has not passed yet, the flow advances to step S222 in which it is checked whether or not the biologic information of the finger gotten by commercial grade biologic information sensor 21 is received. If no biologic information is received, the flow goes back to step S221, and steps S221 and S222 are repeated waiting for the receipt of the biologic information of the finger for the predetermined time.

If the receipt of the biologic information of the finger is detected in step S222, the flow goes to step S223 in which the received biologic information of the finger is compared with the reference biologic information stored in reference biologic information holder 14. It should be noted that the comparison in step S223 is not for unlock authentication for entrance lock 20 of condominium building 1, but for confirmation that the finger is of one of the family living in the first apartment 2. If the received biologic information coincides with the reference biologic information, the flow advances to step S224 to send to administration computer 19 the reference biologic information stored in reference biologic information holder 14. The unlock authentication hereinafter including the comparison process is left to administration computer 19.

Thus, the determination of the receipt of the biologic information in step 222 and its comparison in step S222 constitute the cause to send to administration computer 19 the reference biologic information stored in reference biologic information holder 14. In other words, only one apartment if any can send the reference biologic information.

Upon sending the reference biologic information in step S224, it is concealed from administration computer 19 that the reference biologic information is sent from the first personal computer 5 so that administration computer 19 cannot identify whose reference biologic information is sent.

Next, in step 225, it is checked whether or not commercial grade biologic information sensor 21 succeeds in getting sufficient information for health control. In other words, it is checked whether or not the biologic information received from administration computer 19 is sufficient as the health control information. A case of failure in step S225 means that the biologic information received from administration computer 19 is sufficient for the purpose of confirmation of identity, but is insufficient for the purpose of health control.

If it is judged that in step S225 that biologic information received from administration computer 19 is sufficient as the health control information, the flow advances to step S226 in which the received biologic information is stored into individual health control database 15. The information stored in individual health control database 15 is also sent to host computer 22 in real time for the storage in central health control database 27 according to a contract with medical institution 9. This means that the information in individual health control database 15 is backed up by central health control database 27, which makes it easy for moving out of condominium building 1 without losing individual health control database.

The above mentioned contract with medical institution 9 to send the health control information to host computer 22 in real time for the storage in central health control database 27 serves as a care system for solitary old people for example. Since the health control information is automatically sent to medical institution 9 every time when an inhabitant successfully goes through the entrance of the condominium building 1 according to such a contract, medical institution 9 can sense no passage of the inhabitant through the entrance of condominium building 1 for a considerable period of time by means of no sending of the health control information for the period of time. Thus, medical institution 9 can take necessary step as soon as it senses such an abnormal life pattern of the inhabitant.

Next, in step S227, it is checked whether or not reference biologic information exists in reference health information holder 16. If there is any reference biologic information, the flow advances to step S228 in which the received biologic information is compared with the reference biologic information in reference health information holder 16. And, the flow goes to step S229 to judge whether the result of comparison show any abnormality of health control information. If some abnormality detected, the flow advances to step S230 to prepare for display on television set 17 so that an indication of the abnormality is to be automatically made when its power switch is turned on, and the flow goes to step S231. If there is no abnormality judged in step S229, the flow directly goes to step S231.

In step S231, the comparison result is gotten in step S228 is stored in individual health control database 15. The information stored in individual health control database 15 in step S231 is also sent to host computer 22 in real time for the storage in central health control database 27. The abnormality judged in step S229 is also sent to host computer 22 in real time for the storage in central health control database 27.

By way of the above steps, the flow comes to step S232 to check again whether or not a predetermined time has passed after the authentication starts. The meaning of step S232 is similar to that of step S72 in FIG. 7.

If it is detected in step S227 that there is no reference biologic information in reference health information holder 16, the flow goes to step S232 by way of step S235 since there is no necessity of carrying out steps S228 to S231. In step 235 in this case, the fact that there is no reference biologic information in reference health information holder 16 is sent to administration computer 19, which is the reason why steps S228 to S231 have not been carried out.

In step S233, the first personal computer 5 comes into a condition of waiting the deletion confirmation from administration computer 19 reporting that the reference biologic information sent from the first personal computer 5 has been deleted from administration computer 19, and the flow goes to the end of authentication process. In other word, the authentication process will not end unless the deletion confirmation comes from administration computer in step S233 for preventing privacy violation.

On the other hand, if it is determined that the received biologic information is insufficient as the health control information, the fact is sent to administration computer 19 in step S234, the reason of which is also sent in step S235 prior to getting to step S232.

In step S221, if the predetermined time has passed after the authentication starts without insertion of a finger into commercial grade biologic information sensor 21, the flow instantly goes to the end.

In step S223, if the received biologic information does not coincide with the reference information stored in reference biologic information holder 14, the flow instantly goes to the end without sending any reference biologic information to administration computer 19 since the received biologic information from administration computer 19 has no relation to the family in the first apartment 2. Of course, the health control process of steps S225 to S231 is unnecessary since the received biologic information is of a complete stranger in this case. Further, the first personal computer 5 does not inform administration computer 19 of the result of comparison made in step S223 in this case since the responsibility of authentication for unlocking the entrance of condominium building 1 is not on the personal computer 5, but on administration computer 19.

Figure 18:
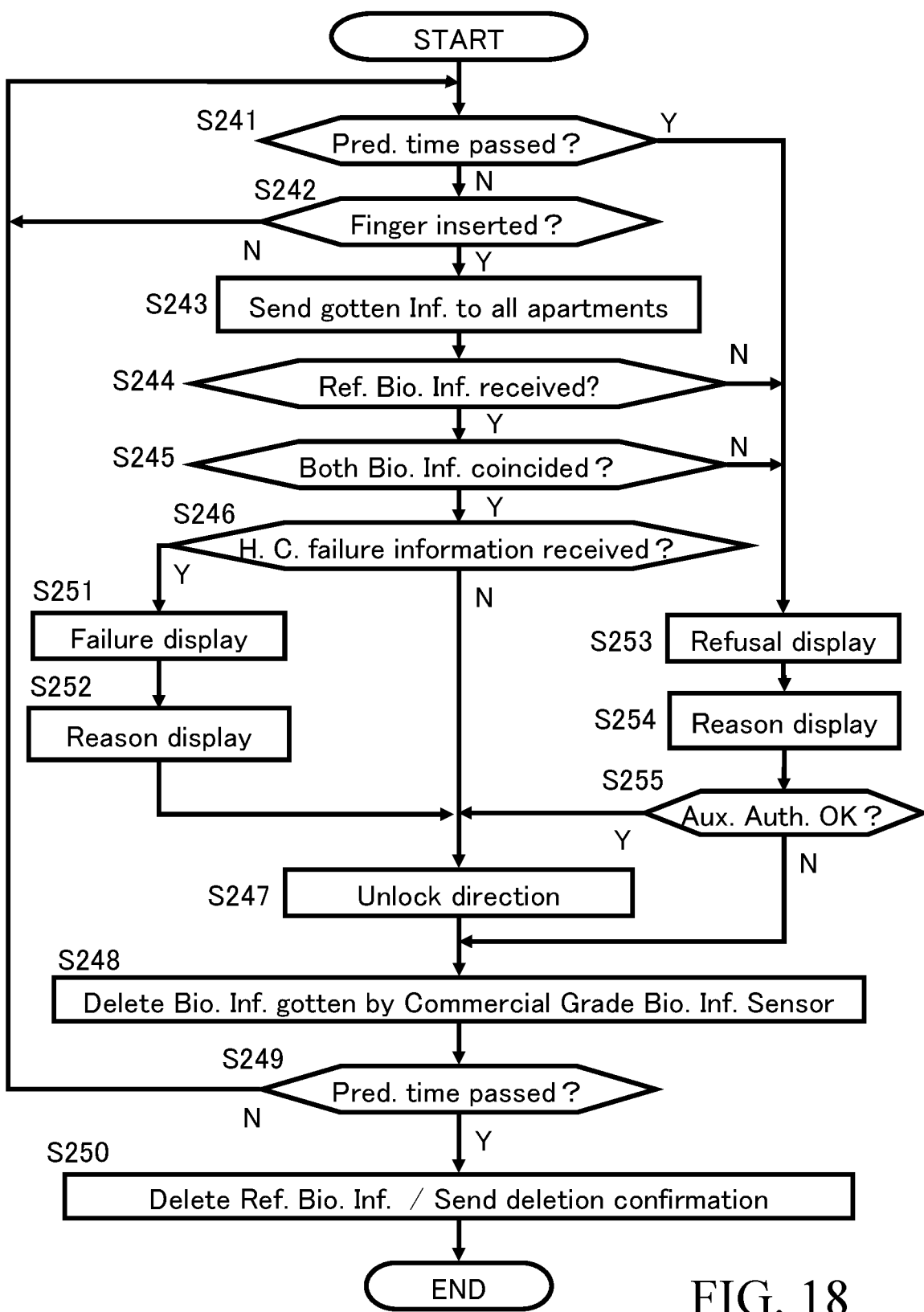
FIG. 18 is a flow chart of the personal computer located in the administration center of the condominium building with the authentication system triggered at the entrance of the condominium building for the third embodiment.

Administration controller 53 of the administration computer 19 in the third embodiment in FIG. 3 functions in accordance with the flow in FIG. 18 in place of the flow in FIG. 10.

The authentication flow in FIG. 18 is triggered if administration computer 19 detects a person coming to stand in front of the entrance of condominium building 1. If the authentication is triggered, it is checked in step S241 whether or not a predetermined time has passed after authentication is triggered. If the time has not passed yet, the flow advances to step S242 in which it is checked whether or not a finger is inserted into commercial grade biologic information sensor 21. If no finger is inserted, the flow goes back to step S241, and steps S241 and S242 are repeated waiting for the insertion of a finger for the predetermined time.

If the insertion of a finger is detected in step S242, the flow goes to step S243 in which the sensed biologic information from the finger is sent to all the apartments joining condominium building entrance lock control system 8. And, in step S244 it is checked whether or not reference biologic information is received from any of the apartments which detects that the sent biologic information coincides with reference biologic information. If it is determined in step 244 that reference biologic information is received from one of the apartments, the flow advances to step S245.

It should be noted that administration computer 19 does carry out the comparison in the third embodiment. In other words, administration computer 19 compares in step S245 the reference information having been received in step 244 and the biologic information sensed by commercial grade biologic information sensor 21. If both the biologic information coincide with each other in step S245, the flow goes to step S246.

In step S120, it is checked whether or not administration computer 19 is informed of a failure of getting health control information by any of the apartments.

If no failure information is received from any apartment in step 246, the flow advances to step S247 to direct entrance lock 20 to unlock the entrance door. Entrance lock 20 unlocks the entrance door in response to the direction.

In receiving information in steps S244 to S246, administration computer 19 is blocked from identifying a specific apartment that sends the reference biologic information and the failure information for the purpose of privacy protection.

After the direction to entrance lock 20, the flow advances to step S248 to delete the biologic information which has been gotten in step S242. This is to secure privacy protection. And, the flow advances to step 249 to check again whether or not a predetermined time has passed after the person comes to stand in front of the entrance of condominium building 1 to trigger the authentication. If the time has passed, the flow goes to step 250 to delete the reference biologic information having been received in step S244 and to inform all the apartments of the deletion confirmation, and then administration computer 19 terminates the authentication flow.

On the other hand, in step S246 if it is checked that administration computer 19 is informed of a failure of getting health control information by any of the apartments, the flow advances to step S251 to display the fact of failure, the reason of failure being also displayed in step S252 prior to getting to step S247. Thus, also in condominium building entrance lock control system 8, the direction is made toward entrance lock 20 to unlock the entrance door of condominium building 1 even if it is failed to get health control information in the apartment.

If it is checked in step S241 that the predetermined time has passed after the person comes to stand in front of the entrance of condominium building 1 without any insertion of a finger into commercial grade biologic information sensor 21, the flow advances to step 253 to display admission refusal indication. Further, the indication of the reason of refusal is displayed in step S254, the reason being the non-insertion of a finger in this case. And then, the flow goes to step S255.

In step S255, auxiliary conventional authentication system such as password system or IC card system is made available to check whether or not such an auxiliary conventional authentication is successful. It the auxiliary conventional authentication is successful, the flow advances to step S247 to unlock entrance lock 20. If the auxiliary conventional authentication is not made or unsuccessful, the flow finally goes to the end by way of steps S248 to S250, entrance lock 20 being not unlocked. With only this case taken into consideration, step S247 may seem to have no meaning since there is no necessity of deleting any biologic information which has not been gotten in first place. However, step S248 is located at the position shown in FIG. 18 for protecting privacy which may be caused by the reason referred to below or by other unexpected accidental reasons.

If no reference biologic information is received in step S244 from any apartment in reply to the sending of the gotten biologic information in step S243, the flow goes to step S253 to display admission refusal indication, the display of the reason of refusal following in step S254.

Similarly in step 245, if the received reverence biologic information does not coincide with the biologic information gotten by commercial grade biologic information sensor 21, the flow goes to step S253 to display admission refusal indication, the display of the reason of refusal following in step S254.

In both the case above, the flow advances to step S255 to make available the auxiliary conventional authentication system such as password system or IC card system. And, if the auxiliary conventional authentication is successful in step S255, the flow goes to step S247 direct entrance lock 20 to unlock the entrance door. If the auxiliary conventional authentication is not made or unsuccessful in step S255, on the contrary, the flow goes to step S248 to delete the biologic information which has been gotten in step S242. Thus, even if the authentication is unsuccessful, there is sometimes necessary to delete the gotten biologic information for securing privacy protection.

In this case, if the predetermined time has not passed yet in step S249, the flow retunes to step S242 by way of step S241. So, it is possible to go to step S243 by way of step S242 if the person more carefully inserts the finger again with the indication made in step S254 taken into consideration.

In any case above, the flow gets to step S250 by way of step S249. In the case that the flow gets to step S253 from step S241 directly or from step S244, however, nothing seems to be carried out in step S250 since there has not been any reference biologic information received in first place. However, the flow is so arranged to go through step S250 without fail for protecting privacy violation which may be otherwise caused by some unexpected accidents.

Fourth Embodiment

The fourth embodiment is a modification of the embodiment in FIG. 14 including mobile-phone 101 in which the comparison of the biologic information for authentication is modified to be made by administration computer 19 as in the third embodiment. The block diagram of the fourth embodiment is similar to that of the embodiment in FIG. 14. So, the explanation of the third embodiment is to be made also with FIG. 14 used. The function of mobile-phone controller 106 of mobile-phone 101 and the function of administration controller 63 of administration computer 19 can be mostly understood on the basis of FIG. 17 and FIG. 18, respectively, duplicate explanation thereof being accordingly omitted with only different steps commented on.

In the fourth embodiment, step S223 can be omitted from the flow in FIG. 17. In other words, the third embodiment checks in step S223 where or not the received biologic information of the finger coincides with the reference biologic information stored in reference biologic information holder 14 since there is no necessity of sending reference biologic information to administration computer 19 if the received biologic information from administration computer 19 has no relation to the family in the first apartment 2. In the case of the fourth embodiment, on the contrary, it is necessary without question to send reference biologic information 19 from mobile-phone 101 to administration computer 19 since the biologic information received from administration computer 19 is of the mobile-phone keeper who stands in front of the entrance of condominium building 1 with his or her finger inserted into commercial grade biologic information sensor 21. Thus, the flow can go from step S222 directly to step S224 in the case of the fourth embodiment.

Further in the case of the fourth embodiment, mobile-phone controller 106 prepares in step S230 to display an indication of abnormality warning on mobile-phone display 110, in place television set 17, so that the indication is to be automatically made when its power switch of mobile-phone 101 is turned on.

Also in the flow of FIG. 18 administration computer 19 of the fourth embodiment in step S243 sends the gotten biologic information only to the third wireless local communication apparatus 105 of mobile-phone 101, in place of the personal computers in all the apartments.

Further in the case of the fourth embodiment, a step of is inserted between step S242 and step S243 in FIG. 18 to check whether or not the mobile-phone keeper is a user of "health control contract". And, the flow can go from step S242 to step S243 through the inserted step only when the mobile-phone keeper is the user. If the mobile-phone keeper is not the user, on the contrary, the flow goes from the inserted step to step S244 by way of a step of requesting the mobile-phone 101 to send the reference biologic information to administration computer 19. Thus, administration computer 19 determines whether or not to send the gotten biologic information to a mobile-phone in dependence on whether or not the mobile-phone is kept by a user of "health control contract". The above explanation of the function of mobile-phone controller 106 is based on the assumption that the keeper of mobile-phone 101 is a user of "health control contract".

In the case that the keeper of mobile-phone 101 is not a user of "health control contract", on the other hand, the function of mobile-phone controller 106 is very simple, the explanation of which is made on FIG. 17 with necessary modification commented below. In other words, the modification is that a step labeled with "reference information request" is substituted for step S222, and that step S223, steps S225 to S231, step S234 and step S235 are omitted. Thus, in the case that the keeper is not a user of "health control contract", mobile-phone 101 simply sends the reference biologic information to administration computer 19 and confirms the deletion of the same from administration computer 19.

Next, the process of checking the sensor is to be explained. Since the sensor checking process is common to the first to the fourth embodiment, the explanation is made on the first embodiment for example.

Figure 19:
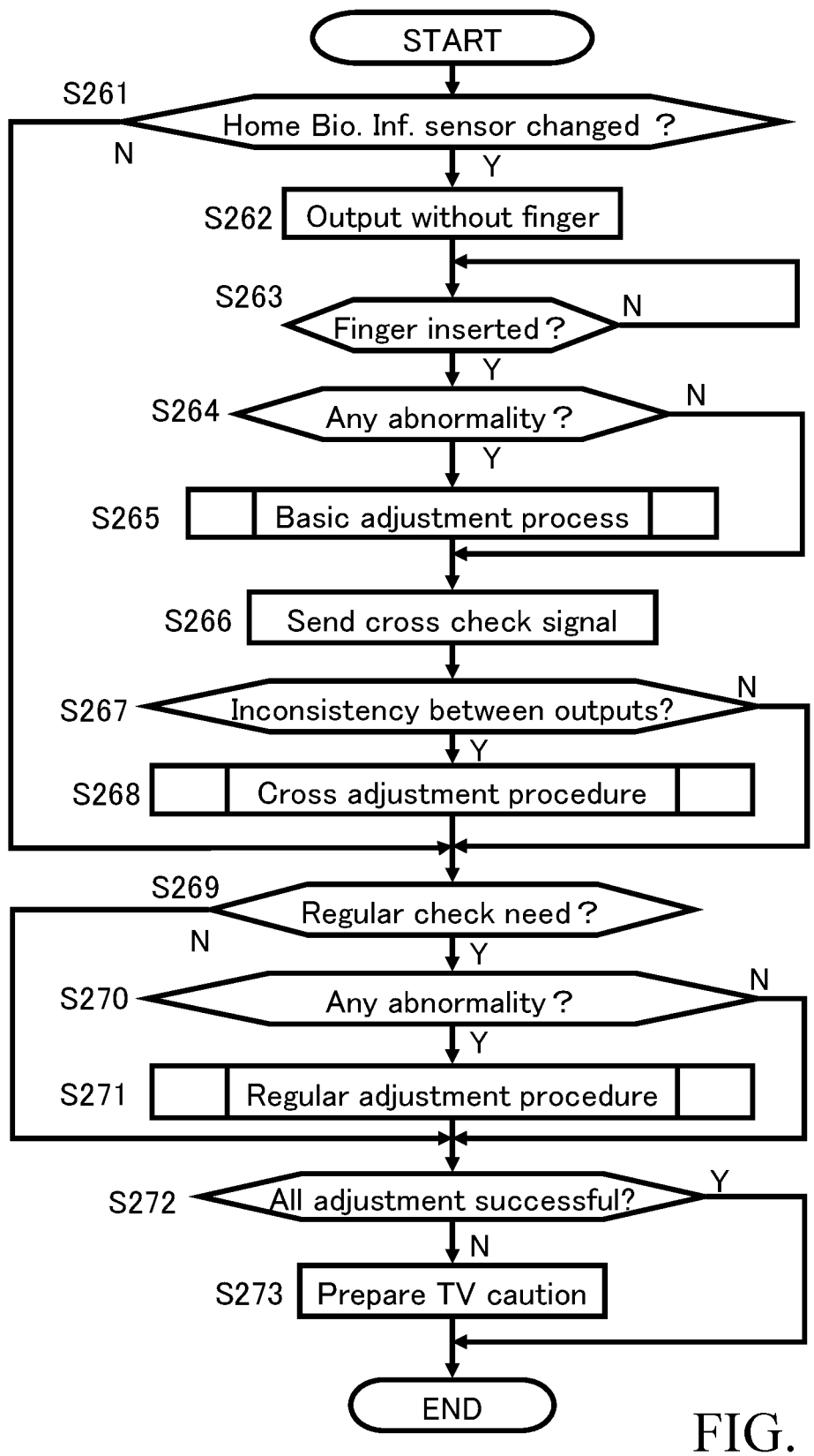
FIG. 19 is a flow chart showing the details of step 12 in FIG. 4 for the first embodiment.

FIG. 19 is a flow chart showing the details of step 12 in FIG. 4. If the flow starts, it is checked in step S261 whether or not home biologic information sensor 13 is changed. If the sensor is changed, the flow goes to step S262 to get output of home biologic information sensor 13 with no finger inserted. And then, the flow waits in step S263 for the insertion of a finger on a trial basis, the flow advancing to step S264 if the finger is inserted to cause output form home biologic information sensor 13.

In step 264, a basic signal check is done in which it is checked whether or not a sufficient output is gotten with the finger inserted in reference to the output gotten without the finger insertion. If any abnormality is detected on such a basic signal check, the flow goes to step S265 to make a basic adjustment, the flow going to step S266 on completion of such a basic adjustment. If there is no abnormality detected in step S264, on the contrary, the flow goes directly to step S266.

In step S266, a cross check signal is sent both to home biologic information sensor 13 and to commercial grade biologic information sensor 21. And, in step S267, it is checked whether the output of home biologic information sensor 13 corresponds to that of commercial grade biologic information sensor 21. If any inconsistency exists between the outputs in step S267, the flow goes to step S268 to make a cross check adjustment, in which the output level of the home biologic information sensor 13 is adjusted to come to an adequate level relative to the output level of commercial grade biologic information sensor 21. And then, the flow goes to step S269. If there is no inconsistency detected in step S267, on the contrary, the flow goes directly to step S269. If any change of home biologic information sensor 13 is not detected in step S261 at all, the flow also goes step S269.

In step S269, it is checked whether or not a predetermined period of time has passed since the latest regular check. The regular check may be done very often on a relatively short periodic base. If it is determined in step S269 that the predetermined period of time has passed to necessitate a regular check, the flow goes to step S270 to make a predetermined items of regular check. For example the similar cross check to those done in steps S266 and S267 in which the cross check signal is sent both to home biologic information sensor 13 and to commercial grade biologic information sensor 21 to checked whether or not a sufficient output is gotten from home biologic information sensor 13 without the finger inserted in reference to the output gotten from commercial grade biologic information sensor 21 without the finger insertion. If any abnormality is detected in step S270, the flow goes to step S271 to make a suitable regular adjustment procedure, the flow going to step S272 on completion of such a regular adjustment procedure. If there is no abnormality detected in step S270, on the contrary, the flow goes directly to step S272. If it is determined in step S269 that the predetermined period of time has not passed yet, the flow goes directly to step S272. Ether or not all the adjustments automatically done in steps S265, S268 and S271 have been successful. If any of the automatic adjustment is not successful, the flow goes to step S273 to prepare for display on television set 17 so that an indication of the abnormality is to be automatically made when its power switch is turned on, and the flow goes to the end. The function relating to step S273 for the display on television set 17 is similar to that in step S70.

The details of the process of checking the sensor by administration computer 19 in step S111 in FIG. 9 is basically similar to FIG. 19. However, the cross check process in steps S266 to S268 is unnecessary as to the function of administration computer 19. It should be noted that administration computer 19 carries out the regular check in steps S270 and S271 for commercial grade biologic information sensor 21 only. Further, administration computer 19 displays the indication of the abnormality on its own monitor in place of preparing for display on television set 17 in step S273.

Thus, the check and adjustment of commercial grade biologic information sensor 21 is done by administration computer 19. The first personal computer 5 believes in such a check and adjustment of commercial grade biologic information sensor 21 by administration computer 19 to carry out the cross check and adjustment of home biologic information sensor 13 in reference to commercial grade biologic information sensor 21.

Next, the past information comparison process is to be explained in detail. Since the past information comparison process is common to the first to the fourth embodiment, the explanation is made on the first embodiment for example.

Figure 20:
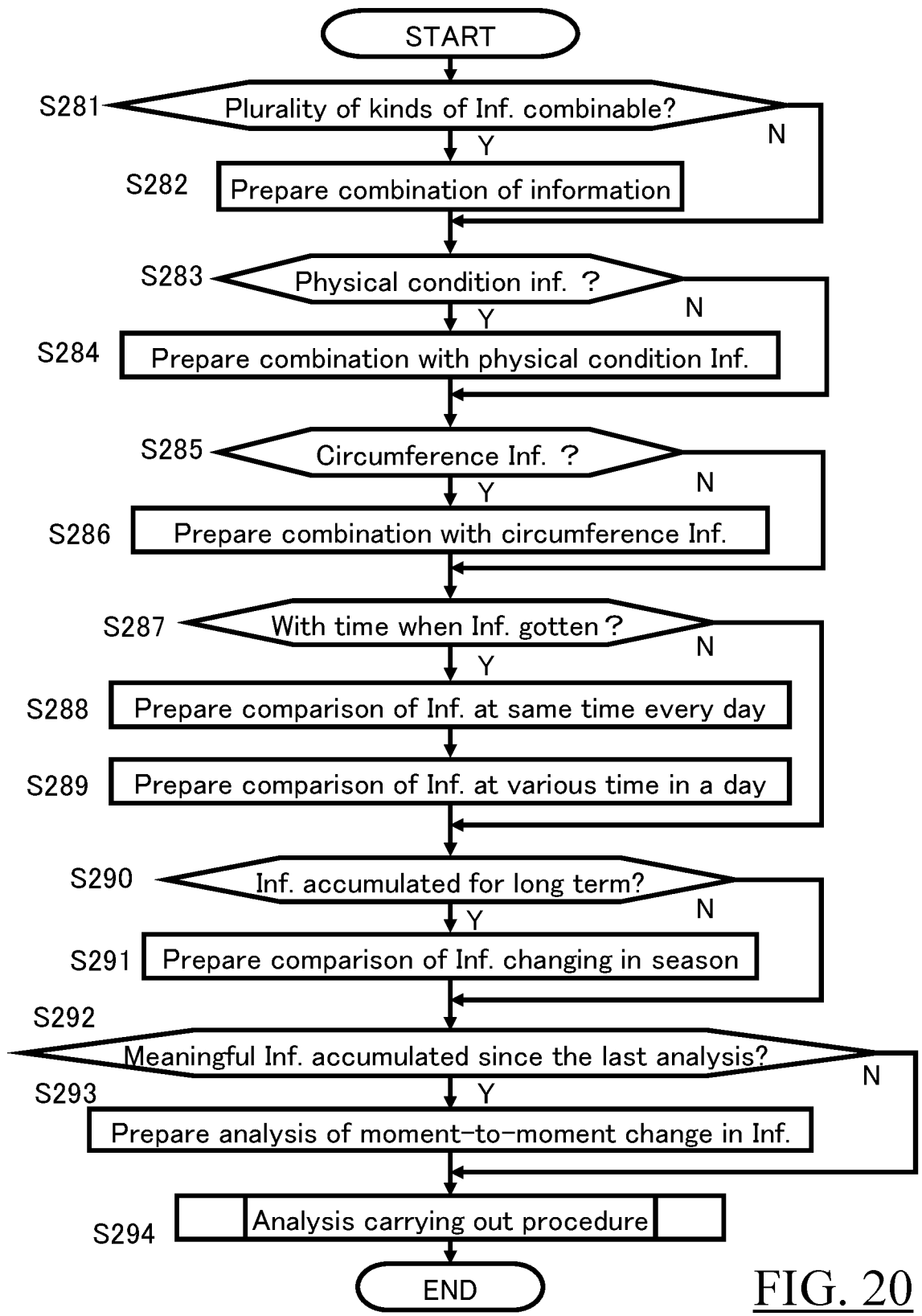
FIG. 20 is a flow chart showing the details of step 84 in FIG. 8 for the first embodiment.

FIG. 20 is a flow chart showing the details of past information comparison process of step 84 in FIG. 8. If the flow starts, it is checked in step S281 whether or not biologic information form different kinds of sensors, outputs of which are combinable with each other in analysis, are stored in individual health control database 15. If such biologic information from a plurality of different kinds of sensors are stored, the flow goes to step S282 to prepare these biologic information for comparison in combination, the flow going to step S283 after the preparation. If it is determined in step 281 that no biologic information of a sensor combinable with other biologic information of a different kind of sensor is stored, on the contrary, the flow goes directly to step S283.

The different kinds of sensors, outputs of which are combinable with each other in analysis are, for example, a blood vessel sensor, a funduscopic sensor, and a vocal print sensor, or the like, which are all capable of getting both authentication information and health control information. Such a combination of biologic information from a plurality of kinds of sensors is advantageous not only in reducing error in authentication, but also in achieving an advanced health control.

In step S283, it is checked whether or not biologic information not of authentication but of physical condition of a person to be authenticated by means of other biologic information is stored. If such biologic information is stored, the flow advances to step S284 for arranging these information to be combined for comparison, the flow going to step S285 after the arrangement function in step 284. If such biologic information is not stored, on the contrary, the flow directly advances to step S285. For example, the biologic information not of authentication but of condition of a person to be authenticated is body temperature, blood pressure and frequency of pulse, or the like.

Other than the above, examples of the biologic information not of authentication but of condition of a person to be authenticated is he fourth embodiment are as follows.

As a first example, a pedometer can be incorporated into mobile-phone 101 including individual health control database 109. In this case, not only a condition of a person at the moment of authentication, but also an exercise history until the moment of authentication can be gotten by pedometer and stored in individual health control database 109. In other words, even if the frequency of pulse at the moment of authentication are identical between two cases, the first case after walking exercise continued in one month and the second case after no exercise for the corresponding one month can be distinguished from each other in comparison of the gotten biologic information with the reference biologic information to diagnose the health condition on the result of comparison. Thus, an exercise history is a good example of the biologic information not of authentication but of condition of a person to be authenticated.

Further, the biologic information not of authentication but of condition of a person to be authenticated is not limited to the information of the person himself or herself, but also that of his or her family is useful. For example, even if the blood pressures are identical between two persons at the moment of authentication, the first person from a family of hypertension history and the second person from a family of normal blood pressure can be distinguished from each other in comparison of the gotten biologic information with the reference biologic information to diagnose the health condition on the result of comparison.

Medical institution 9 registers the reference biologic information with various conditions such as mentioned above in accordance with a decision of biologic information comparing software 24 or doctor 25. Thus, the necessary manner of comparison including combination of information depends on what reference information is registered solely or in combination in medical institution 9.

In step S285, is it is checked whether or not information relating to outside circumference influencing directly on the biologic information or indirectly on a person from which the biologic information is to be gotten. If such information is stored, the flow advances to step S286 for arranging these information to be combined for comparison, the flow going to step S287 after the arrangement function in step 286. If such biologic information is not stored, on the contrary, the flow directly advances to step S287.

For example, information relating to outside circumference is climate condition such as temperature, humidity and wind velocity, which are gotten by outside circumference sensor 57 in FIG. 3.

In step S287, it is checked whether or not time information is stored, the time information relating to a time when the biologic information, condition of the person to be authenticated and the outside circumference are gotten, respectively. If the time information is stored, the flow advances to step S288 to pick up the biologic information, physical condition information and the outside circumference information at same time every day among the accumulation of those information in individual health control database 15, the picked up information at same time every day being prepared for comparison with each other. Especially, the authentication information gotten from a person at the time of getting into office every morning by a biologic information sensor located at the entrance of the office is a good example of the biologic information having time information regularly accumulated every day without fail.

Next, in step S289, the biologic information, physical condition information and the outside circumference information gotten at various time of a same day are picked up among the accumulation of those information in individual health control database 15, the picked up information of the same day being prepared for comparison with each other to analyze the change in the information from morning till night.

After carrying out steps S288 and S289, the flow advances to step 290. If it is determined in step S287 that time information is not stored at all, on the contrary, the flow directly goes to step S290.

In step S290, it is checked whether or not the biologic information, physical condition information of the person to be authenticated and information of the outside circumference each with date have been accumulated for a predetermined meaningful long term such as one season. If such long term information have been accumulated in individual health control database 15, the flow advances to step S291 to prepare analysis of change in season of the biologic information, physical condition information and the outside circumference information, and then flow advancing to step S292. Since the biologic information is possibly influenced by the change in season, steps S291 is useful to analyze the correlation of the change in the biologic information and the transition of the season. If it is determined in step 290 that the biologic information with date information have not been accumulated yet for the predetermined meaningful term, on the contrary, the flow directly advances to step S292.

In step S292, it is checked whether or not the biologic information, physical condition information for the person to be authenticated and information of the outside circumference each with date have been accumulated for a predetermined term meaningful for analyzing moment-to-moment change since the similar analysis was done in the latest term. If such information have been accumulated in individual health control database 15, the flow advances to step S293 to prepare analysis of the moment-to-moment change in the biologic information, physical condition information and the outside circumference information, and then flow advancing to step S294. If it is determined in step 292 that the biologic information with date information have not been accumulated yet for the predetermined term, on the contrary, the flow directly advances to step S294. This is because that the rate of change in the information is important for moment-to-moment change analysis to detect abnormality of health. So, the flow directly goes from step S292 to step S294 if a time passed since the end of the latest term is insufficient to analyze the rate of moment-to-moment change in the biologic information.

In step S294, various analyses including the comparison between the gotten and accumulated biologic information, between those and the reference biologic information, and between combinations of various information are carried out on the basis of the preparation done in steps S282, S284, S286, S288, S289, S291 and S293.

Figure 21:
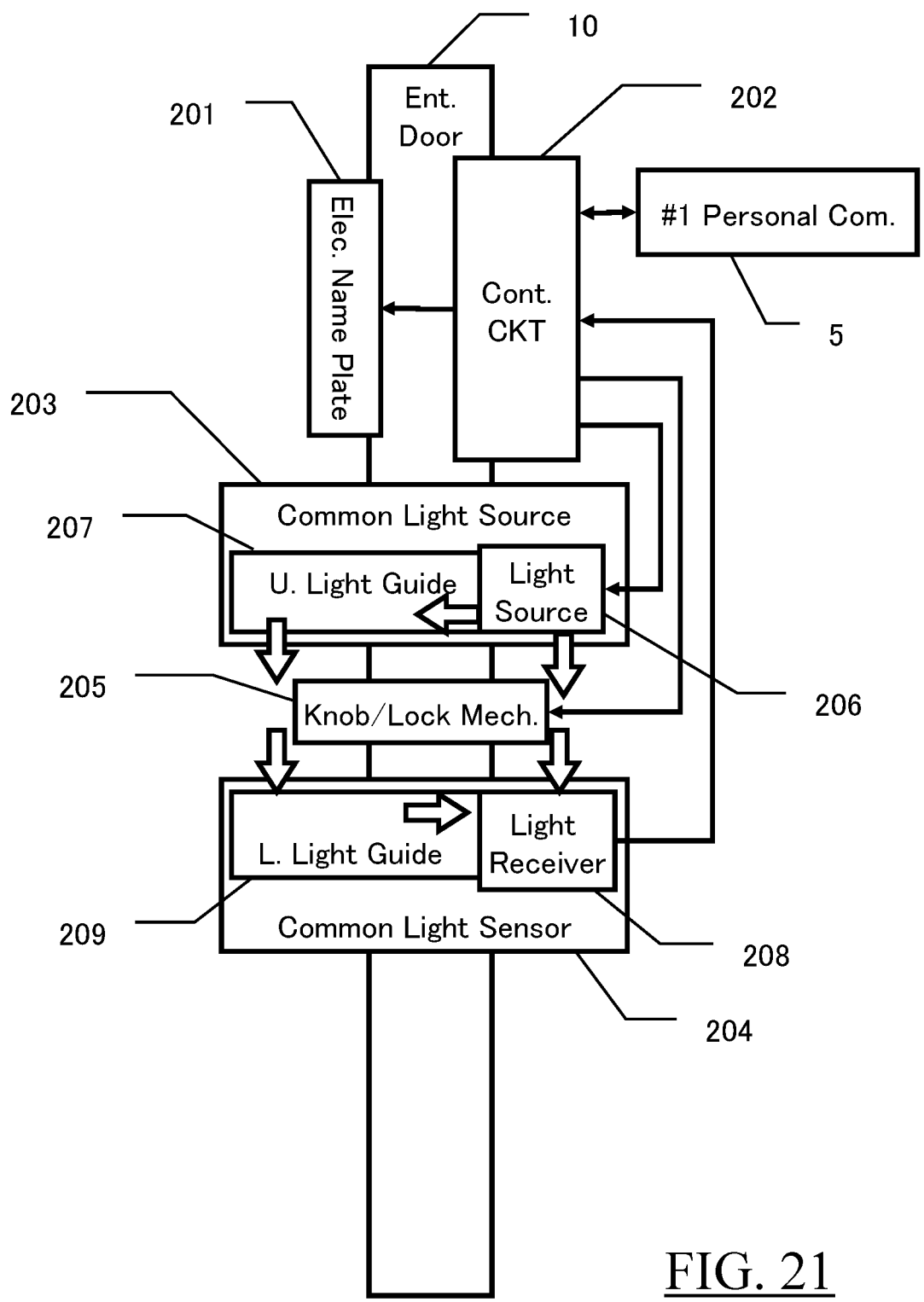
FIG. 21 is a schematic view of a structure of an entrance door for the first to fourth embodiments.

FIG. 21 is a schematic view of a structure of an entrance door commonly used for the first to fourth embodiments. FIG. 21 shows a cross-section of entrance door 10 with the left side thereof corresponding to outside of the first apartment 2 while the right side of entrance door 10 corresponds to the inside such as entrance hall. Elements shown in FIG. 14 basically correspond to door lock 11, home biologic information sensor 13 and a part for informing a person outside entrance door 10 of the admission refusal or the failure of getting health control information, respectively.

In detail, entrance door 10 includes on the outside thereof electronic name plate 201 formed of an electronic paper, which normally displays the family name. Electronic name plate 201 is under control of the first personal computer 5 by way of control circuit 202 located inside entrance door 10 to temporarily display the admission refusal or the failure of getting health control information in place of the family name as occasion arises.

Control circuit 202 also forms home biologic information sensor 13 along with common light source 203 and common light sensor 204, home biologic information sensor 13 of the above structure being under control of the first personal computer 5. Door knob and lock mechanism 205 along with control circuit 202 forms door lock 11, which is under control of the first personal computer 5.

FIG. 21 schematically shows the communication lines running in or out of control circuit 202 as if they are cables exposed in the entrance hall. Of course, the communication lines are practically wired within entrance door 10 to be hidden from the eye.

Door knob and lock mechanism 205 includes door knob to be touched for opening and closing entrance door 10 and the lock mechanism. The door knob is operable at both the inside and the outside. However, the lock mechanism cannot be unlocked at the outside unless the unlocking signal comes under control of the first personal computer 5 or someone manually unlocks it by rotating the door knob at the inside.

Common light source 203 and common light sensor 204, which are located on the opposite sides of door knob and lock mechanism 205, cooperate to get biologic information both at the inside and the outside of entrance door 10. In other words, a finger can naturally be inserted between common light source 203 and common light sensor 204 for detection of the biologic information in any one of both cases of touching the door knob at the outside and at the inside.

Thus, if a person really entitled to enter the first apartment 2 comes to the outside of entrance door 10 to touch door knob and lock mechanism 20, the biologic information is naturally gotten from the finger of the person and immediately authenticated to automatically unlock door knob and lock mechanism 20. This series of process is carried out so quickly that the person can operate the door knob to open entrance door 10 as if it is not locked.

On the other hand, if a person touches door knob and lock mechanism 20 at the inside to go out of entrance door 10, it can be manually unlocked without need of authentication. In this case, however, the biologic information itself is naturally gotten from the finger of the person touching door knob and lock mechanism 20. Thus, the biologic information can be regularly gotten every morning without fail when the person goes to daily work.

Now the explanation is directed to the detailed structure of common light source 203 and common light sensor 204. Common light source 203 includes light emitter 206 located at the inside of entrance door 10 for emitting light toward the inside door knob. Light emitter 206 also emits light toward the outside of entrance door 10, which light in turn is bended downward by upper light guide 207 toward the outside door knob. Thus, only one emitter 206 can illuminate both the inside door knob and the outside door knob.

Common light sensor 204 includes light receiver 208 located at the inside of entrance door 10 for receiving light by way of a finger touching the inside door knob. The light emitted downward from the exit of upper light guide 207 goes through a finger touching the outside door knob to incident lower light guide 209, which light in turn is bended rightward by lower light guide 209 toward the light receiver 208. Thus, only one light receiver 208 can receive light by way of both a finger touching the inside door knob and a finger touching the outside door knob.

Common light source 203 and common light sensor 204 are not only advantageous in that the biologic information can be gotten both at the inside and at the outside of entrance door 10 by means of one pair of light emitter 206 and light receiver 208, but also advantage for the following reason.

In other words, light emitter 206 and light receiver 208 as well as control circuit 202 are located at the inside of entrance door 10, which is advantageous in that these elements having a higher proportion of the cost of the entire system are protected from being damaged or vandalized from the outside. Thus, upper light guide 207 and lower light guide 209 serve as a protector similar to protection unit 52 in FIG. 3. Upper light guide 207 and lower light guide 209 are replaceable or adjustable independently form light emitter 206 and light receiver 208 as in the case of protection unit 52 in FIG. 3.

The above advantage of the structure for preventing main elements from being exposed to outside environment is also true in the embodiment in which the comparison of the biologic information for authentication is not carried out by the first personal computer 5 inside entrance door 10, but left to administration computer 19.

The light path from the light exit to the light entrance of the home biologic information sensor 13 is exposed to outside environment to be possibly interrupted by dust adhering to the light exit or the light entrance, or by a foreign matter sandwiched in between the light exit and the light entrance. So, the light path including the light exit and the light entrance have to be always maintained clean for the sensing of the biologic information not to be impossible or insufficient.

The structure in FIG. 21 is advantageous in that door knob and lock mechanism 205 is mechanically moved by a hand every time the authentication of a person is required. In other words, the light exit and the light entrance can be cleaned by a mechanical wiper every time upon authentication if the wiper is so arranged to be driven in conjunction with the movement of the door knob. As to a foreign matter possibly being sandwiched in between the light exit and the light entrance is expected to be naturally removed by a hand to touch the door knob.

Of course, the wiper can be electrically driven by a regularly actuated motor in place of being manually driven in conjunction with the movement of the door knob.

Fifth Embodiment

Figure 22:
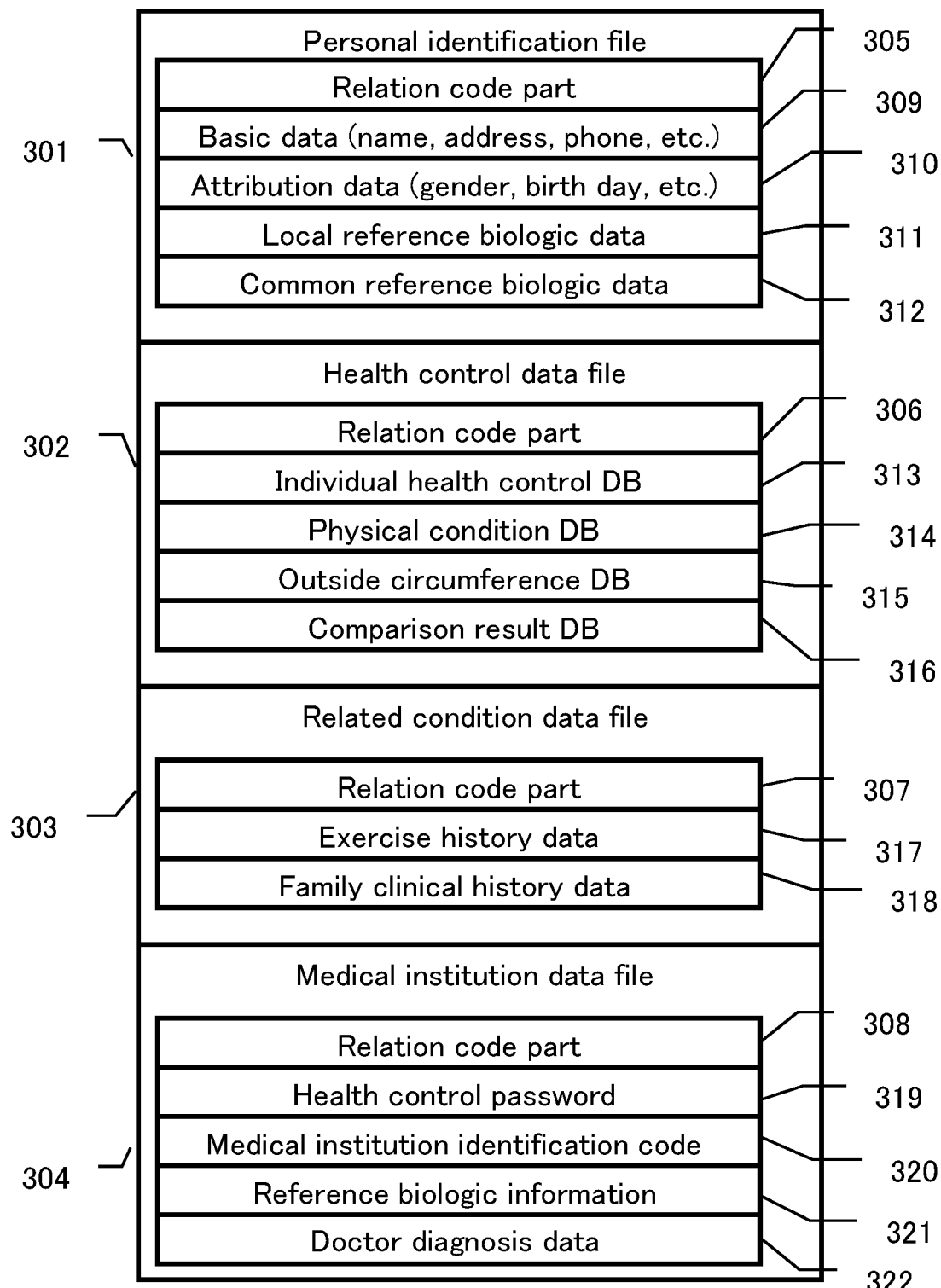
FIG. 22 is a chart showing a structure of biometric recognition data and health administration data for the fifth embodiment.

FIG. 22 is a chart showing a data structure for authentication and health control for the fifth embodiment. In the fifth embodiment, all the authentication information and health control information are integrated into one data format shown in FIG. 22 in contrast to the first to fourth embodiments in which various information are separately stored in reference biologic information holder 14, individual health control database 15 and reference health information holder 16, or the like. The first to fourth embodiments, however, can be easily modified so as to be practiced according to the integrated data format as in the fifth embodiment.

According to the integrated data format of the fifth embodiment, all data are basically integrated into one data format so as to be administrated as one file. The integrated data file consists of personal identification file 301, health control data file 302, related condition data file 303 and medical institution data file 304, which can be independently administrated and also be integrally administrated by means of relation code parts 305 to 308 of data files 301 to 304, respectively, the same unique code being allotted to all the relation code parts 305 to 308 in the same integral data file.

Personal identification file 301 includes basic data 309 for identifying a person, such as name, address and phone number, attribution data 310 to the person such as gender and birth day, local reference biologic data 311 for authenticating the entrance door of the apartment, and common reference biologic data 312 for authenticating the entrance of the condominium building.

All data in personal identification file 301 other than common reference biologic data 312 can be registered by the user himself, while common reference biologic data 312 can not be registered on the user's own, but can be registered only under the control of a common system such as administration computer 19 of entrance lock control system 8. On the other hand, medical institution 9 cannot access to local reference biologic data 311 and common reference biologic data 312 which have no relation to health control, but to unlock authentication exclusively.

When common reference biologic data 312 is sent to condominium building entrance lock control system 8 for the purpose of authentication, basic data 309 capable of identifying a person, such as name, address and phone number, attribution data 310 to the person such as gender and birth day and local reference biologic data 311 for authenticating the entrance door of the apartment are concealed so that condominium building entrance lock control system 8 cannot know whose common reference biologic data 312 is sent.

Health control data file 302 includes individual health control database 313 for storing biologic information with date and time when the information is gotten, 15, physical condition database 314 for storing biologic information not of authentication but of condition of a person when the biologic information for authentication is gotten, outside circumference data base 315 for storing outside circumference influencing on the person when the biologic information is gotten, and comparison result database 316 for storing the result of comparison.

The authentication system such as condominium building entrance lock control system 8 cannot access health control data file 302. If a person is to access his or her own health control data file 302, it is necessary for the person to have his or her biologic information compared with local reference biologic data 311 for authentication. Thus, a stranger cannot access such health control database 302 of another.

Related condition data file 303 includes exercise history data 317 for storing a record by pedometer for example and family clinical history data 318 for storing clinical history of the family other than the client.

Authentication system such as condominium building entrance lock control system 8 cannot access related condition data file 303. If a person is to access his or her own related condition data file 303, it is necessary for the person to have his or her biologic information compared with local reference biologic data 311 for authentication. Thus, a stranger cannot access such related condition data file 303 of another.

Medical institution data file 304 includes various data to be treated under administration of medical institution 9. Medical institution 9, however, cannot access health control data file 302 since medical institution 9 is not a person itself nor has any relation to local reference biologic data 311 and common reference biologic data 312 of the person. So, for the purpose of making it possible for medical institution 9 to access health control data file 302, health control password 319 is given to be stored in Medical institution data file 304 under authorization of the patient. Thus, doctor 25 can access health control data file 302 by inputting health control password 319.

Other than health control password 319, medical institution data file 304 includes medical institution identification code 320, reference biologic information 321 for health control and doctor diagnosis data 322, which are under administration of medical institution 9, even a patient himself or herself being incapable of modifying them on its own.

Reference biologic information 321, which has been registered in medical institution data file 304 is automatically transmitted to the first personal computer 5 or to mobile-phone 101 in general. The transmission of doctor diagnosis data 322 is, however, postponed until a predetermined prosecution has been completed. This is because a notification of a serious disease should be sometimes done very carefully.

As has been discussed above, the biometrics deeply relates to the contradiction between the issue of the forgery of biologic information and the issue of infringement of privacy through the biologic information. The embodiments according to this invention are for solving the contradiction. The following modification of the second embodiment is also useful for solving the contradiction, the explanation of the modification being made in accordance with FIG. 14.

The modification includes a second commercial grade biologic information sensor under the administration by condominium building entrance lock control system 8. The second commercial grade biologic information sensor is separable from condominium building entrance lock control system 8 for the purpose of creating the reference biologic information. Upon creation of the reference biologic information, in more detail, the second commercial grade biologic information sensor completely isolated from condominium building entrance lock control system 8 is connected to mobile-phone 101 of the keeper who comes to an office where condominium building entrance lock control system 8 is located. And, the biologic information gotten from the second commercial grade biologic information sensor with a finger of the keeper inserted is input into mobile-phone 101 to be encrypted into a first encrypted reference biologic information according to a mobile-phone encryption system under the control of mobile-phone controller 106.

The first encrypted reference biologic information is sent to condominium building entrance lock control system 8 by way of the third wireless local communication apparatus 105 and the first wireless local communication apparatus 102. The received first encrypted reference biologic information is further encrypted into a second encrypted reference biologic information according to an unlock encryption system under the control of administration controller 20. The second encrypted reference biologic information is sent back to mobile-phone 101 by way of the first wireless local communication apparatus 102 and the third wireless local communication apparatus 105. The received second encrypted reference biologic information is finally stored into reference biologic information holder 107.

Thus, the second encrypted reference biologic information is of a nature incapable of being created by the mobile-phone keeper by itself because of the necessity of the unlock encryption system exclusively controlled by administration controller 20 as well as incapable of being decrypted by condominium building entrance lock control system 8 because of the mobile-phone encryption system exclusively controlled by mobile-phone controller 106. Further, condominium building entrance lock control system 8 cannot access to the raw biologic information since the second commercial grade biologic information sensor is completely isolated from administration condominium building entrance lock control system 8 upon getting the reference biologic information. On the other hand, anyone is incapable of creating the reference biologic information unless he or she comes to the office where condominium building entrance lock control system 8 is located, since mobile-phone 101 is only be allowed to be connected to the second commercial grade biologic information sensor at the office.

Upon authentication, in the case of comparison at mobile-phone 101, biologic information gotten by commercial grade biologic information sensor 21 is encrypted into a first encrypted gotten reference biologic information according to the unlock encryption system under control of administration controller 20. The first encrypted gotten biologic information is sent to mobile-phone 101 by way of the first wireless local communication apparatus 102 and the third wireless local communication apparatus 105. At mobile-phone 101, the encrypted gotten biologic information is encrypted into a second encrypted gotten biologic information according to the mobile-phone encryption system under control of mobile-phone controller 106. The second encrypted gotten biologic information is compared with the second encrypted reference biologic information stored in reference biologic information holder 107. Since the second encrypted gotten biologic information and the second encrypted reference biologic information both are encrypted through both the unlock encryption system and the mobile-phone encryption system, the order of the encryption having no influence on the resultant encrypted biologic information, the second encrypted gotten biologic information coincides with the second encrypted reference biologic information if the origin of raw gotten biologic information is the same as that of the raw reference biologic information.

If the second encrypted gotten biologic information coincides with the second encrypted reference biologic information, mobile-phone 101 sends the unlock command signal to condominium building entrance lock control system 8 by way of the third wireless local communication apparatus 105 and the first wireless local communication apparatus 102 within a very short period directed by administration command from administration computer 19. Administration computer 19 cannot identify the keeper since the unlock signal includes no biologic information.

The followings are not any limitations, but summarization of various features of this invention for example:

1. A biometrics system comprising a first part including a first sub-part for administrating the registration of a reference biologic information and a second sub-part for utilizing a result of a biometrics recognition, and a second part including a third sub-part for holding the reference biologic information registered under the administration by the first sub-part.

2. The biometrics system according to feature 1, wherein the first part is commonly utilized by a plurality of persons, while the second part is individually utilized by an identified person.

3. The biometrics system according to feature 2, wherein the first part is incapable of holding the reference biologic information.

4. The biometrics system according to feature 2 or 3 wherein the first part is a lock control system for an entrance door commonly utilized by a plurality of persons, and wherein the second sub-part is capable of unlocking the common entrance door depending on a result of the biometrics recognition.

5. The biometrics system according to feature 4, wherein the second part is administrated by an identified person who utilizes the entrance door.

6. The biometrics system according to feature 5, wherein the second part is held by an individual person who utilizes the common door.

7. The biometrics system according to feature 1, wherein the first part is a bank system for authenticating a customer of the bank and the second sub-part is capable of authenticating the customer depending on a result of a biometrics recognition.

8. The biometrics system according to any of features 1 to 7, wherein the second part is a mobile-phone.

9. The biometrics system according to feature 1, wherein the first part further including a fourth sub-part for getting the reference biologic information and a fifth sub-part for transmitting the reference biologic information to the second part.

10. The biometrics system according to feature 9, wherein the first sub-part is capable of deleting form the first part the reference biologic information which has been gotten by the fourth sub-part and then held by the third sub-part.

11. The biometrics system according to feature 10, wherein the first sub-part is incapable of deleting the reference biologic information from the first part unless the reference biologic information gotten by fourth sub-part has been held by the third sub-part.

12. The biometrics system according to one of features 9 to 11, wherein the second part further includes a sixth sub-part for transmitting the reference biologic information held by the third sub-part back to the first part upon authenticating a person.

13. The biometrics system according to feature 12, wherein the fourth sub-part is also capable of getting biologic information upon authenticating the person.

14. A biometrics system according to feature 13, wherein the fifth sub-part is also capable of transmitting the authentication biologic information gotten by the fourth sub-part to the second part, wherein the second part further including a seventh sub-part for comparing the transmitted authentication biologic information with the reference biologic information held by third sub-part, and wherein the sixth sub-part is also capable of transmitting to the first part the result of the comparison by the seventh sub-part as a biometrics recognition to be utilized by the second sub-part.

15. The biometrics system according to feature 13, wherein the sixth sub-part is capable of transmitting the reference biologic information to the first part, wherein the first part further includes an eighth sub-part for comparing the transmitted reference biologic information with the authentication biologic information which has been gotten by the fifth sub-part, and wherein the second sub-part is capable of utilizing the result of the comparison by the seventh sub-part as biometrics recognition.

16. The biometrics system according to one of features 1 to 8, wherein the second part further includes a ninth sub-part for getting the reference biologic information, the second part being under administration by the first sub-part in getting the reference biologic information with the ninth sub-part and in holding the same in the third sub-part.

17. A biometrics system comprising a first part for administrating the registration of a reference biologic information, a second part for utilizing a result of a biometrics recognition, and a third part for receiving information relating to the reference biologic information when a biometrics recognition is required.

18. The biometrics system according to feature 17, wherein the system is incapable of holding the reference biologic information which has been registered under control of the first part.

19. The biometrics system according to feature 17 or 18, wherein the system is a lock control system of an entrance door commonly utilized by a plurality of persons, wherein the second part is capable of unlocking the common entrance door depending on a result of the biometrics recognition.

20. The biometrics system according to one of features 17 to 19, further comprising a fourth part for getting the reference biologic information and a fifth part for transmitting the reference biologic information.

21. The biometrics system according to feature 20, wherein the first is capable of deleting the reference biologic information gotten by the fourth part after the reference biologic information has been transmitted by the fifth part.

22. The biometrics system according to feature 21, wherein the fourth part is also capable of getting authentication biologic information when a biometrics recognition is required.

23. The biometrics system according to feature 22, wherein the fifth part is capable of transmitting the authentication biologic information gotten by the fourth part, and wherein the second part is capable of utilizing, as the result of the biometrics recognition, the information relating to the reference biologic information received by the third part in response to the transmission of the authentication biologic information by the fifth part.

24. The biometrics system according to feature 22, further comprising a sixth part for comparing the reference biologic information received by the third part with the authentication biologic information gotten by the fourth part, and wherein the second part is capable of utilizing as the result of the biometrics recognition the result of the comparison by the seventh part.

25. The biometrics system according to feature 22, wherein the fourth part is exchangeable apart from the second part, and wherein the biometrics system further comprises a seventh part for checking operations of an newly exchanged fourth part.

26. A biometrics system comprising: a first part for holding a reference biologic information, and a second part for transmitting information relating to the reference biologic information held by the first part when a biometrics recognition is required.

27. The biometrics system according to feature 26, wherein the reference biologic information held by the first part is for unlocking a door commonly utilized by a plurality of persons, and wherein the biometrics system is under control of a particular person utilizing the common door.

28. The biometrics system according to feature 27, wherein the biometrics system is capable of being held by the particular person utilizing the common door.

29. The biometrics system according to feature 26, wherein the reference biologic information held by the first part is for use in a person authentication system of a bank, and wherein the biometrics system is under control of an individual bank customer.

30. The biometrics system according to feature 26, wherein the biometrics system is constituted as a mobile-phone.

What is claimed is:

1. A mobile phone for storing health control information of a person carrying the mobile phone comprising:

two communication apparatuses housed within the mobile phone consisting of a mobile phone communication apparatus that communicates via a cellular communications network and a wireless local communication apparatus other than the mobile phone communication apparatus that communicates by a network other than the cellular communications network, wherein the wireless local communication apparatus is configured to receive the health control information of the person carrying the mobile phone from first and second biologic information sensors which are located external to the mobile phone, wherein one of the first and second biologic information sensors which is within a limited communication range of the wireless local communication apparatus is accessible by the public including the person carrying the mobile phone, wherein the second biologic information sensor is controlled by a medical institution accessible by the public including the person carrying the mobile phone, and wherein the wireless local communication apparatus receives the health control information of the person carrying the mobile phone from one of the first and second biologic information sensors which is within the limited communication range of the wireless local communication apparatus when the person is within the communication range of either of the first and second biologic information sensors;

a storage part that stores the health control information received from the first and/or second biologic information sensors and stores software received from the medical institution, the software being necessary for the mobile phone to receive, store, and display the health control information from the first and/or second biologic information sensors;

a processor that implements the software from the storage part;

a controller that facilitates communication between the mobile phone communication apparatus and the medical institution for receipt of the software and for communication relating to the health control information received from the first and/or second biologic information sensors using the software by means of the wireless local communication apparatus; and a display that displays the health control information received from the first and/or second biologic information sensors and that is received using the software wherein the displayed health control information is displayed as a graph plotting the moment-to-moment change in the biologic information, wherein the wireless local communication apparatus is activated and receives the health control information of the person carrying the mobile phone from the second biologic information sensor while the mobile phone communication apparatus is deactivated for the mobile phone communication and for the receipt of the software from the medical institution, wherein the mobile phone utilizes a first configuration mode in which the mobile phone communication apparatus is activated and the wireless local communication apparatus is activated and the wireless local communication apparatus receives the health control information from the first biologic information sensor and does not receive the health control information from the second biological sensor, and a second configuration mode in which the mobile phone communication apparatus is deactivated and the wireless local communication apparatus is activated and the wireless local communication apparatus receives the health control information from the second biologic information sensor and does not receive the health control information from the first biological sensor.

2. The mobile phone according to claim 1, wherein the health control information of the person visiting the medical institution is sensed by the second biologic information sensor and is received from the second biologic information sensor by means of the wireless local communication apparatus.

3. The mobile phone according to claim 1, wherein the controller communicates with the medical institution by means of the mobile phone communication apparatus for maintenance of the software necessary for receiving, storing, and displaying the health control information.

4. The mobile phone according to claim 3, wherein the controller receives new software from the medical institution if the second biologic information sensor is upgraded.

5. The mobile phone according to claim 1, wherein the controller sends the health control information to a data base of the medical institution by means of the mobile phone communication apparatus.

6. The mobile phone according to claim 5, wherein the health control information is sent to the data base of the medical institution through the internet.

7. The mobile phone according to claim 5, wherein the controller communicates with the medical institution by means of the mobile phone communication apparatus for registering the person into the medical institution.

8. The mobile phone according to claim 7, wherein the controller communicates with the medical institution by means of the mobile phone communication apparatus for registering the mobile phone into the medical institution.

9. The mobile phone according to claim 8, wherein the controller receives the health control information from the data base of the medical institution by means of the mobile phone communication apparatus in response to the registration of the mobile phone if the registration of the person has already been performed and the data base contains the health control information for the registered person.

10. A mobile phone for storing health control information of a person carrying the mobile phone comprising:

two communication apparatuses housed within the mobile phone consisting of a mobile phone communication apparatus that communicates via a cellular communications network and a wireless local communication apparatus other than the mobile phone communication apparatus that communicates by a network other than the cellular communications network, wherein the wireless local communication apparatus is configured to receive the health control information of the person carrying the mobile phone from first and second biologic information sensors which are located external to the mobile phone, wherein one of the first and second biologic information sensors which is within a limited communication range of the wireless local communication apparatus is accessible by the public including the person carrying the mobile phone, wherein the second biologic information sensor is controlled by a medical institution accessible by the public including the person carrying the mobile phone, and wherein the wireless local communication apparatus receives the health control information of the person carrying the mobile phone from one of the first and second biologic information sensors which is within the limited communication range of the wireless local communication apparatus when the person is within the communication range of either of the first and second biologic information sensors;

a storage part that stores the health control information received from the first and/or second biologic information sensors and stores software received from the medical institution, the software being necessary for the mobile phone to receive, store, and display the health control information from the first and/or second biologic information sensors;

a processor that implements the software from the storage part;

a controller that facilitates communication between the mobile phone communication apparatus and the medical institution for receipt and maintenance of the software stored in the storage part by means of the wireless local communication apparatus; and a display that displays the health control information received from the first and/or second biologic information sensors and that is received using the software wherein the displayed health control information is displayed as a graph plotting the moment-to-moment change in the biologic information wherein the wireless local communication apparatus is activated and receives the health control information of the person carrying the mobile phone from the second biologic information sensor while the mobile phone communication apparatus is deactivated for the mobile phone communication and for the receipt of the software from the medical institution, wherein the mobile phone utilizes a first configuration mode in which the mobile phone communication apparatus is activated and the wireless local communication apparatus is activated and the wireless local communication apparatus receives the health control information from the first biologic information sensor and does not receive the health control information from the second biological sensor, and a second configuration mode in which the mobile phone communication apparatus is deactivated and the wireless local communication apparatus is activated and the wireless local communication apparatus receives the health control information from the second biologic information sensor and does not receive the health control information from the first biological sensor.

11. The mobile phone according to claim 10, wherein the health control information of the person visiting the medical institution is sensed by the second biologic information sensor and is received from the second biologic information sensor by means of the wireless local communication apparatus.

12. The mobile phone according to claim 10, wherein the controller receives new software from the medical institution if the second biologic information sensor is upgraded.

13. A mobile phone for storing health control information of a person carrying the mobile phone comprising:

two communication apparatuses housed within the mobile phone consisting of a mobile phone communication apparatus that communicates via a cellular communications network and a wireless local communication apparatus other than the mobile phone communication apparatus that communicates by a network other than the cellular communications network, wherein the wireless local communication apparatus is configured to receive the health control information of the person carrying the mobile phone from first and second biologic information sensors which are located external to the mobile phone, wherein one of the first and second biologic information sensors which is within a limited communication range of the wireless local communication apparatus is accessible by the public including the person carrying the mobile phone, wherein the second biologic information sensor is controlled by a medical institution accessible by the public including the person carrying the mobile phone, and wherein the wireless local communication apparatus receives the health control information of the person carrying the mobile phone from one of the first and second biologic information sensors which is within the limited communication range of the wireless local communication apparatus when the person is within the communication range of either of the first and second biologic information sensors;

a storage part that stores the health control information of the person carrying the mobile phone received from the first and/or second biologic information sensors and stores software received from the medical institution, the software being necessary for the mobile phone to receive, store, and display the health control information from the first and/or second biologic information sensors;

a processor that implements the software from the storage part;

a controller that facilitates communication between the mobile phone communication apparatus and the medical institution for receipt of the software and for sending the health control information to the medical institution, wherein the controller is configured to facilitates communication between the mobile phone communication apparatus and the medical institution for registering the person and the mobile phone into the medical institution; and a display that displays the health control information received from the first and/or second biologic information sensors and that is received using the software wherein the displayed health control information is displayed as a graph plotting the moment-to-moment change in the biologic information, wherein the wireless local communication apparatus is activated and receives the health control information of the person carrying the mobile phone from the second biologic information sensor while the mobile phone communication apparatus is deactivated for the mobile phone communication and for the receipt of the software from the medical institution, wherein mobile phone utilizes a first configuration mode in which the mobile phone communication apparatus is activated and the wireless local communication apparatus is activated and the wireless local communication apparatus receives the health control information from the first biologic information sensor and does not receive the health control information from the second biological sensor, and a second configuration mode in which the mobile phone communication apparatus is deactivated and the wireless local communication apparatus is activated and the wireless local communication apparatus receives the health control information from the second biologic information sensor and does not receive the health control information from the first biological sensor.

14. The mobile phone according to claim 13, wherein the controller communicates with the medical institution through the internet.

15. The mobile phone according to claim 13, wherein the controller receives the health control information from the medical institution by means of the mobile phone communication apparatus in response to the registration of the mobile phone if the registration of the person has already been performed and the medical institution contains the health control information for the registered person.

16. The mobile phone according to claim 13, wherein the controller communicates with a database in the medical institution by means of the mobile phone communication apparatus.

* * * * *